United States Patent
Wang et al.

(10) Patent No.: US 10,738,007 B2
(45) Date of Patent: Aug. 11, 2020

(54) AMIDE COMPOUNDS AS KINASE INHIBITORS, COMPOSITIONS AND METHODS OF TREATMENT

(71) Applicant: TRANSLATIONAL DRUG DEVELOPMENT, LLC, Scottsdale, AZ (US)

(72) Inventors: Tong Wang, Scottsdale, AZ (US); Stephen Gately, Scottsdale, AZ (US)

(73) Assignee: Translation Drug Development, LLC, Scottsdale, AZ (US)

( * ) Notice: Subject to any disclaimer, the term of this patent is extended or adjusted under 35 U.S.C. 154(b) by 0 days.

(21) Appl. No.: 16/393,868

(22) Filed: Apr. 24, 2019

(65) Prior Publication Data

US 2019/0248744 A1    Aug. 15, 2019

Related U.S. Application Data

(63) Continuation-in-part of application No. PCT/US2017/058071, filed on Oct. 24, 2017.

(60) Provisional application No. 62/411,908, filed on Oct. 24, 2016, provisional application No. 62/662,105, filed on Apr. 24, 2018, provisional application No. 62/788,461, filed on Jan. 4, 2019.

(51) Int. Cl.
   *C07D 213/04* (2006.01)
   *C07D 487/04* (2006.01)

(52) U.S. Cl.
   CPC .......... *C07D 213/04* (2013.01); *C07D 487/04* (2013.01)

(58) Field of Classification Search
   CPC ............................ C07D 213/04; C07D 487/04
   USPC .......................................................... 546/329
   See application file for complete search history.

(56) References Cited

U.S. PATENT DOCUMENTS

| 7,384,963 | B2 * | 6/2008 | Angell ................ C07D 231/12 514/364 |
| 7,875,600 | B2 * | 1/2011 | Gillespie .............. C07D 401/12 514/183 |
| 8,008,327 | B2 * | 8/2011 | DiSalvo ............... C07D 401/12 514/322 |
| 9,079,880 | B2 | 7/2015 | Ginn et al. |
| 9,382,197 | B2 | 7/2016 | Blackburn et al. |

FOREIGN PATENT DOCUMENTS

| WO | 2012/006202 A1 | 1/2012 |
| WO | 2012/006203 A1 | 1/2012 |

OTHER PUBLICATIONS

Rajagopalan, Lakshman E. et al., "Biochemical, Cellular, and Anti-Inflammatory Properties of a Potent, Selective, Orally Bioavailable Benzamide Inhibitor of Rho Kinase Activity", The Journal of Pharmacology and Experimental Therapeutics, 333(3):707-716 (2010).
The International Search Report and the Written Opinion of the International Searching Authority, or the Declaration for PCT/US2017/058071 (dated Feb. 5, 2018).

* cited by examiner

*Primary Examiner* — Niloofar Rahmani
(74) *Attorney, Agent, or Firm* — Rodney J. Fuller; Booth Udall Fuller, PLC

(57) ABSTRACT

The present disclosure relates to certain amides and heterocyclic compounds. The present disclosure also relates to uses of these compounds to inhibit Rho-associated protein kinases and treat diseases including autoimmune disorders, graft versus host disease (GVHD), inflammation, cardiovascular disorders, central nervous system disorders, and neoplastic disorders.

19 Claims, No Drawings

AMIDE COMPOUNDS AS KINASE INHIBITORS, COMPOSITIONS AND METHODS OF TREATMENT

CROSS REFERENCE TO RELATED APPLICATIONS

This application is a continuation-in-part of International Application No. PCT/US2017/058071, filed on Oct. 24, 2017, which claims the benefit of U.S. Provisional Patent Applications No. 62/411,908, filed on Oct. 24, 2016; this application also claims the benefit of U.S. Provisional Patent Applications No. 62/662,105 filed on Apr. 24, 2018, and No. 62/788,461, filed on Jan. 4, 2019, the contents of each of which are incorporated herein by reference in their entirety.

FIELD OF THE INVENTION

The present invention relates to amide compounds, their compositions, and medicaments containing the same, as well as processes for the preparation and use of such compounds, compositions and medicaments. Such compounds are potentially useful in the treatment of diseases associated with inappropriate tyrosine and/or serine/threonine kinase activities including cell proliferation diseases (e.g., cancer) and neurological and inflammatory diseases. Specifically, this disclosure is concerned with compounds and compositions inhibiting Rho-associated protein kinases, methods of treating diseases associated with Rho-associated protein kinases, and methods of synthesizing these compounds.

BACKGROUND OF THE INVENTION

An important large family of enzymes is the protein kinase enzyme family. Currently, there are about 500 different known protein kinases. Protein kinases serve to catalyze the phosphorylation of an amino acid side chain in various proteins by the transfer of the γ-phosphate of the ATP-Mg$^{2+}$ complex to said amino acid side chain. These enzymes control the majority of the signaling processes inside the cells, thereby governing cell function, growth, differentiation, and destruction (apoptosis) through reversible phosphorylation of the hydroxyl groups of serine, threonine and tyrosine residues in proteins. Studies have shown that protein kinases are key regulators of many cell functions, including signal transduction, transcriptional regulation, cell motility, and cell division. Several oncogenes have also been shown to encode protein kinases, suggesting that kinases play a role in oncogenesis. These processes are highly regulated, often by complex intermeshed pathways where each kinase will itself be regulated by one or more kinases. Consequently, aberrant or inappropriate protein kinase activity can contribute to the rise of disease states associated with such aberrant kinase activity. Due to their physiological relevance, variety, and ubiquitousness, protein kinases have become one of the most important and widely studied families of enzymes in biochemical and medical research.

The protein kinase family of enzymes is typically classified into two main subfamilies: Protein Tyrosine Kinases and Protein Serine/Threonine Kinases, based on the amino acid residue they phosphorylate. The serine/threonine kinases (PSTK), include cyclic AMP- and cyclic GMP-dependent protein kinases, calcium- and phospholipid-dependent protein kinases, calcium- and calmodulin-dependent protein kinases, casein kinases, cell division cycle protein kinases, and others. These kinases are usually cytoplasmic or associated with the particulate fractions of cells, possibly by anchoring proteins. Aberrant protein serine/threonine kinase activity has been implicated or is suspected in a number of pathologies such as rheumatoid arthritis, psoriasis, septic shock, bone loss, many cancers, and other proliferative diseases. Accordingly, serine/threonine kinases and the signal transduction pathways which they are part of are important targets for drug design. The tyrosine kinases phosphorylate tyrosine residues. Tyrosine kinases play an equally important role in cell regulation. These kinases include several receptors for molecules such as growth factors and hormones, including epidermal growth factor receptor, insulin receptor, platelet derived growth factor receptor, and others. Studies have indicated that many tyrosine kinases are transmembrane proteins with their receptor domains located on the outside of the cell and their kinase domains on the inside. Much work is also under progress to identify modulators of tyrosine kinases as well.

A major signal transduction systems utilized by cells is the RhoA-signaling pathways. RhoA is a small GTP binding protein that can be activated by several extracellular stimuli such as growth factor, hormones, mechanic stress, osmotic change, as well as high concentration of metabolite like glucose. RhoA activation involves GTP binding, conformation alteration, post-translational modification (geranylgeranyllization and famesylation), and activation of its intrinsic GTPase activity. Activated RhoA is capable of interacting with several effector proteins including ROCKs and transmit signals into cellular cytoplasm and the nucleus.

Rho-associated protein kinases, ROCK1 and ROCK2, constitute a family of kinases that can be activated by RhoA-GTP complex via physical association. Activated ROCKs phosphorylate a number of substrates and play important roles in pivotal cellular functions. The substrates for ROCKs include the myosin binding subunit of myosin light chain phosphatase (MBS, also named MYPT1), addu-cin, moesin, myosin light chain (MLC), LIM kinase, as well as transcription factor FHL. The phosphorylation of these substrates modulates the biological activity of the proteins and thus provides a means to alter a cell's response to external stimuli.

One well documented example is the participation of ROCK in smooth muscle contraction. Upon stimulation by phenylephrine, the vascular smooth muscle contracts. Studies have shown that phenylephrine stimulates alpha-adrenergic receptors and leads to the activation of RhoA. Activated RhoA in turn stimulates kinase activity of ROCK1 that in turn phosphorylates MBS. Such phosphorylation inhibits the enzyme activity of myosin light chain phosphatase and increases the phosphorylation of myosin light chain itself by a calcium-dependent myosin light chain kinase (MLCK) and consequently increases the contractility of the myosin-actin bundle, leading to smooth muscle contraction. This phenomenon is sometimes called calcium sensitization. In addition to smooth muscle contraction, ROCKs have also been shown to be involved in cellular functions including apoptosis, cell migration, transcriptional activation, fibrosis, cytokinesis, inflammation, and cell proliferation. Moreover, in neurons, ROCK plays a critical role in the inhibition of axonal growth by myelin-associated inhibitory factors such as myelin-associated glycoprotein (MAG). ROCK-activity also mediates the collapse of growth cones in developing neurons. Both processes are thought to be mediated by ROCK-induced phosphorylation of substrates such as LIM kinase and myosin light chain phosphatase, resulting in increased contractility of the neuronal actin-myosin system.

Inhibitors of ROCKs have been suggested for use in the treatments of a variety of diseases. They include cardiovascular diseases such as hypertension, chronic and congestive heart failure, cardiac hypertrophy, restenosis, chronic renal failure, and atherosclerosis. In addition, because of its muscle relaxing properties, it is also suitable for asthma, male erectile dysfunctions, female sexual dysfunction, and over-active bladder syndrome. ROCK inhibitors have been shown to possess anti-inflammatory properties. Thus, they can be used as a treatment for neuroinflammatory diseases such as stroke, multiple sclerosis, Alzheimer's disease, Parkinson's disease, amyotrophic lateral sclerosis, and inflammatory pain, as well as other inflammatory diseases such as rheumatoid arthritis, irritable bowel syndrome, and inflammatory bowel disease. In addition, based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative (recovery) treatment of CNS disorders such as spinal cord injury, acute neuronal injury (stroke, traumatic brain injury), Parkinson's disease, Alzheimer's disease, and other neurodegenerative disorders. Since ROCK inhibitors reduce cell proliferation and cell migration, they could be useful in treating cancer and tumor metastasis. Furthermore, there is evidence suggesting that ROCK inhibitors suppress cytoskeletal rearrangement upon virus invasion, thus they also have potential therapeutic value in antiviral and anti-bacterial applications. ROCK inhibitors may also be useful for the treatment of insulin resistance and diabetes.

Pulmonary Arterial Hypertension (PAH) is a condition in which the pressure in the lung circulation increases, eventually causing heart failure and death. Although many causes and conditions are found to be associated with PAH, many of them share in common several fundamental pathophysiological features. One important feature among these processes is dysfunction of the endothelium, the internal cellular layer of all vessel walls, which is normally responsible for the production and metabolism of a large array of substances that regulate vessel tone and repair and inhibit clot formation. In the setting of PAH, endothelial dysfunction can lead to excessive production of deleterious substances and impaired production of protective substances. Whether this is the primary event in the development of PAH or part of a downstream cascade remains unknown, but in either case, it is an important factor in the progressive vasoconstriction and vascular proliferation that characterize the disease. Recent in vivo studies showed that the Rho GTPase/RhoA pathway and its downstream effectors, the Rho-kinases (ROCK-1 and ROCK-2), have an important role in PAH, due to their lasting effects on vasoconstriction and pulmonary cell proliferation leading to vascular remodeling (See, for example, Wang et al., Inhibition of RhoA/ROCK signaling pathway ameliorates hypoxic pulmonary hypertension via HIF-la-dependent functional TRPC channels, Toxicol Appl Pharmacol. 369: 60-72 (2019); Cantoni et al., Pharmacological characterization of a highly selective Rho kinase (ROCK) inhibitor and its therapeutic effects in experimental pulmonary hypertension, Eur J Pharmacol. 850:126-34; Zhuang et al., Fasudil preserves lung endothelial function and reduces pulmonary vascular remodeling in a rat model of end-stage pulmonary hypertension with left heart disease, Int J Mol Med. 42(3):1341-52 (2018)).

The present inventors have discovered novel heterocyclic compounds, which are inhibitors of ROCK activities. Such derivatives are useful in the treatment of disorders associated with inappropriate or dysregulated ROCK activities.

SUMMARY OF THE INVENTION

In a first aspect of the present invention, there is provided a compound of Formula (I):

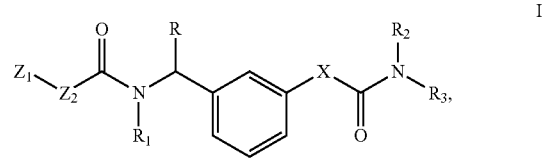

wherein $Z_1$ is OR', phenyl, naphthyl, or C5-C10 membered heterocycle, wherein the phenyl, naphthyl, or C5-C10 membered heterocycle is optionally substituted with H, halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, —C3-C7 cycloalkyl, or a 3- to 10-membered heterocycle, and wherein the —C1-C6 alkyl, aryl, —C3-C7 cycloalkyl, or 3- to 10-membered heterocycle is optionally substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, or —C3-C7 cycloalkyl;

$Z_2$ is phenyl, naphthyl, or C5-C10 membered heterocycle, wherein the phenyl, naphthyl, or C5-C10 membered heterocycle is optionally substituted with H, halo, —OH, —CN, —COOR', —OR', —OR'OR", —O(CH$_2$)$_2$NR'R", —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, —C3-C7 cycloalkyl, or a 3- to 10-membered heterocycle, and wherein the —C1-C6 alkyl, aryl, —C3-C7 cycloalkyl, or 3- to 10-membered heterocycle is optionally substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, or —C3-C7 cycloalkyl;

$R_1$ is H, —C1-C6 alkyl or —C3-C7 cycloalkyl, wherein the —C1-C6 alkyl or —C3-C7 cycloalkyl is optionally substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", or —S(O)$_2$R';

R is —C1-C6 alkyl, wherein the —C1-C6 alkyl is optionally substituted with one or more of the following: H, halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", or —S(O)$_2$R';

X is a bond or —OR$_4$, wherein R$_4$ is H, —C1-C6 alkyl or —C3-C7 cycloalkyl;

$R_2$ and $R_3$ are independently H, —C1-C6 alkyl, —C3-C7 cycloalkyl, aryl, C5-C10 membered heterocycle,

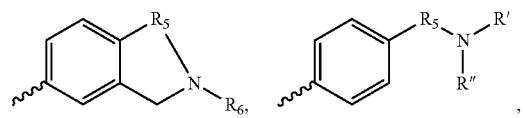

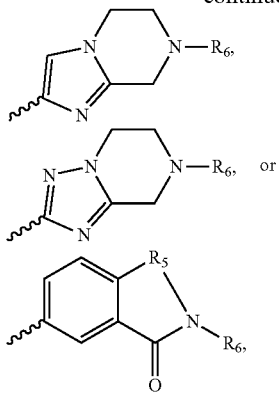

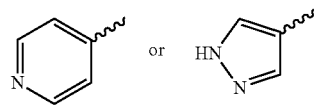

wherein the —C1-C6 alkyl, —C3-C7 cycloalkyl, aryl, C5-C10 membered heterocycle is optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, —C3-C7 cycloalkyl, or 3- to 11-membered heterocycle, wherein the —C1-C6 alkyl, aryl, —C3-C7 cycloalkyl, or 3- to 11-membered heterocycle is optionally substituted with one or more of the following: halo, —OH, —CN, —COOR', —CH$_2$NR'R", —OR', —OR'R", —SR', —OC(O)R', —NHR', —NR'R", —NHC(O)R', —NHC(O)NR'R", —C(O)NR'R", —NS(O)$_2$R', —S(O)$_2$NR'R", —S(O)$_2$ R', guanidino, nitro, nitroso, —C1-C6 alkyl, aryl, —C3-C7 cycloalkyl, and wherein R$_5$ is —C1-C6 alkyl, —OCH$_2$CH$_2$—NR$_6$CH$_2$CH$_2$—, —NC(O)CH$_2$CH$_2$—; R$_6$ is H, —C1-C6 alkyl or —C3-C7 cycloalkyl; and R' or R" is independently —H or —C1-C6 alkyl, or R' and R" together, optionally attaching to N or O atom, form a 4- to 8-membered cyclic structure.

In some non-limiting embodiments, Z$_1$ is an optionally substituted C5-C10 membered heterocycle. In certain non-limiting implementations, Z$_1$ is an optionally substituted pyridine, pyrimidine, pyrazole, imidazole, oxazole, thiazole, indazole or tetrazole. In further non-limiting implementations, Z$_1$ is an optionally substituted pyridine or pyrazole. The C5-C10 membered heterocycle, pyridine, pyrimidine, pyrazole, imidazole, oxazole, thiazole, indazole or tetrazole is optionally substituted with H, halo, —OH, —CN, —COOR', —OR', —SR', —OC(O)R', —NHR', —NR'R", —NHC(O)R', —NHC(O)NR'R", —C(O)NR'R", —NS(O)$_2$ R', —S(O)$_2$NR'R", —S(O)$_2$R', guanidino, nitro, nitroso, —C1-C6 alkyl, aryl, —C3-C7 cycloalkyl, or a 3- to 10-membered heterocycle, and wherein the —C1-C6 alkyl, aryl, —C3-C7 cycloalkyl, or 3- to 10-membered heterocycle is optionally substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, or —C3-C7 cycloalkyl.

In other non-limiting embodiments, Z$_1$ is an unsubstituted C5-C10 membered heterocycle. In certain non-limiting implementations, Z$_1$ is an unsubstituted pyridine, pyrimidine, pyrazole, imidazole, oxazole, thiazole, indazole or tetrazole. In further non-limiting implementations, Z$_1$ is an unsubstituted pyridine or pyrazole. In yet further non-limiting implementations, Z$_1$ is an unsubstituted In some embodiments, Z$_1$ is —OR', wherein R' is methyl (i.e., Z$_1$ is methoxy).

In some non-limiting embodiments, Z$_2$ is an optionally substituted C5-C10 membered heterocycle. In certain non-limiting implementations, Z$_2$ is an optionally substituted phenyl, pyridine, or pyrazole. The C5-C10 membered heterocycle, phenyl, pyridine, or pyrazole is optionally substituted with H, halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$ R', guanidino, nitro, nitroso, —C1-C6 alkyl, aryl, —C3-C7 cycloalkyl, or a 3- to 10-membered heterocycle. In further non-limiting implementations, Z$_2$ is a phenyl, pyridine or pyrazole optionally substituted with halo, —OR', —C1-C6 alkyl, —OR'OR", or —O(CH$_2$)$_2$NR'R", wherein the —C1-C6 alkyl is optionally substituted with one or more of —OR' or NR'R", and wherein the R' or R" are independently —H, methyl or ethyl. In yet further non-limiting implementations, Z$_2$ is phenyl substituted with halo, —OR', —C1-C6 alkyl, —OR'OR", or —O(CH$_2$)$_2$NR'R", wherein the —C1-C6 alkyl is optionally substituted with one or more of —OR' or NR'R", and wherein the R' or R" are independently —H, methyl or ethyl.

In other non-limiting embodiments, Z$_2$ is an unsubstituted C5-C10 membered heterocycle. In certain non-limiting implementations, Z$_2$ is an unsubstituted phenyl, pyridine, or pyrazole. In further non-limiting implementations, Z$_2$ is selected from the group consisting of:

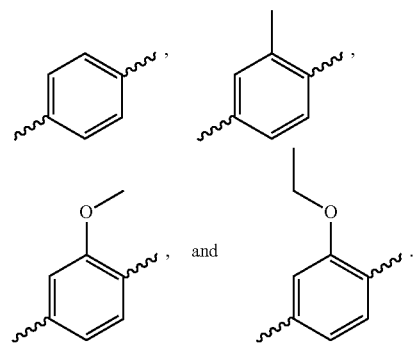

In some non-limiting embodiments, R$_1$ is a H, unsubstituted methyl, methoxyethyl or dimethylaminoethyl. In some non-limiting implementations, R$_1$ is H or

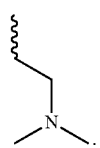

In some non-limiting embodiments, R is a methyl. In other non-limiting embodiments, R is hydroxymethyl and the compound has a structure of Formula (III):

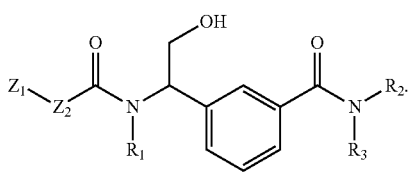

III

In further non-limiting implementations, R is a hydroxymethyl with S configuration or a methyl with R configuration.

In some non-limiting embodiments, X is a bond.

In other non-limiting embodiments, X is —OR₄, and the compound has a structure of Formula (II):

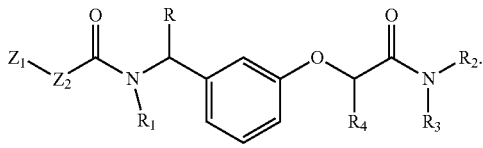

II

In some non-limiting embodiments, R₂ is H, and R₃ is H, —C1-C6 alkyl, —C3-C7 cycloalkyl, aryl, C5-C10 membered heterocycle,

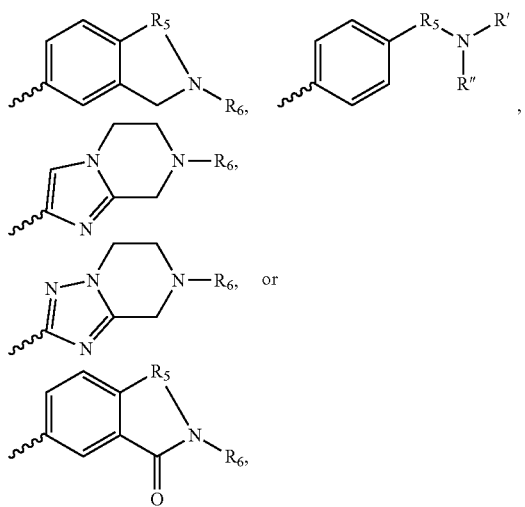

wherein the —C1-C6 alkyl, —C3-C7 cycloalkyl, aryl, C5-C10 membered heterocycle is optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)₂R', —S(O)₂NR'R", —S(O)₂R', guanidino, nitro, nitroso, —C1-C6 alkyl, aryl, —C3-C7 cycloalkyl, or 3- to 11-membered heterocycle, wherein the —C1-C6 alkyl, aryl, —C3-C7 cycloalkyl, or 3- to 11-membered heterocycle is optionally substituted with one or more of the following: halo, —OH, —CN, —COOR', —CH₂NR'R", —OR', —OR'R", —SR', —OC(O)R', —NHR', —NR'R", —NHC(O)R', —NHC(O)NR'R", —C(O)NR'R", —NS(O)₂R', —S(O)₂NR'R", —S(O)₂ R', guanidino, nitro, nitroso, —C1-C6 alkyl, aryl, —C3-C7 cycloalkyl, wherein R₅ is —C1-C6 alkyl, —OCH₂CH₂—, —NR₆CH₂CH₂—, —NC(O)CH₂CH₂—, and wherein R₆ is H, —C1-C6 alkyl or —C3-C7 cycloalkyl.

In certain non-limiting implementations, R₂ is H, and R₃ is —C3-C7 cycloalkyl or —C3-C7 cycloalkyl methyl, wherein the —C3-C7 cycloalkyl or —C3-C7 cycloalkyl methyl is optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)₂R', —S(O)₂NR'R", —S(O)₂R', guanidino, nitro, nitroso, —C1-C6 alkyl, aryl, —C3-C7 cycloalkyl, or 3- to 11-membered heterocycle.

In further non-limiting implementations, R₂ is H, and R₃ is O

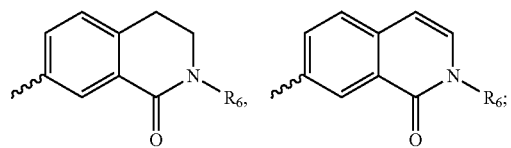

a —C3-C7 cycloalkyl selected from the group consisting of: cyclohexyl, cyclopentyl, cyclobutyl, cyclopropyl, cyclohexyl methyl, cyclopentyl methyl, cyclobutyl methyl, cyclopropyl methyl; an aryl selected from the group consisting of: phenyl and benzyl; or a C5-C10 membered heterocycle selected from the group consisting of: pyrrolidine-3-yl, piperidine-4-yl, (pyrrolidine-3-yl)methyl, (piperidine-4-yl)methyl, wherein the cyclohexyl, cyclopentyl, cyclobutyl, cyclopropyl, cyclohexyl methyl, cyclopentyl methyl, cyclobutyl methyl cyclopropyl methyl phenyl, benzyl, pyrrolidine-3-yl, piperidine-4-yl, (pyrrolidine-3-yl)methyl or (piperidine-4-yl)methyl is optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)₂R', —S(O)₂NR'R", —S(O)₂ R', guanidino, nitro, nitroso, —C1-C6 alkyl, aryl, —C3-C7 cycloalkyl, or 3- to 11-membered heterocycle. In yet further non-limiting implementations, R₂ is H, and R₃ is cyclopentyl or cyclohexyl.

In other non-limiting embodiments, R₂ and R₃ are independently H, —C3-C7 cycloalkyl, or —C3-C7 cycloalkyl methyl; wherein the —C3-C7 cycloalkyl or —C3-C7 cycloalkyl methyl is optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)₂R', —S(O)₂NR'R", —S(O)₂ R', guanidino, nitro, nitroso, —C1-C6 alkyl, aryl, —C3-C7 cycloalkyl, or a 3- to 11-membered heterocycle; with the proviso that R₂ and R₃ are not both H.

In certain non-limiting implementations, R₂ and R₃ are independently H, cyclohexyl, cyclopentyl, cyclobutyl, cyclopropyl, cyclohexyl methyl, cyclopentyl methyl, cyclobutyl methyl or cyclopropyl methyl; and R₂ and R₃ are independently optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)₂R', —S(O)₂NR'R", —S(O)₂R', guanidino, nitro, nitroso, —C1-C6 alkyl, aryl, —C3-C7 cycloalkyl, or a 3- to 11-membered heterocycle.

In other non-limiting implementations, R₂ and R₃ are independently H, phenyl, or benzyl; wherein the phenyl or benzyl is optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)₂R', —S(O)₂NR'R", —S(O)₂R', guanidino, nitro, nitroso, —C1-C6 alkyl, aryl, —C3-C7 cycloalkyl, or a 3- to 11-membered heterocycle; with the proviso that $R_2$ and $R_3$ are not both H.

In some embodiments, $R_1$, $R_2$, or both are H.

In certain non-limiting implementations, $Z_1$ is a pyridine or pyrazole; $Z_2$ is an unsubstituted phenyl, pyridine, or pyrazole, or a phenyl substituted with halo, —OR', —C1-C6 alkyl, —OR'OR", or —O(CH$_2$)$_2$NR'R", wherein the —C1-C6 alkyl is optionally substituted with one or more of —OR' or NR'R"; $R_1$ is H, unsubstituted methyl, or dimethylamine; X is a bond; $R_2$ is H; and the R' or R" is independently —H, methyl or ethyl.

In other non-limiting implementations, $Z_1$ is a pyridine, optionally substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, or —C3-C7 cycloalkyl; $Z_2$ is a C5-C10 membered heterocycle, optionally substituted with H, halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, —C3-C7 cycloalkyl, or a 3- to 11-membered heterocycle; $R_2$ and $R_3$ are independently H, phenyl, benzyl, —C3-C7 cycloalkyl, or —C3-C7 cycloalkyl methyl, wherein the phenyl, benzyl, —C3-C7 cycloalkyl or —C3-C7 cycloalkyl methyl is optionally substituted with H, halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, —C3-C7 cycloalkyl, or a 3 to 11-membered heterocycle; with the proviso that $R_2$ and $R_3$ are not both H.

In further embodiments, R is hydroxymethyl and the compound has a structure of Formula (IV):

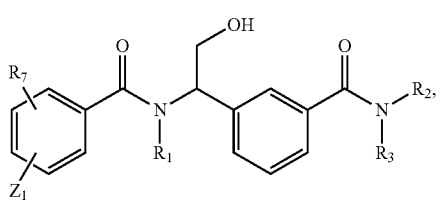

IV wherein $Z_1$ is -pyridine, -pyrimidine, -pyrazole, -imidazole, -oxazole, -thiazole, -indazole, or -tetrazole, wherein the -pyridine, -pyrimidine, -pyrazole, -imidazole, -oxazole, -thiazole, -indazole, or -tetrazole is unsubstituted or substituted with one or more of the following: -halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', -guanidino, -nitro, -nitroso, —C$_1$-C$_6$ alkyl, -aryl, —C$_3$-C$_7$ cycloalkyl, and a 3- to 10-membered heterocycle, and the —C$_1$-C$_6$ alkyl, -aryl, —C$_3$-C$_7$ cycloalkyl, or 3- to 10-membered heterocycle is unsubstituted or substituted with one or more of the following: -halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', -guanidino, -nitro, -nitroso, —C$_1$-C$_6$ alkyl, -aryl, and —C$_3$-C$_7$ cycloalkyl;

$R_1$ is —H, —C$_1$-C$_6$ alkyl, or —C$_3$-C$_7$ cycloalkyl, wherein the —C$_1$-C$_6$ alkyl or —C$_3$-C$_7$ cycloalkyl is unsubstituted or substituted with one or more of the following: -halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", and —S(O)$_2$R';

$R_2$ and $R_3$ are independently —H, —C$_1$-C$_6$ alkyl, —C$_3$-C$_7$ cycloalkyl, -aryl, a heterocycle comprising 5 to 10 carbons,

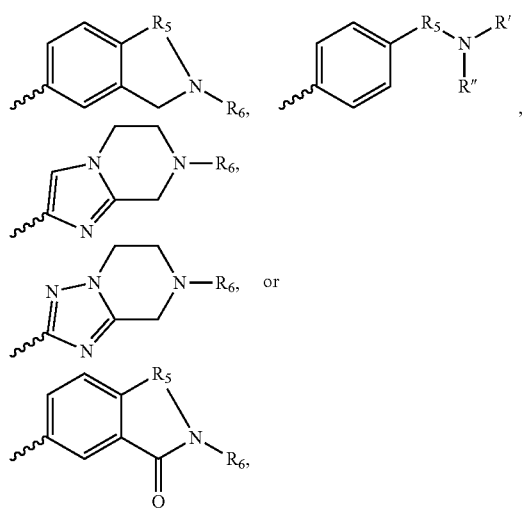

wherein the —C$_1$-C$_6$ alkyl, —C$_3$-C$_7$ cycloalkyl, -aryl, or heterocycle comprising 5 to 10 carbons is unsubstituted or substituted with one or more of the following: -halo, —OH, —CN, —CNR'R", —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', -guanidino, -nitro, -nitroso, —C$_1$-C$_6$ alkyl, aryl, —C$_3$-C$_7$ cycloalkyl, and 3- to 11-membered heterocycle, wherein the —C$_1$-C$_6$ alkyl, aryl, —C$_3$-C$_7$ cycloalkyl, or 3- to 11-membered heterocycle is unsubstituted or substituted with one or more of the following: -halo, —CNR'R", —OH, —CN, —COOR', —OR', —SR', —OC(O)R', —NHR', —NR'R", —NHC(O)R', —NHC(O)NR'R", —C(O)NR'R", —NS(O)$_2$R', —OR'OR", —S(O)$_2$NR'R", —S(O)$_2$R', -guanidino, -nitro, -nitroso, —C1-C6 alkyl, -aryl, and —C3-C7 cycloalkyl; $R_5$ is —C$_1$-C$_6$ alkyl, —OCH$_2$CH$_2$—, —NR$_6$CH$_2$CH$_2$—, or —NC(O)CH$_2$CH$_2$—, and $R_6$ is —H, —C$_1$-C$_6$ alkyl, or —C$_3$-C$_7$ cycloalkyl;

R' and R" are independently —H or —C$_1$-C$_6$ alkyl, or R' and R" together, optionally attached to N or O atom, form a 4- to 8-membered cyclic structure; and $R_7$ is —H, -halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$ R', —C$_1$-C$_6$ alkyl, —C$_3$-C$_7$ cycloalkyl, -aryl, or a heterocycle comprising 5 to 10 carbons, wherein the —C$_1$-C$_6$ alkyl, —C$_3$-C$_7$ cycloalkyl, -aryl, or heterocycle comprising 5 to 10 carbons is unsubstituted or substituted with -halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', -guanidino, -nitro, -nitroso, —C$_1$-C$_6$ alkyl, -aryl, —C$_3$-C$_7$ cycloalkyl, or 3- to 10-membered heterocycle.

In some implementations, at least one of the compound is selected from the group consisting of:

(2) 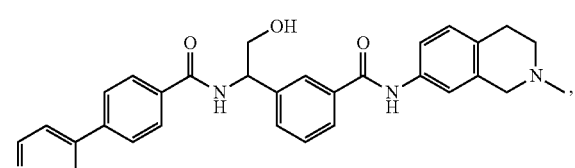
(6) 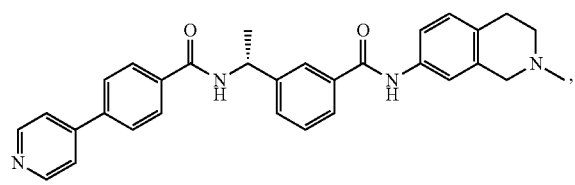
(7) 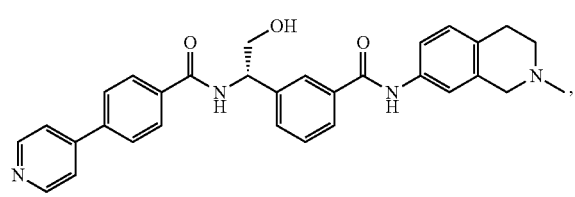
(8) 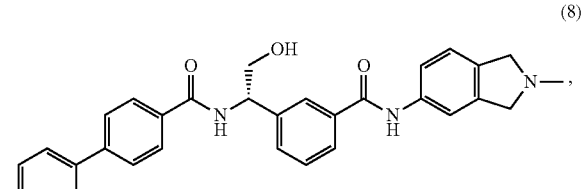
(9) 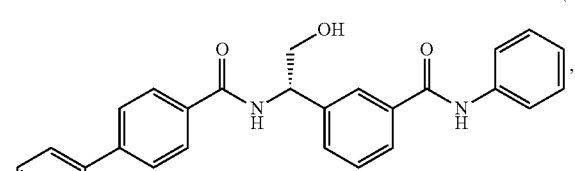
(10) 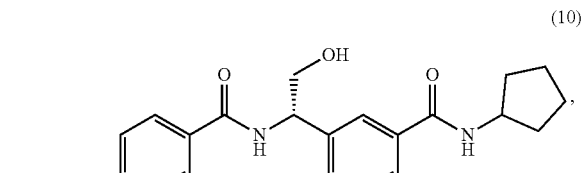
(11) 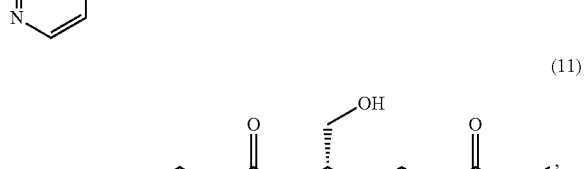
(12) 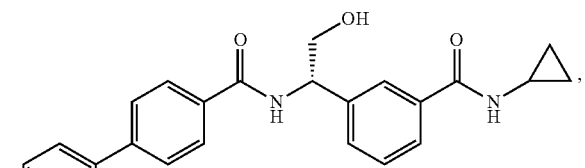
(13) 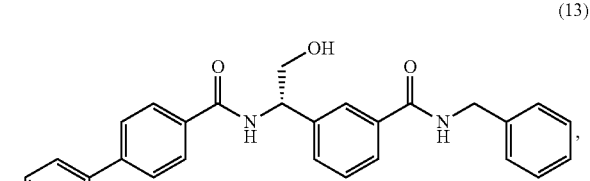
(14) 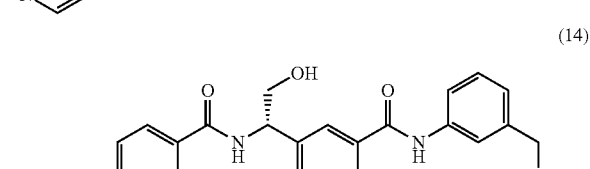
(15) 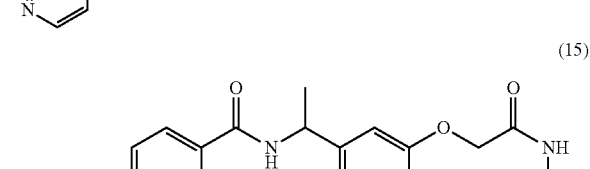
(16) 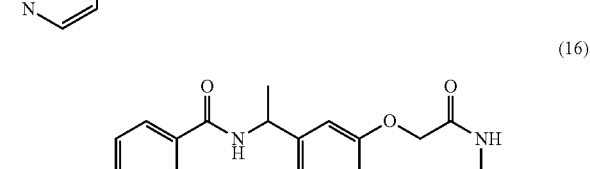
(20) 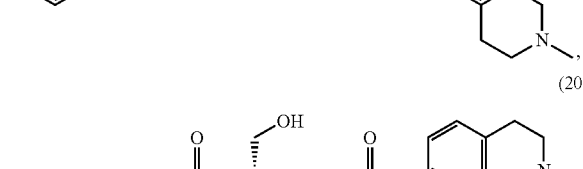
(21) 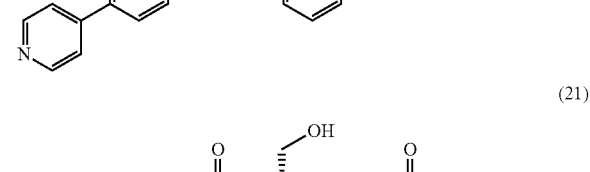

-continued (22), (23), (24), (25), (26), (27), (28), (29), (30), (31), (32), (33), (34)

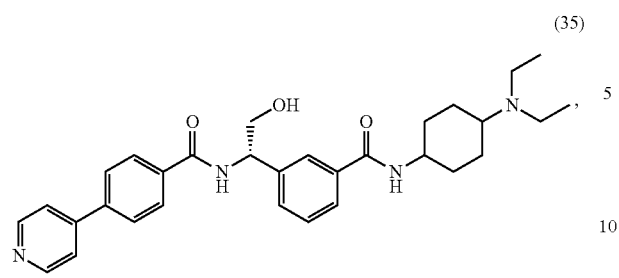
(35)
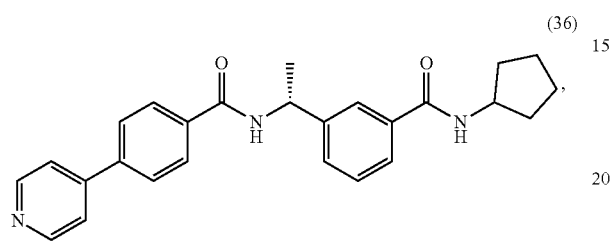
(36)
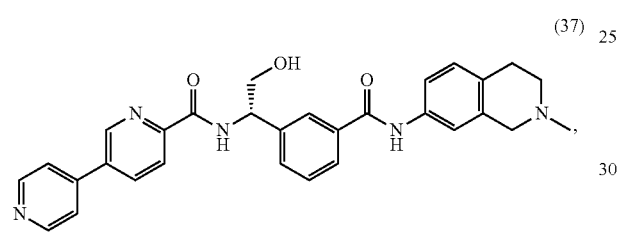
(37)
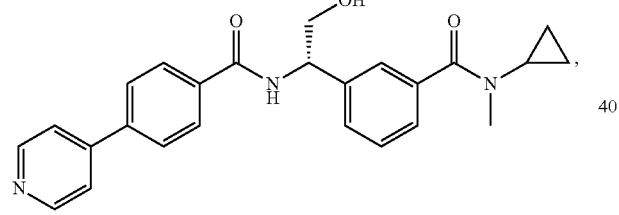
(38)
(39)
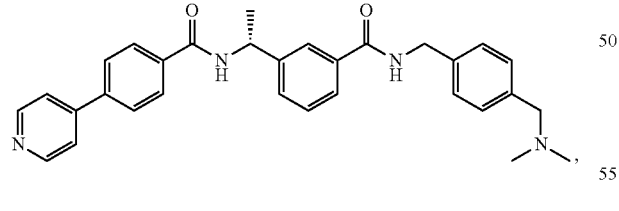
(40)
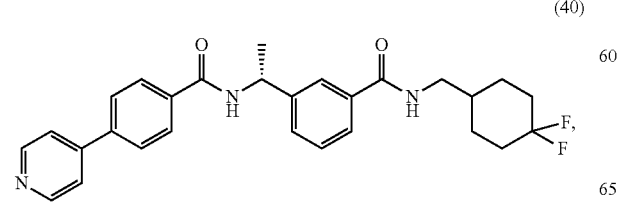
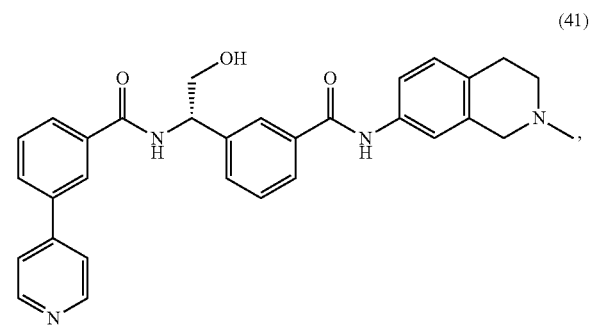
(41)
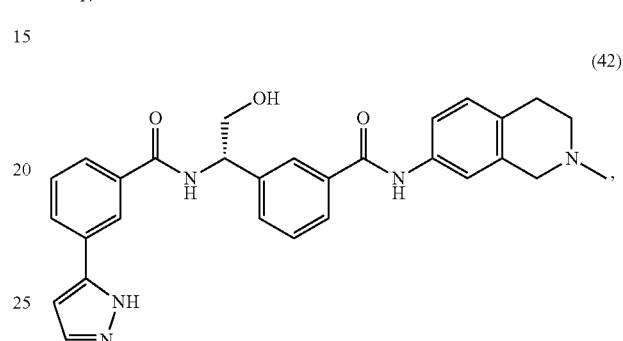
(42)
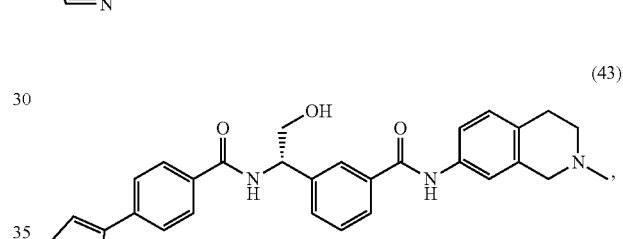
(43)
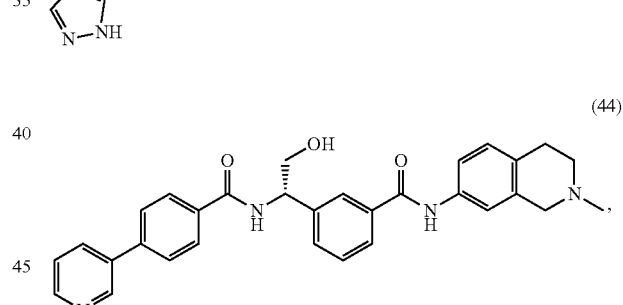
(44)
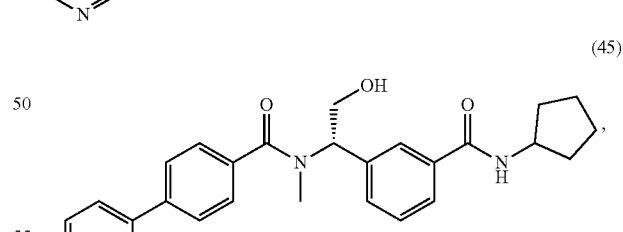
(45)
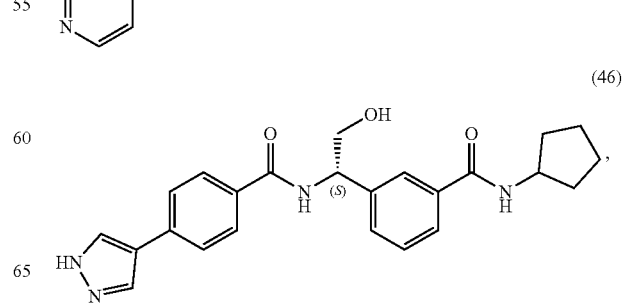
(46)

-continued

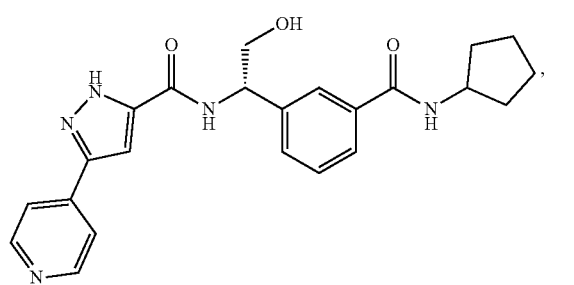
(61)
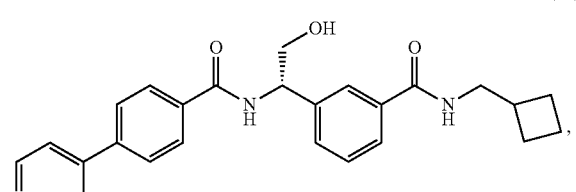
(66)
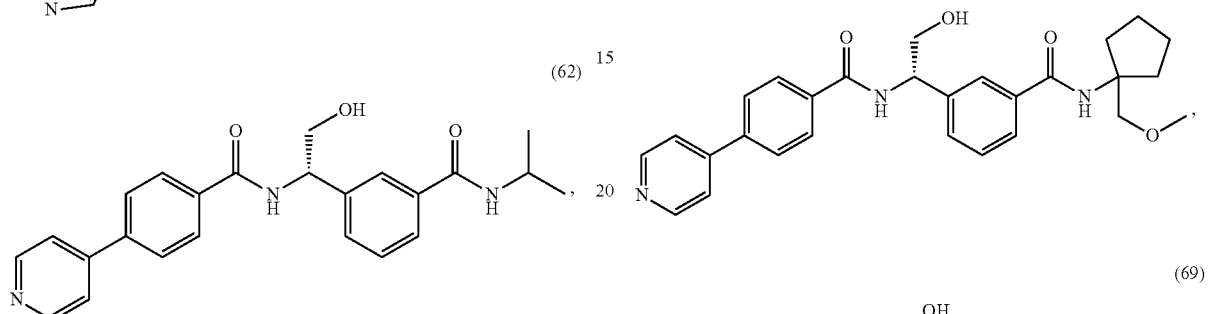
(62), (67), (69)
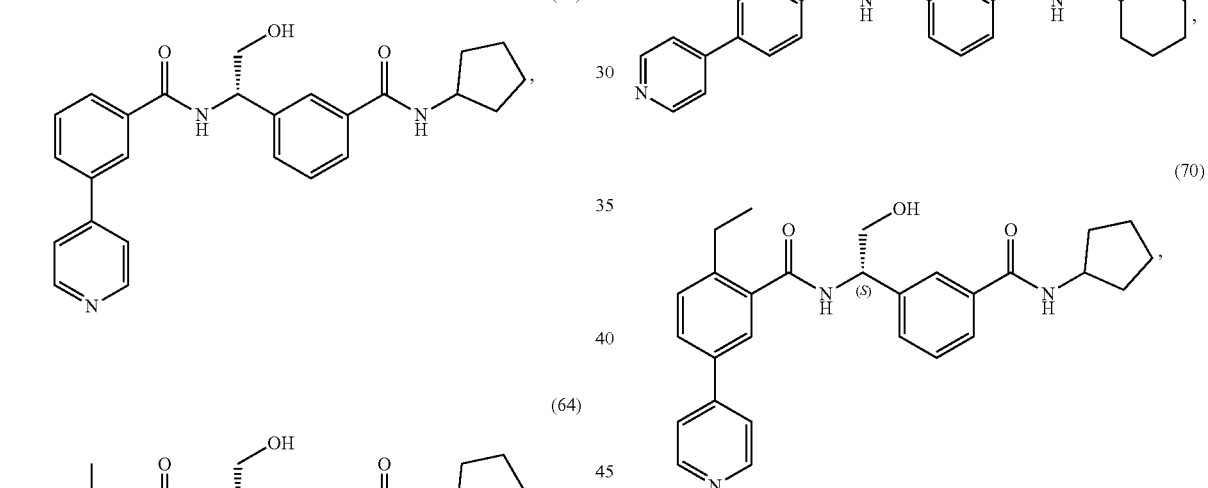
(63), (64), (70)
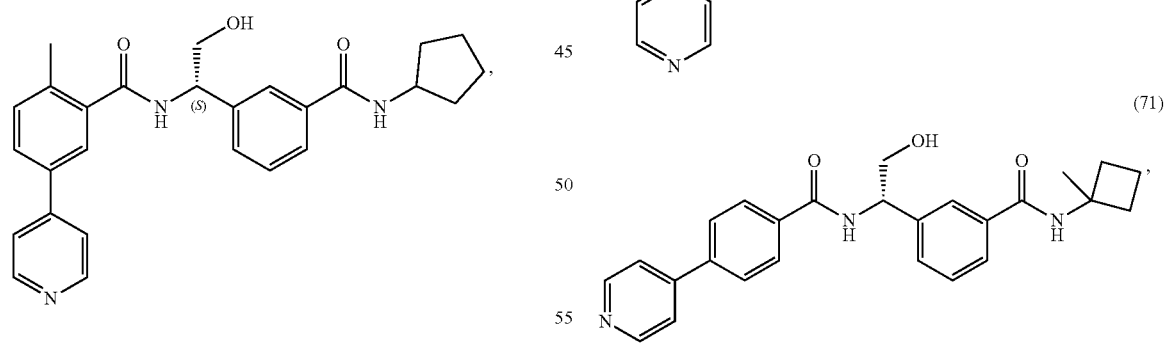
(65), (71)
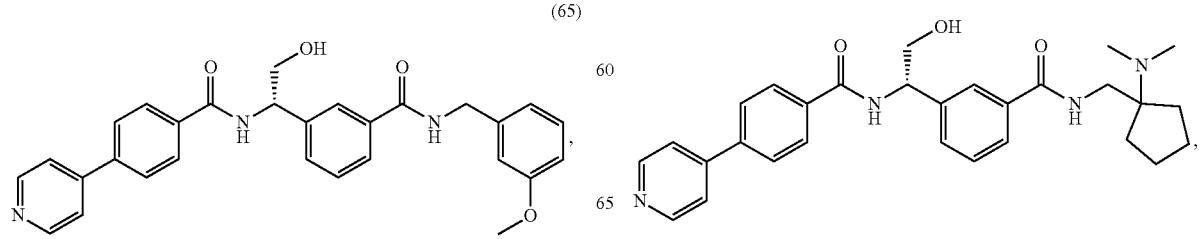
(72)

(73) 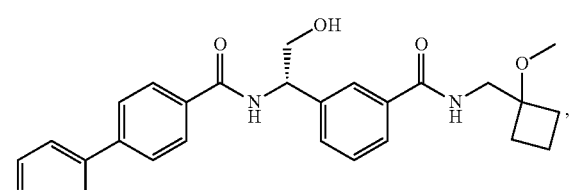
(74) 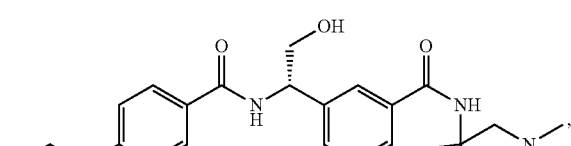
(75) 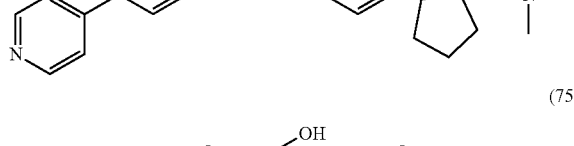
(76) 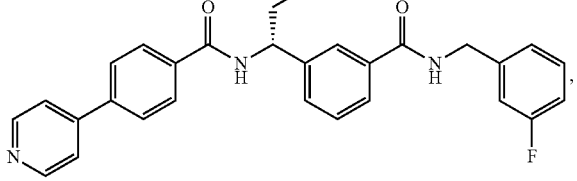
(77) 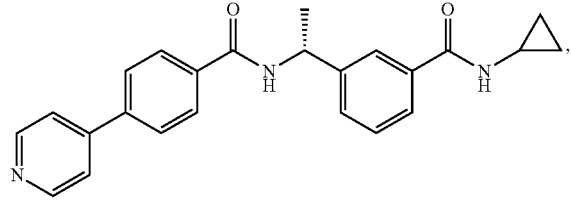
(78) 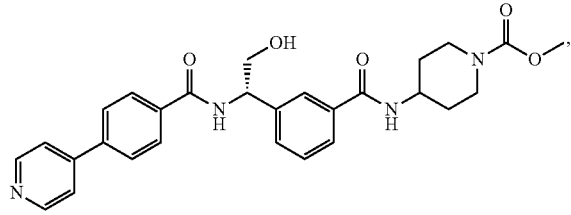
(79) 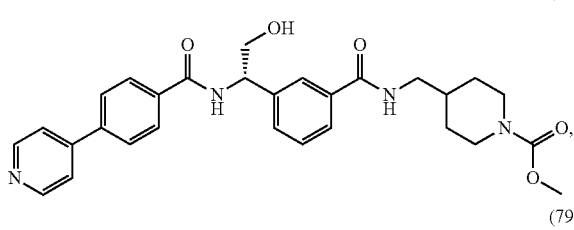
(80) 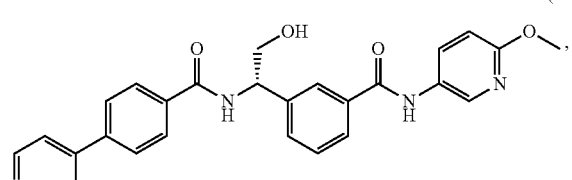
(81) 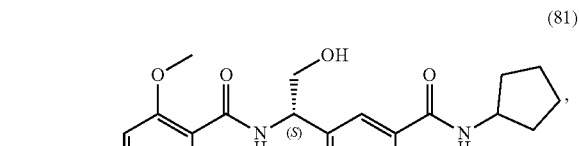
(82) 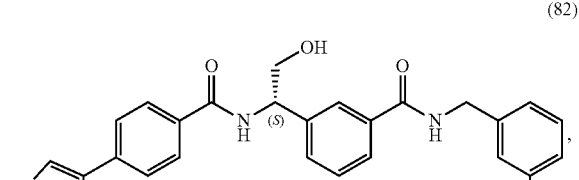
(83) 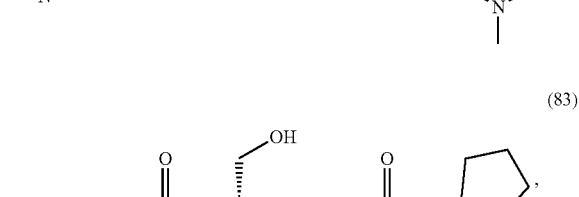
(84) 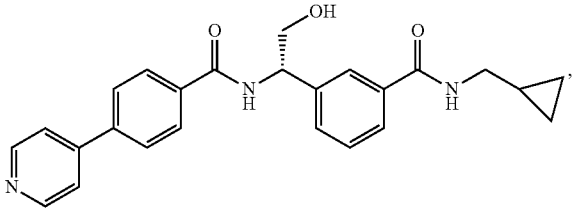
(85) 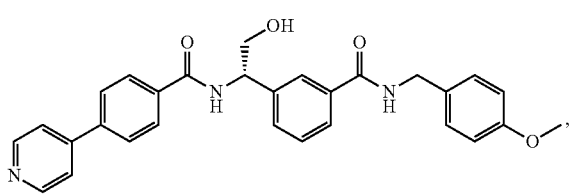

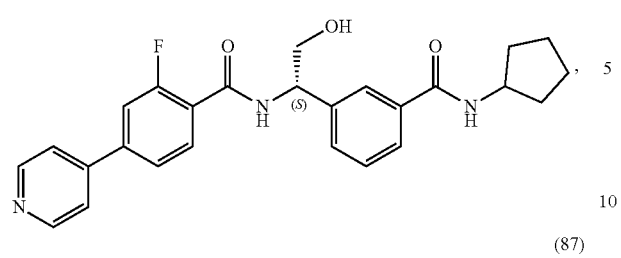
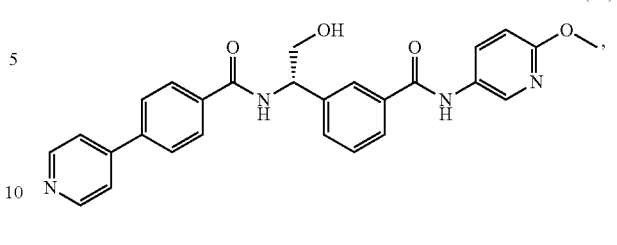
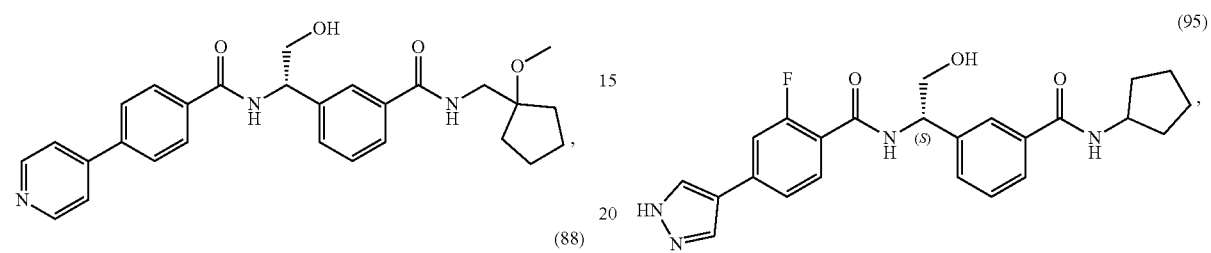
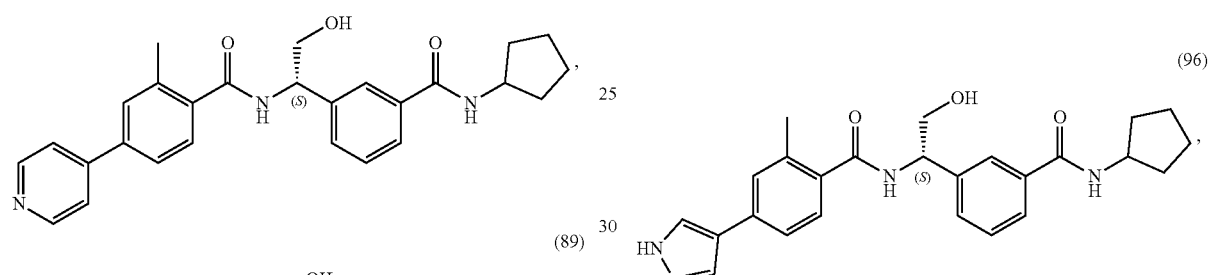
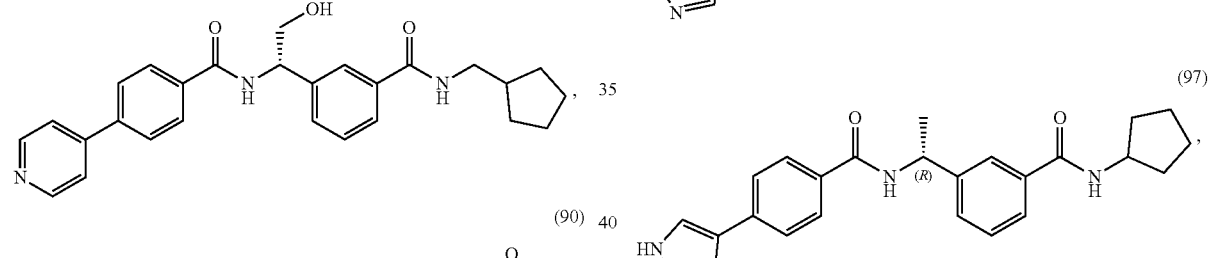
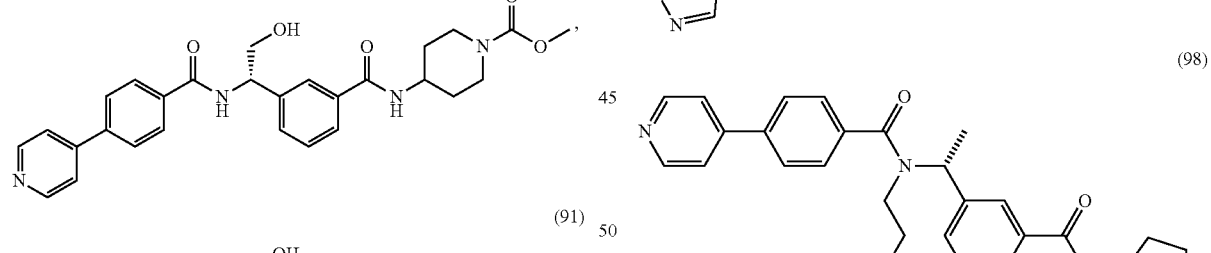
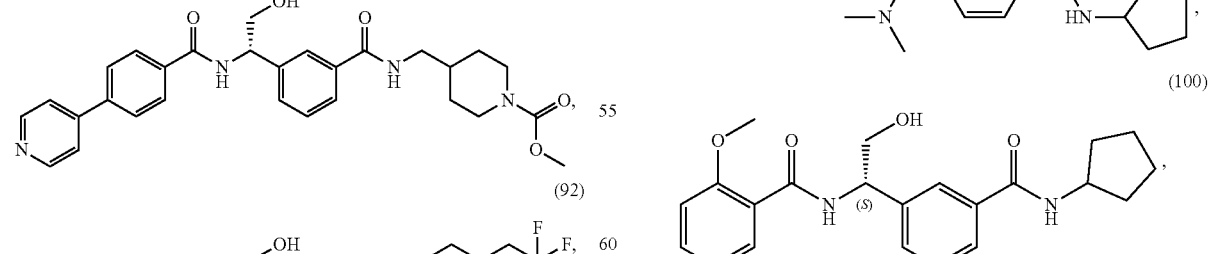
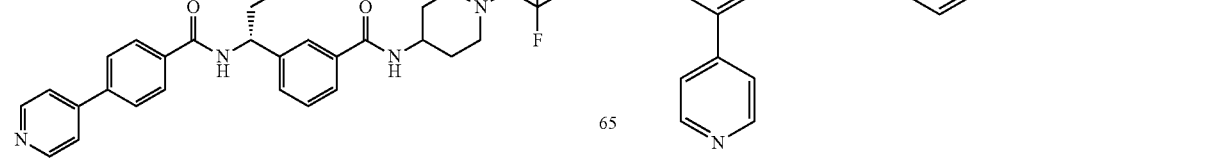

(101)
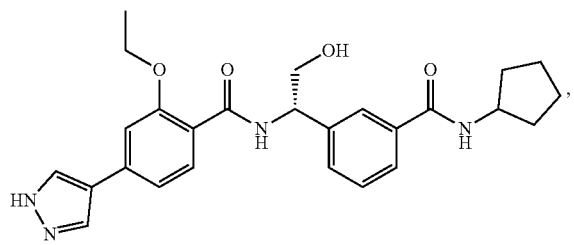
(102)
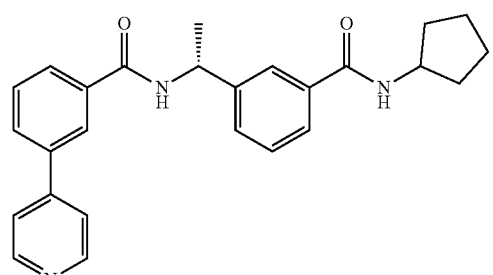
(103)
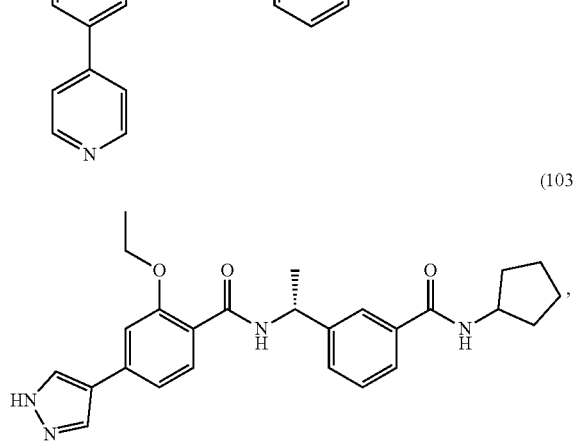
(104)
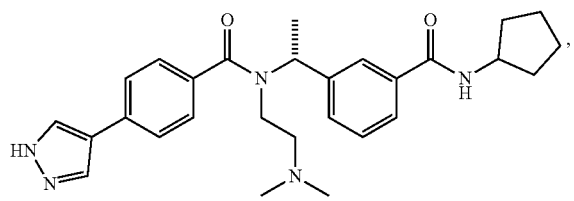
(105)
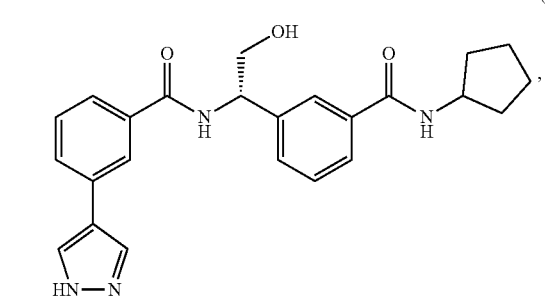
(106)
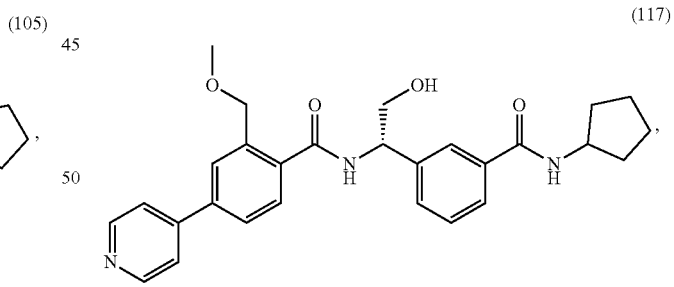
(110)
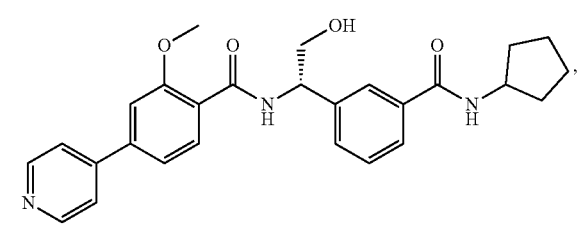
(113)
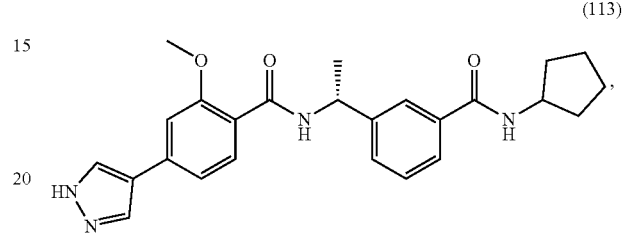
(115)
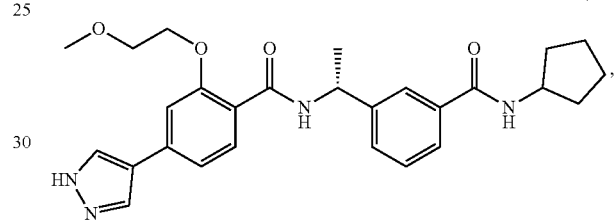
(116)
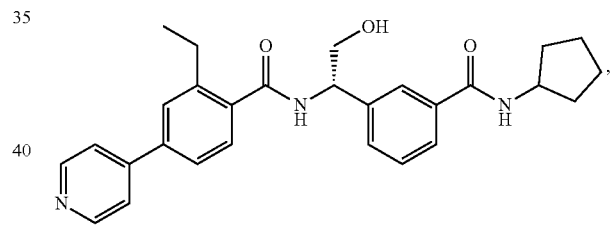
(117)
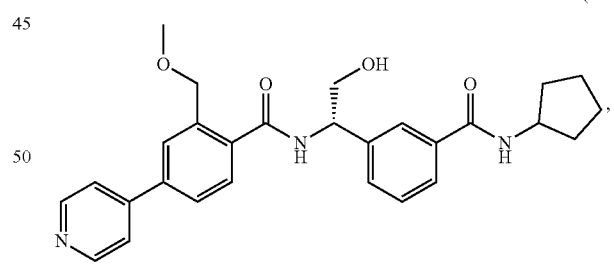
(118)
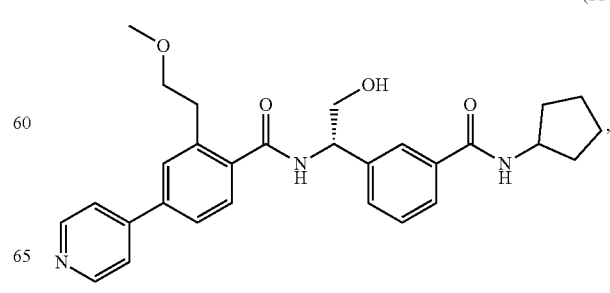

(119)
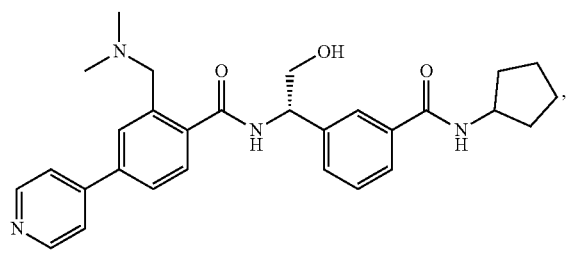
(124)
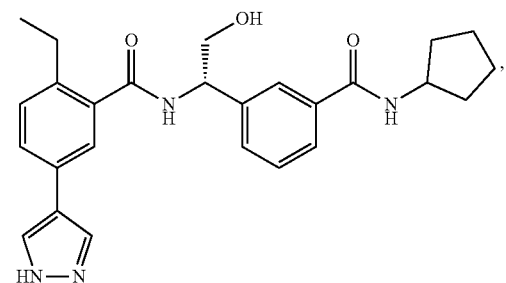
(120)
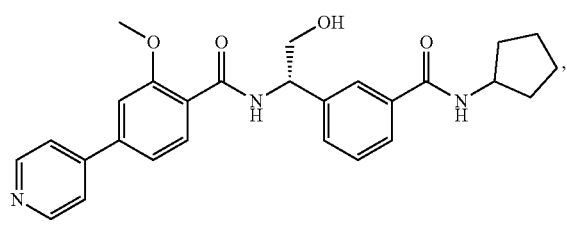
(125)
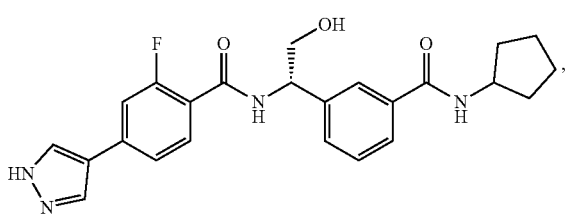
(121)
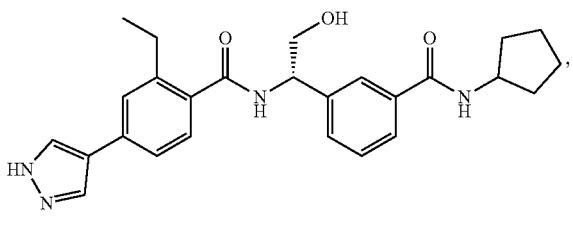
(126)
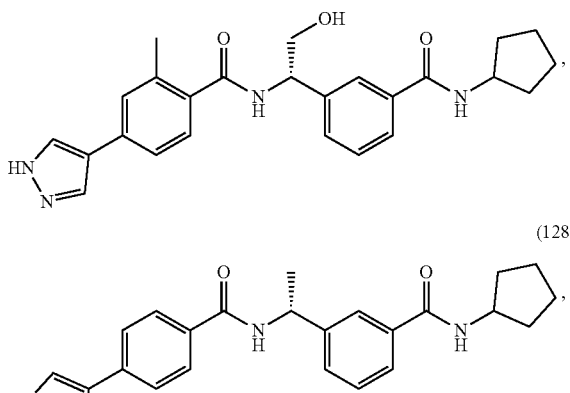
(122)
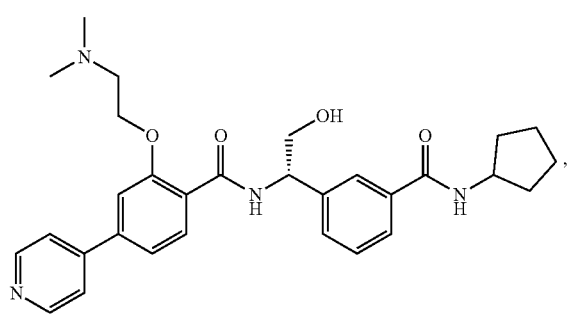
(127)
(128)
(123)
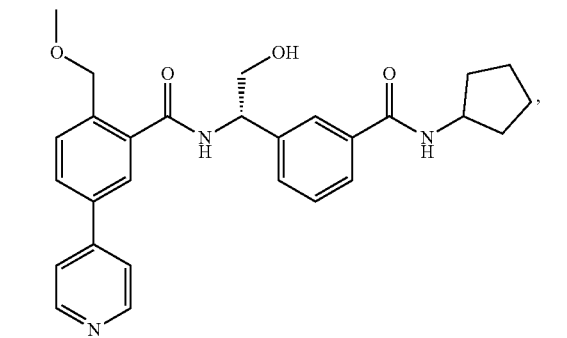
(129)
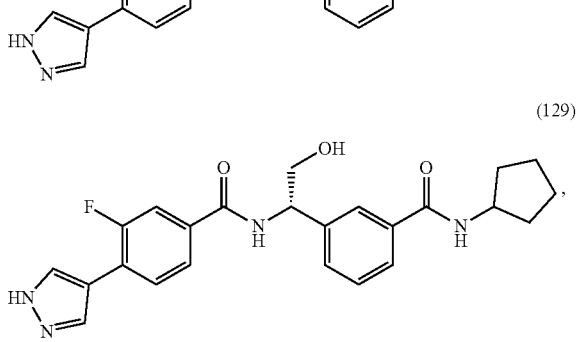

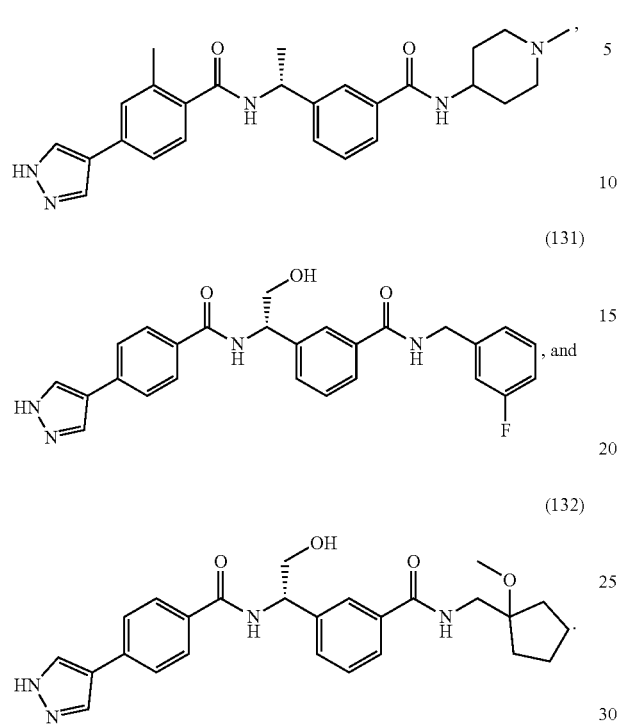
In other implementations, at least one of the compound is selected from the group consisting of:
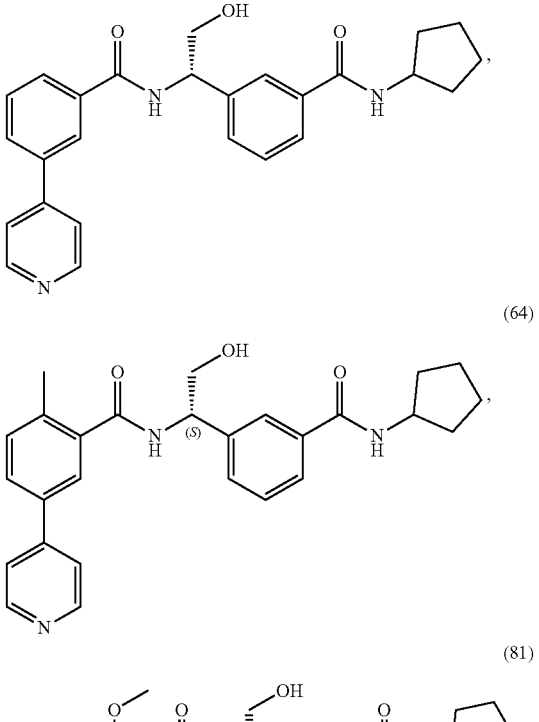
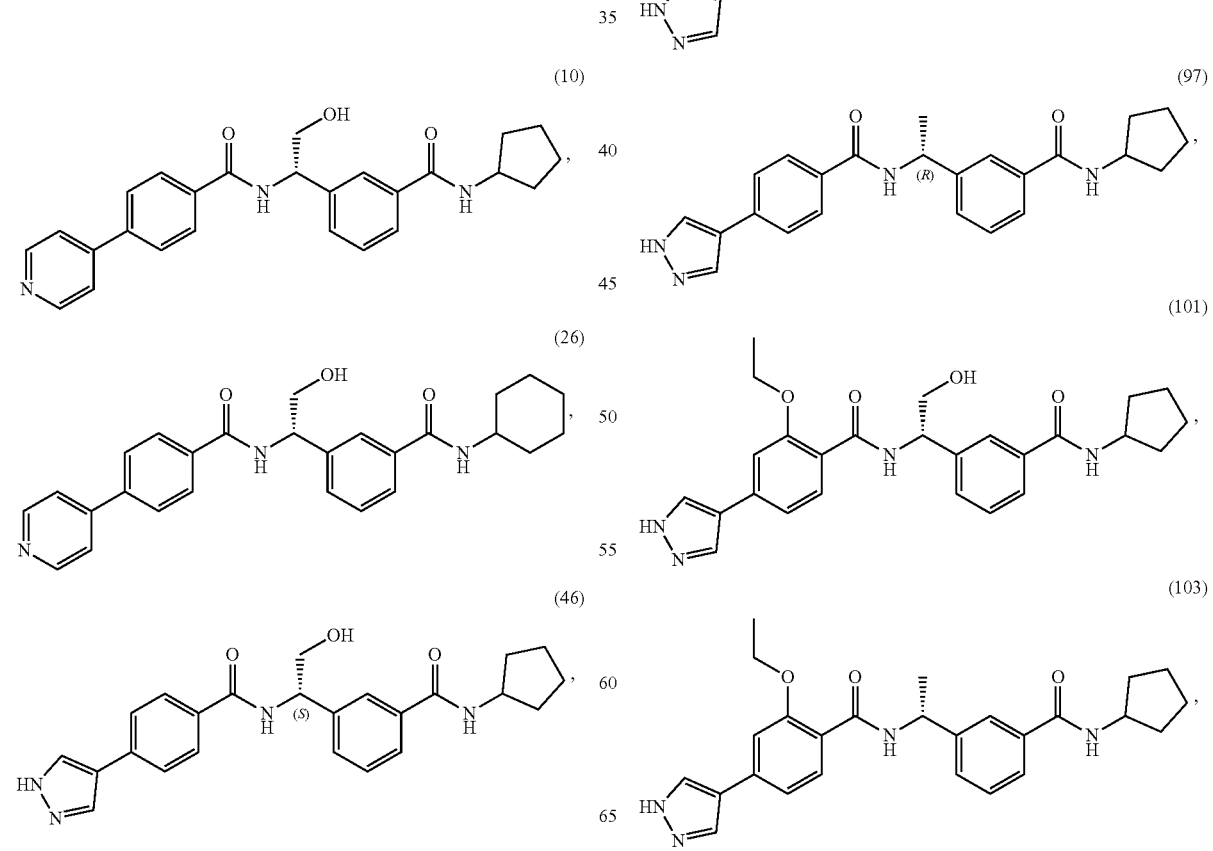

-continued

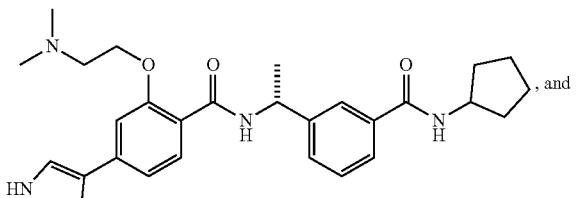
(105), and

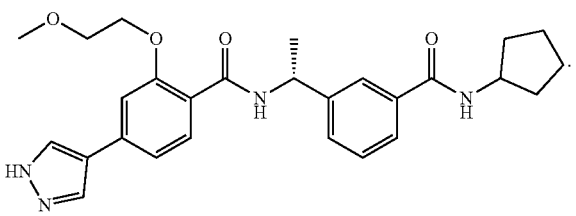
(115).

In a preferred non-limiting implementation, the compound consists of

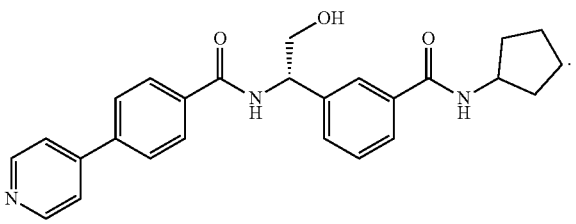
(10)

In another preferred non-limiting implementation, the compound consists of

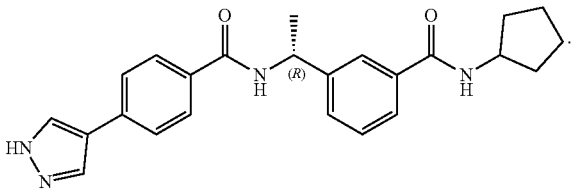
(97).

In a second aspect of the present invention, there is provided a pharmaceutical composition comprising a compound disclosed in the first aspect of the present invention, and a pharmaceutically acceptable carrier.

In a third aspect of the present invention, there is provided a method of inhibiting Rho-associated protein kinases, comprising administering to a subject in need thereof an effective amount of the compound of Formula I.

In a fourth aspect of the present invention, there is provided a composition comprising the compound of Formula I for use in inhibiting a Rho-associated protein kinase.

In a fifth aspect of the present invention, there is provided a use of a composition comprising the compound of Formula I in the manufacture of a medicament for inhibiting a Rho-associated protein kinase.

In a sixth aspect of the present invention, there is provided a method of treating a disease or improves a condition associated with modulation of Rho-associated protein kinases (e.g., ROCK-1, ROCK2, or both) in a subject in need thereof, comprising administering to the subject in need an effective amount of the compound of Formula I.

In a seventh aspect of the present invention, there is provided a composition comprising the compound of Formula I for use in treating or preventing a disease associated with Rho-associated protein kinase modulation.

In an eighth aspect of the present invention, there is provided a use of a composition comprising the compound of Formula I in the manufacture of a medicament for treating or preventing a disease associated with Rho-associated protein kinase modulation.

In some non-limiting embodiments, the compound or the (pharmaceutical) composition is capable of modulating or modulates the activity of Rho-associated protein kinases. In certain non-limiting implementations, modulating the activity of Rho-associated protein kinases comprises inhibiting the activity of Rho-associated protein kinases. In further non-limiting implementations, the Rho-associated protein kinases comprises ROCK-1, ROCK2, or both.

In some non-limiting embodiments, the (pharmaceutical) composition further comprises a pharmaceutically acceptable salt, hydrate, solvate, prodrug, stereoisomer, or tautomer thereof.

In some non-limiting embodiments, the disease is selected from the group consisting of: an arterial thrombotic disorder, cancer, a cardiovascular disease, a central nervous system disorder, glucose intolerance, a hematologic disease, a hematologic malignant neoplastic disorder, hyperinsulinemia, an infection, an inflammatory or autoimmune disease, insulin resistance, a metabolic syndrome, a neoplastic disease, a neurodegenerative disease, a neurodevelopmental disorder, an ocular disorder, osteoporosis, type 2 diabetes, a vascular smooth muscle dysfunction, and combinations thereof.

In certain non-limiting implementations, cancer is selected from the group consisting of: angioimmunoblastic T-cell lymphoma (AITL), breast cancer, cutaneous T-cell lymphoma (CTCL), hepatocellular cancer, gastric cancers, leukemia, lung cancer, lymphoma, multiple myeloma, ovarian cancer, pancreatic cancer, melanoma, amoeboid cancer cells, cancer characterized by amoeboid-like migration, peripheral T-cell lymphoma (PTCL), prostate cancer, renal cancer, and combinations thereof. In some implementations, gastric cancer comprises rhoA-mutated gastric cancer.

In other non-limiting implementations, the neurodegenerative disease is selected from the group consisting of: Alzheimer's, Amyotrophic Lateral Sclerosis, Huntington's, Parkinson's, spinal muscular atrophy, and combinations thereof.

In yet other non-limiting implementations, the neurodevelopmental disorder comprises Rett syndrome, Niemann-Pick type C, or both.

In further non-limiting implementations, the inflammatory or autoimmune disease is selected from the group consisting of: asthma, cardiovascular inflammation, renal inflammation, arteriosclerosis, rheumatoid arthritis, spondylitis arthritis, psoriatic arthritis, psoriasis, atopic dermatitis, eczema, multiple sclerosis, systemic lupus erythematosus, inflammatory bowel diseases, Crohn's disease, graft versus host disease, transplant rejection, a fibrotic disorder, and combinations thereof. In a preferred non-limiting implementation, the fibrotic disorder is selected from the group consisting of: liver fibrosis, lung fibrosis, skin fibrosis, cardiac fibrosis, kidney fibrosis, and combinations thereof. In a further preferred non-limiting implementation, the fibrotic disorder comprises lung fibrosis. In a yet further preferred non-limiting implementation, the lung fibrosis comprises idiopathic pulmonary fibrosis.

In certain implementations, the cardiovascular disease or vascular smooth muscle dysfunction is selected from the group consisting of: atherosclerosis, cardiac hypertrophy, cardiovascular stress, cerebral ischemia, cerebral vasospasm, chronic ischemia, erectile dysfunction, heart failure, hypertension, infarction-reperfusion injury, ocular hypertension, peripheral artery disease, pressure overload, restenosis, and combinations thereof.

In some non-limiting embodiments, the disease associated with Rho-associated protein kinase modulation comprises a hematologic malignant neoplastic disorder. In some non-limiting implementations, the method further comprises identifying the subject in need of therapy for the hematologic malignant neoplastic disorder.

In some non-limiting embodiments, the hematologic malignant neoplastic disorder is selected from the group consisting of: acute lymphocytic leukemia (ALL), acute myeloid leukemia (AML), acute promyelocytic leukemia (APL), acute undifferentiated leukemia (AUL), adult T-cell ALL, AML with trilineage myelodysplasia (AMLITMDS), anaplastic large-cell lymphoma (ALCL), chronic lymphocytic leukemia (CLL), chronic myeloid leukemia (CML), chronic neutrophilic leukemia (CNL), essential thrombocytosis (ET) and primary myelofibrosis (MF), Hodgkin's disease, juvenile myelomonocytic leukemia (JMML), leukemia, mixed lineage leukemia (MLL), multiple myeloma (MM), myelodysplastic syndrome (MDS), myeloma, myeloproliferative disease, myeloproliferative neoplasms (MPN), a disease category that includes polycythemia vera (PV), prolymphocytic leukemia (PML), and combinations thereof. In other embodiments, the hematologic malignant neoplastic disorder is characterized by deregulated FLT3 receptor tyrosine kinase activity.

In some non-limiting embodiments, the ocular disorder is selected from the group consisting of: ocular hypertension, age related macular degeneration (AMD), choroidal neovascularization (CNV), diabetic macular edema (DME), iris neovascularization, uveitis, glaucoma, retinitis of prematurity (ROP), and combinations thereof. In some implementations, glaucoma is selected from the group consisting of: primary open-angle glaucoma, acute angle-closure glaucoma, pigmentary glaucoma, congenital glaucoma, normal tension glaucoma, secondary glaucoma, neo vascular glaucoma, and combinations thereof.

In some non-limiting embodiments, the disease associated with modulation of Rho-associated protein kinases is selected from the group consisting of: a hematologic malignant neoplastic disorder characterized by deregulated FLT3 receptor tyrosine kinase activity, the ocular disorder, and a combination thereof.

In some preferred non-limiting implementations, the disease associated with modulation of Rho-associated protein kinases is selected from the group consisting of: gastric cancer, pancreatic cancer, melanoma, amoeboid cancer cells, cancer characterized by amoeboid-like migration, graft-versus-host disease (GVHD), psoriasis, glaucoma, primary myelofibrosis (MF), liver fibrosis, and idiopathic pulmonary fibrosis.

In other preferred non-limiting implementations, the disease associated with modulation of Rho-associated protein kinases is selected from the group consisting of: rhoA-mutated gastric cancer, idiopathic pulmonary fibrosis, and a combination thereof.

DETAILED DESCRIPTION

As used herein, the article "a" or "an" refers to one or more than one (e.g., at least one) of the grammatical object of the article. By way of example, "an element" means one element or more than one element.

As used herein, the term "and/or" refers to either "and" or "or" unless indicated otherwise.

As used herein, the term "optionally substituted" refers to that a given chemical moiety (e.g., an alkyl group) can (but is not required to) be bonded other substituents (e.g., heteroatoms). For instance, an alkyl group that is optionally substituted can be a fully saturated alkyl chain (e.g., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups.

As used herein, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$ alkyl, —C$C_6$ alkyl, —O$C_2$-$C_6$ alkenyl, —O$C_2$-$C_6$ alkynyl, —$C_2$-$C_6$ alkenyl, —$C_2$-$C_6$ alkynyl, —OH, —OP(0)(OH)$_2$, —OC(0)Ci-$C_6$ alkyl, —C(0)Ci-$C_6$ alkyl, —OC(0)OCi-$C_6$ alkyl, —H$_2$, —H(Ci-$C_6$ alkyl), —N(Ci-$C_6$ alkyl)$_2$, —S(O)$_2$—Ci-$C_6$ alkyl, —S(0) HCi-$C_6$ alkyl, and —S(O)N(Ci-$C_6$ alkyl)$_2$. The substituents can themselves be optionally substituted. Furthermore, when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 24 ring atoms or a polycyclic aromatic radical, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4] thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c] [1,2,5]thiadiazolyl, benzo[c] [1,2,5]oxadiazole, 1,3-dihydro-2H-benzo[d]imidazol-2-one, 3,4-dihydro-2H-pyrazolo, [1,5-b][1,2] oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof.

Furthermore, when containing two fused rings the heteroaryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuran, indolinyl, indolyl, and dihydrobenzoxanyl.

As used herein, the term "alkyl" refers to a straight or branched chain saturated hydrocarbon. Ci-C$_6$ alkyl groups contain 1 to 6 carbon atoms. Non-limiting examples of a Ci-C$_6$ alkyl group include: methyl, ethyl, propyl, butyl, pentyl, isopropyl, isobutyl, sec-butyl, tert-butyl, isopentyl, and neopentyl.

As used herein, the term "alkenyl" refers to an aliphatic hydrocarbon group containing a carbon-carbon double bond and which may be straight or branched having about 2 to about 6 carbon atoms in the chain. Alkenyl groups can have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A C$_2$-C$_6$ alkenyl group is an alkenyl group containing between 2 and 6 carbon atoms.

As used herein, the term "alkynyl" refers to an aliphatic hydrocarbon group containing a carbon-carbon triple bond and which may be straight or branched having about 2 to about 6 carbon atoms in the chain. Alkynyl groups can have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A C$_2$-C$_6$ alkynyl group is an alkynyl group containing between 2 and 6 carbon atoms.

As used herein, the term "cycloalkyl" refers to monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A C$_3$—C$_5$ cycloalkyl is a cycloalkyl group containing between 3 and 8 carbon atoms. A cycloalkyl group can be fused (e.g., decalin) or bridged (e.g., norbornane).

As used herein, the term "cycloalkenyl" refers to monocyclic, non-aromatic unsaturated carbon rings containing 3-18 carbon atoms. Examples of cycloalkenyl groups include, without limitation, cyclopentenyl, cyclohexenyl, cycloheptenyl, cyclooctenyl, and norborenyl. A C$_3$-C$_5$ cycloalkenyl is a cycloalkenyl group containing between 3 and 8 carbon atoms.

As used herein, the term "heterocyclyl," "heterocycloalkyl," or "heterocycle" refers to monocyclic or polycyclic 3 to 24-membered rings containing carbon and heteroatoms taken from oxygen, nitrogen, or sulfur and wherein there is not delocalized nt electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heterocyclyl or heterocycloalkyl ring can also be fused or bridged, e.g., can be a bicyclic ring.

The term "carbonyl" refers to a functional group composing a carbon atom double-bonded to an oxygen atom. It can be abbreviated herein as "oxo," as C(O), or as C=O.

"Spirocycle" or "spirocyclic" means carbogenic bicyclic ring systems with both rings connected through a single atom. The ring can be different in size and nature, or identical in size and nature. Examples include spiropentane, spirohexane, spiroheptane, spirooctane, spirononane, or spirodecane. One or both of the rings in a spirocycle can be fused to another ring carbocyclic, heterocyclic, aromatic, or heteroaromatic ring. One or more of the carbon atoms in the spirocycle can be substituted with a heteroatom (e.g., O, N, S, or P). A C3-C$_{12}$ spirocycle is a spirocycle containing between 5 and 12 carbon atoms. One or more of the carbon atoms can be substituted with a heteroatom.

The term "spirocyclic heterocycle" or "spiroheterocycle" is understood to mean a spirocycle wherein at least one of the rings is a heterocycle (e.g., at least one of the rings is furanyl, morpholinyl, or piperadinyl).

As used herein, halo groups include any halogen. Non-limiting examples include —F, —Cl, —Br, or —I.

A —C$_1$-C$_6$ alkyl group includes any straight or branched, saturated or unsaturated, substituted or unsubstituted hydrocarbon comprised of between one and six carbon atoms. Non-limiting examples of —C$_1$-C$_6$ alkyl groups include methyl, ethyl, propyl, isopropyl, butyl, sec-butyl, tert-butyl, pentyl, isopentyl, neopentyl, hexyl, isohexyl, neohexyl, ethylenyl, propylenyl, 1-butenyl, 2-butenyl, 1-pentenyl, 2-pentenyl, 1-hexenyl, 2-hexenyl, 3-hexenyl, acetylenyl, pentynyl, 1-butynyl, 2-butynyl, 1-pentynyl, 2-pentynyl, 1-hexynyl, 2-hexynyl and 3-hexynyl groups. Substituted —C$_1$-C$_6$ alkyl groups may include any applicable chemical moieties. Non-limiting examples of groups that may be substituted onto any of the above listed —C$_1$-C$_6$ alkyl groups include: halo, —C$_1$-C$_6$ alkyl, —O—(C$_1$-C$_6$ alkyl), C$_3$-C$_7$ cycloalkyl, —OH, —CN, —COOR', —OC(O)R', —NHR', N(R')$_2$, —NHC(O)R' or —C(O)NHR' groups. The groups denoted R' above may be —H, any —C$_1$-C$_6$ alkyl, or two R' may, optionally with a nitrogen or an oxygen atom which they are bound to, form a 3-, 4-, 5-, 6-, 7-membered ring system when the substitution is —N(R')$_2$.

An aryl group includes any unsubstituted or substituted phenyl or napthyl group. Non-limiting examples of groups that may be substituted onto an aryl group include: halo, —C$_1$-C$_6$ alkyl, —O—(C$_1$-C$_6$ alkyl), —OH, —CN, —COOR', —OC(O)R', NHR', N(R')$_2$, —NHC(O), R', or —C(O)NEtR'. The group denoted R' may be —H or any —C$_1$-C$_6$ alkyl.

A $C_3$-$C_7$ cycloalkyl group includes any 3-, 4-, 5-, 6-, or 7-membered substituted or unsubstituted non-aromatic carbocyclic ring. Non-limiting examples of $C_3$-$C_7$ cycloalkyl groups include: cyclopropyl, cyclobutyl, cyclopentyl, cyclopentadienyl, cyclohexyl, cyclohexenyl, cycloheptyl, cycloheptanyl, 1,3-cyclohexadienyl, 1,4-cyclohexadienyl, 1,3-cycloheptadienyl, and 1,3,5-cycloheptatrienyl groups. Non-limiting examples of groups that may be substituted onto $C_3$-$C_7$ cycloalkyl groups include: -halo, —$C_1$-$C_6$ alkyl, —O—($C_1$-$C_6$ alkyl), —OH, —CN, —COOR', —OC(O) R', NHR', N(R')$_2$, —NHC(O)R' or —C(O)NHR' groups. The groups denoted R' above include an —H or any unsubstituted —$C_1$-$C_6$ alkyl, examples of which are listed above. Halo groups include any halogen. Non-limiting examples include —F, —Cl, —Br, or —I.

A heterocycle may be any optionally substituted saturated, unsaturated or aromatic cyclic moiety wherein said cyclic moiety is interrupted by at least one heteroatom selected from oxygen (O), sulfur (S) or nitrogen (N). Heterocycles may be monocyclic or polycyclic rings. For example, suitable substituents include halogen, halogenated C1-6 alkyl, halogenated C1-6 alkoxy, amino, amidino, amido, azido, cyano, guanidino, hydroxyl, nitro, nitroso, urea, OS(O)$_2$R; OS(O)$_2$OR, S(O)$_2$OR S(O)$_{0-2}$R, C(O)OR wherein R may be H, $C_1$-$C_6$ alkyl, aryl or 3 to 10 membered heterocycle) OP(O)OR$_1$OR$_2$, P(O)OR$_1$OR$_2$, SO$_2$NR$_1$R$_2$, NR$_1$SO$_2$R$_2$C(R$_1$)NR$_2$C(R$_1$)NOR$_2$, R$_1$ and R$_2$ may be independently H, $C_1$-$C_6$ alkyl, aryl or 3 to membered heterocycle), NR$_1$C(O)R$_2$, NR$_1$C(O)OR$_2$, NR$_3$C(O)NR$_2$R$_1$, C(O)NR$_1$R$_2$, OC(O)NR$_1$R$_2$. For these groups, R$_1$, R$_2$ and R$_3$ are each independently selected from H, $C_1$-$C_6$ alkyl, aryl or 3 to 10 membered heterocycle or R$_1$ and R$_2$ are taken together with the atoms to which they are attached to form a 3 to 10 membered heterocycle.

Possible substituents of heterocycle groups include halogen (Br, Cl, I or F), cyano, nitro, oxo, amino, C1-4 alkyl (e.g., CH$_3$, C$_2$H$_5$, isopropyl) $C_{1-4}$ alkoxy (e.g., OCH$_3$, OC$_2$H$_5$), halogenated $C_{1-4}$ alkyl (e.g., CF$_3$, CHF$_2$), halogenated $C_{1-4}$ alkoxy (e.g., OCF$_3$, OC$_2$F$_5$), COOH, COO—$C_{1-4}$ alkyl, CO—$C_{1-4}$ alkyl, $C_{1-4}$ alkyl —S— (e.g., CH$_3$S, C$_2$H$_5$S), halogenated $C_{1-4}$ alkyl —S— (e.g., CF$_3$S, C$_2$F$_5$S), benzyloxy, and pyrazolyl.

Non-limiting examples of heterocycles include: azepinyl, aziridinyl, azetyl, azetidinyl, diazepinyl, dithiadiazinyl, dioxazepinyl, dioxolanyl, dithiazolyl, furanyl, isooxazolyl, isothiazolyl, imidazolyl, morpholinyl, morpholino, oxetanyl, oxadiazolyl, oxiranyl, oxazinyl, oxazolyl, piperazinyl, pyrazinyl, pyridazinyl, pyrimidinyl, piperidyl, piperidino, pyridyl, pyranyl, pyrazolyl, pyrrolyl, pyrrolidinyl, thiatriazolyl, tetrazolyl, thiadiazolyl, triazolyl, thiazolyl, thienyl, tetrazinyl, thiadiazinyl, triazinyl, thiazinyl, thiopyranyl furoisoxazolyl, imidazothiazolyl, thienoisothiazolyl, thienothiazolyl, imidazopyrazolyl, cyclopentapyrazolyl, pyrrolopyrrolyl, thienothienyl, thiadiazolopyrimidinyl, thiazolothiazinyl, thiazolopyrimidinyl, thiazolopyridinyl, oxazolopyrimidinyl, oxazolopyridyl, benzoxazolyl, benzisothiazolyl, benzothiazolyl, imidazopyrazinyl, purinyl, pyrazolopyrimidinyl, imidazopyridinyl, benzimidazolyl, indazolyl, benzoxathiolyl, benzodioxolyl, benzodithiolyl, indolizinyl, indolinyl, isoindolinyl, furopyrimidinyl, furopyridyl, benzofuranyl, isobenzofuranyl, thienopyrimidinyl, thienopyridyl, benzothienyl, cyclopentaoxazinyl, cyclopentafuranyl, benzoxazinyl, benzothiazinyl, quinazolinyl, naphthyridinyl, quinolinyl, isoquinolinyl, benzopyranyl, pyridopyridazinyl and pyridopyrimidinyl groups.

The invention further encompasses any other physiochemical or sterochemical form that the compound may assume. Such forms include diastereomers, racemates, isolated enantiomers, hydrated forms, solvated forms, any known or yet to be disclosed crystalline or amorphous form including all polymorphic crystalline forms. Amorphous forms lack a distinguishable crystal lattice and therefore lack an orderly arrangement of structural units. Many pharmaceutical compounds have amorphous forms. Methods of generating such chemical forms will be well known by one skilled in the art.

Another aspect of the invention is that the carbon atom bearing R or —CH2OH or R4 in Formula I, II, or III may have "S" or "R" configuration. All the diastereomers, racemates, isolated enantiomers are within the scope of the invention.

Racemates, individual enantiomers, or diasteromers of the compound may be prepared by specific synthesis or resolution through any method now known or yet to be disclosed. For example, the compound may be resolved into it enantiomers by the formation of diasteromeric pairs through salt formation using an optically active acid. Enantiomers are fractionally crystallized and the free base regenerated. In another example, enantiomers may be separated by chromatography. Such chromatography may be any appropriate method now known or yet to be disclosed that is appropriate to separate enantiomers such as HPLC on a chiral column.

In some embodiments, the compound is in the form of a pharmaceutically acceptable salt. Pharmaceutically acceptable salts include any salt derived from an organic or inorganic acid. Non-limiting examples of such salts include: salts of hydrobromic acid, hydrochloric acid, nitric acid, phosphoric acid, and sulphuric acid. Organic acid addition salts include, for example, salts of acetic acid, benzenesulphonic acid, benzoic acid, camphorsulphonic acid, citric acid, 2-(4-chlorophenoxy)-2-methylpropionic acid, 1, 2-ethanedisulphonic acid, ethanesulphonic acid, ethylenediaminetetraacetic acid (EDTA), fumaric acid, glucoheptonic acid, gluconic acid, glutamic acid, N-glycolylarsanilic acid, 4-hexylresorcinol, hippuric acid, 2-(4-hydroxybenzoyl) benzoicacid, 1-hydroxy-2-naphthoicacid, 3-hydroxy-2-naphthoic acid, 2-hydroxyethanesulphonic acid, lactobionic acid, n-dodecyl sulphuric acid, maleic acid, malic acid, mandelic acid, methanesulphonic acid, methyl sulpuric acid, mucic acid, 2-naphthalenesulphonic acid, pamoic acid, pantothenic acid, phosphanilic acid ((4-aminophenyl) phosphonic acid), picric acid, salicylic acid, stearic acid, succinic acid, tannic acid, tartaric acid, terephthalic acid, p-toluenesulphonic acid, 10-undecenoic acid or any other such acid now known or yet to be disclosed. It will be appreciated that such salts, provided that they are pharmaceutically acceptable, may be used in therapy. Such salts may be prepared by reacting the compound with a suitable acid in a manner known by those skilled in the art.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isethionate, lactate, lactobionate, laurate, magnesium, malate, maleate, mandelate, mesylate, methyl bromide, methyl nitrate, methyl sulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, subsalicylate, suramate, tannate, tartrate, teoclate, tosylate, triethiodide, and valerate salts.

As used herein, the term "stereoisomers" refers to the set of compounds which have the same number and type of atoms and share the same bond connectivity between those atoms, but differ in three-dimensional structure. The term "stereoisomer" refers to any member of this set of compounds.

As used herein, the term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. As used herein, the term "diastereomer" refers to any member of this set of compounds. In some examples presented, the synthetic route may produce a single diastereomer or a mixture of diastereomers. In some cases, these diastereomers were separated and in other cases a wavy bond is used to indicate the structural element where configuration is variable.

As used herein, the term "enantiomers" refers to a pair of stereoisomers which are non-superimposable mirror images of one another. As used herein, the term "enantiomer" refers to a single member of this pair of stereoisomers. As used herein, the term "racemic" refers to a 1:1 mixture of a pair of enantiomers.

As used herein, the term "tautomers" refers to a set of compounds that have the same number and type of atoms, but differ in bond connectivity and are in equilibrium with one another. A "tautomer" is a single member of this set of compounds. Typically, a single tautomer is drawn but it is understood that this single structure is meant to represent all possible tautomers that might exist. Examples include enol-ketone tautomerism. When a ketone is drawn it is understood that both the enol and ketone forms are part of the disclosure.

An "effective amount" when used in connection with a compound is an amount effective for treating or preventing a disease in a subject as described herein.

As used herein, the term "carrier" encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

As used herein, the term "treating" with regard to a subject, refers to improving at least one symptom of the subject's disorder. Treating includes curing, improving, or at least partially ameliorating the disorder.

As used herein, the term "disorder" is used in this disclosure to mean, and is used interchangeably with, the terms disease, condition, or illness, unless otherwise indicated.

As used herein, the term "administer," "administering," or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

As used herein, the term "prodrug" means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (e.g., using an enzyme).

As used herein, the term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

As used herein, the term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the disclosed compounds may have one or more asymmetric carbon atom and may occur as racemates, racemic mixtures and as individual enantiomers or diastereomers.

A "patient" or "subject" is a mammal, e.g., a human, mouse, rat, guinea pig, dog, cat, horse, cow, pig, or non-human primate, such as a monkey, chimpanzee, baboon or rhesus.

As used herein, the terms "FLT3 mutated proliferative disorder(s)," "disorder related to FLT3," "disorders related to FLT3 receptor," "disorders related to FLT3 receptor tyrosine kinase," "a deregulated FLT3 receptor tyrosine kinase disease," or "FLT3 driven cell proliferative disorder" includes diseases associated with or implicating FLT3 activity, for example, mutations leading to constitutive activation of FLT3. Non-limiting examples of "FLT3 mutated proliferative disorder(s)" include disorders resulting from over stimulation of FLT3 due to mutations in FLT3, or disorders resulting from abnormally high amount of FLT3 activity due to abnormally high amount of mutations in FLT3. It is known that over-activity of FLT3 has been implicated in the pathogenesis of many diseases, including the following listed cell proliferative disorders, neoplastic disorders, and cancers. Non-limiting examples of proliferative disorders for treatment with the present invention include leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

As used herein, the terms "proliferative disorder(s)" and "cell proliferative disorder(s)" refer to excess cell proliferation of one or more subset of cells in a multicellular organism resulting in harm (i.e., discomfort or decreased life expectancy) to the multicellular organism. Cell proliferative disorders can occur in different types of animals and humans. As used herein, "cell proliferative disorders" include neoplastic disorders.

As used herein, the term "neoplastic disorder" refers to a tumor resulting from abnormal or uncontrolled cellular growth. Examples of neoplastic disorders include, but are not limited to the following disorders, for instance: the myeloproliferative disorders, such as thrombocytopenia, essential thrombocytosis (ET), agnogenic myeloid metaplasia, myelofibrosis (MF), myelofibrosis with myeloid metaplasia (MMM), chronic idiopathic myelofibrosis (UIMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematological malignancies, including myelodysplasia, multiple myeloma, leukemias, and lymphomas. Examples of hematological malignancies include, for instance, leukemias, lymphomas, Hodgkin's disease, and myeloma. Also, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), myelodysplastic syndromes (MDSs), myeloproliferative disorders (MPD), and multiple myeloma (MM). In certain embodiments, the present invention is directed at the use of a compound disclosed herein or a pharmaceutically acceptable salt thereof in an amount sufficient for the treatment of a neoplastic disorder.

Certain embodiments include a method of specifically inhibiting a deregulated receptor tyrosine kinase, comprising: obtaining a sample of a subject, determining which receptor tyrosine kinases are deregulated in the sample, and administering to the subject an effective amount of the compound of Formula I or a salt thereof, wherein the deregulated receptor tyrosine kinase is a FLT3 receptor tyrosine kinase. In some implementations, the effective amount of the compound of Formula I or a salt thereof is an amount that decreases the subject's circulating peripheral blood blast count. In other implementations, the effective amount of the effective amount of the compound of Formula I or a salt thereof is an amount that decreases the subject's bone marrow blast count. In yet other implementations, the proliferative disease is selected from: leukemia, myeloma, a myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, hematologic malignancy, and combinations thereof.

In some embodiments, the compound of Formula I is an enantiomer. In some implementations, the compound is an (S)-enantiomer. In other implementations, the compound is a (R)-enantiomer. In some embodiments, the (R)- or (S)-enantiomeric configuration is assigned to the molecule. In other embodiments, the (R)- or (S)-enantiomeric configuration is not assigned to the molecule despite the enantiomeric purification or separation of the molecule. In yet other embodiments, the disclosed compound is a (+) or (−) enantiomer.

It should be understood that all isomeric forms are included within the present disclosure, including mixtures thereof. If the compound contains a double bond, the substituent may be in the E or Z configuration or cis or trans configuration. If the compound contains a disubstituted cycloalkyl, the cycloalkyl substituent may have a cis- or trans configuration. All tautomeric forms are also intended to be included. In some embodiments, the cis or trans configuration may be assigned to each molecule. In other embodiments, the cis or trans configuration may not be assigned to the molecules despite the chemical purification or separation of the diastereomers.

Examples that represent different aspects of the invention follow. Such examples should not be construed as limiting the scope of the disclosure. Alternative mechanistic pathways and analogous structures within the scope of the invention would be apparent to those skilled in the art.

Elements and acts in the examples are intended to illustrate the invention for the sake of simplicity and have not necessarily been rendered according to any particular sequence or embodiment.

TABLE 1

| | Non-limiting examples of kinase inhibitor compounds. | |
|---|---|---|
| ID | Structure | M + 1 |
| 1 | | 467 |

TABLE 1-continued
Non-limiting examples of kinase inhibitor compounds.
| ID | Structure | M + 1 |
|---|---|---|
| 2 | 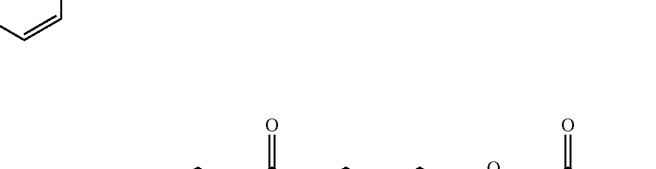 | 507 |
| 3 | 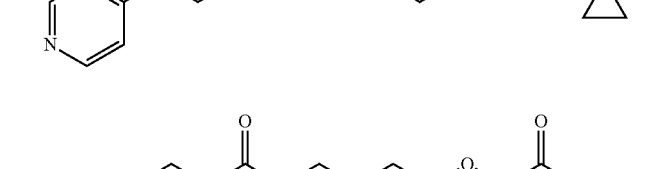 | 402 |
| 4 | 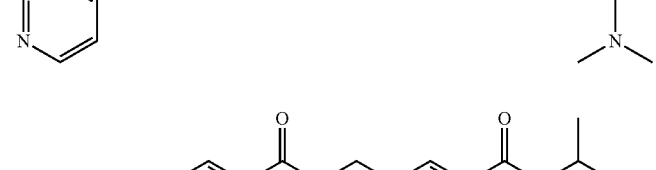 | 433 |
| 5 | 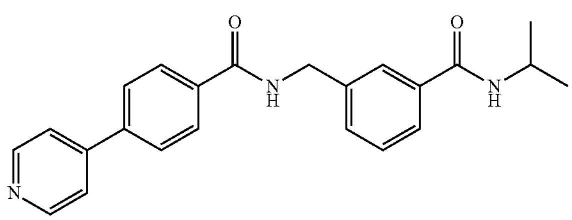 [SMILES: CC(C)NC(=O)c1cccc(CNC(=O)c2ccc(-c3ccncc3)cc2)c1] | 374 |
| 6 | 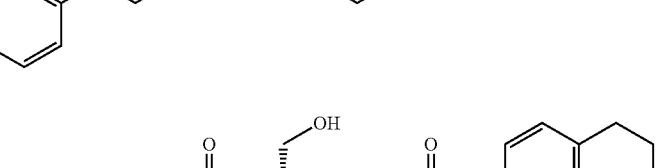 | 491 |
| 7 | 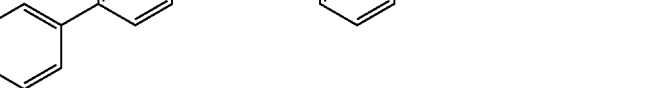 | 507 |

TABLE 1-continued
Non-limiting examples of kinase inhibitor compounds.
| ID | Structure | M + 1 |
|---|---|---|
| 8 | 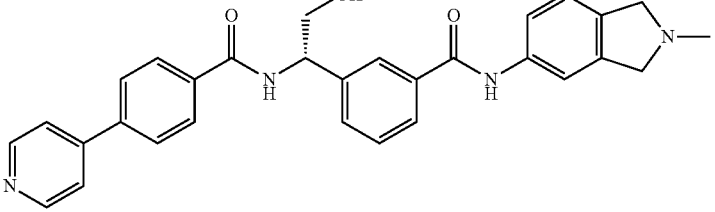 | 493 |
| 9 | 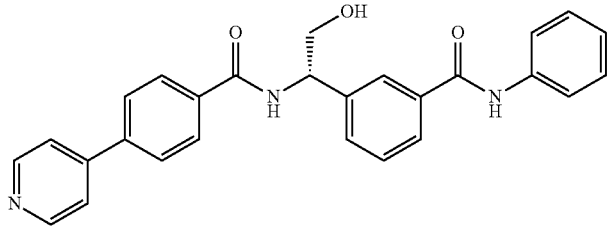 [SMILES: O=C(Nc1ccccc1)c1cccc([C@@H](CO)NC(=O)c2ccc(-c3ccncc3)cc2)c1] | 438 |
| 10 | 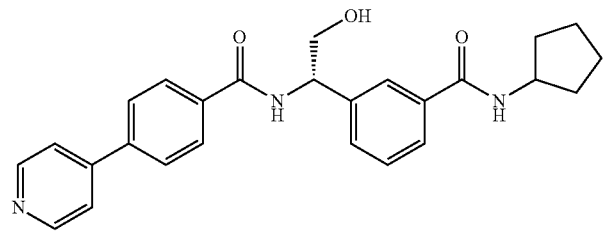 | 430 |
| 11 | 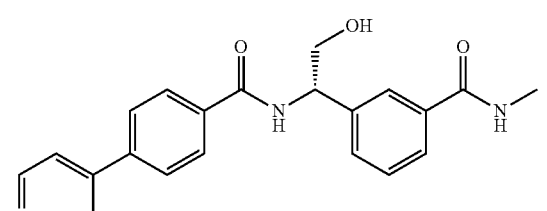 | 376 |
| 12 | 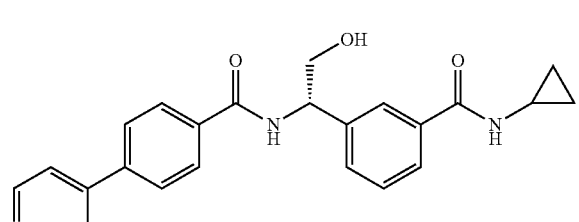 | 402 |
| 13 | 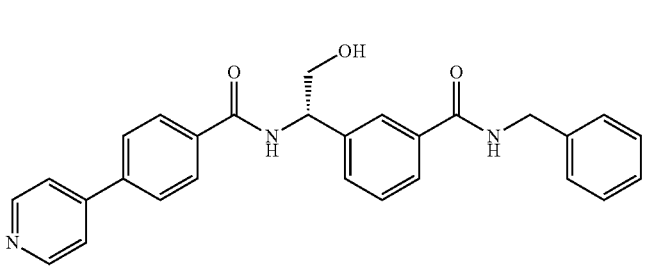 [SMILES: O=C(NCc1ccccc1)c1cccc([C@@H](CO)NC(=O)c2ccc(-c3ccncc3)cc2)c1] | 452 |

TABLE 1-continued

Non-limiting examples of kinase inhibitor compounds.

| ID | Structure | M + 1 |
|---|---|---|
| 14 | 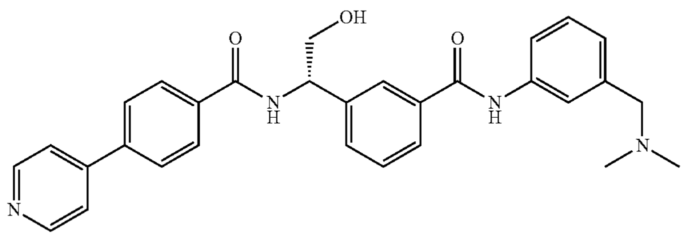 [SMILES: CN(C)Cc1cccc(NC(=O)c2cccc([C@@H](CO)NC(=O)c3ccc(-c4ccncc4)cc3)c2)c1] | 495 |
| 15 | 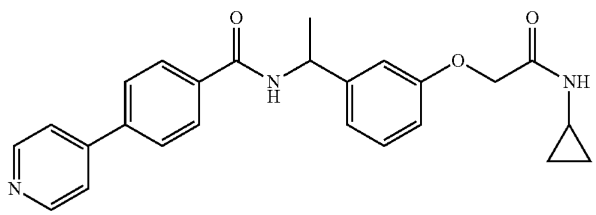 [SMILES: CC(NC(=O)c1ccc(-c2ccncc2)cc1)c1cccc(OCC(=O)NC2CC2)c1] | 416 |
| 16 | 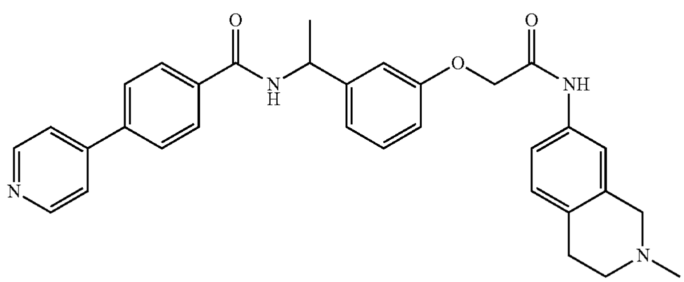 [SMILES: CC(NC(=O)c1ccc(-c2ccncc2)cc1)c1cccc(OCC(=O)Nc2ccc3c(c2)CN(C)CC3)c1] | 521 |
| 17 | 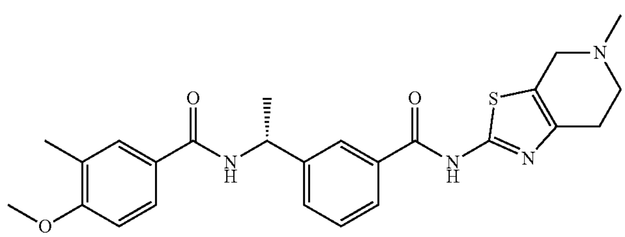 | 465 |
| 18 | 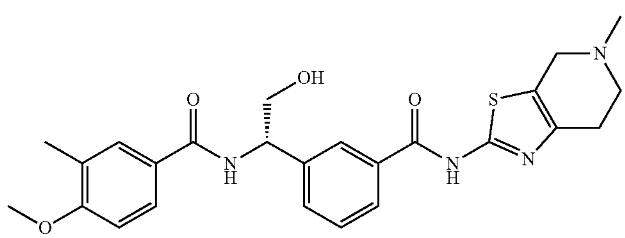 | 481 |
| 19 | 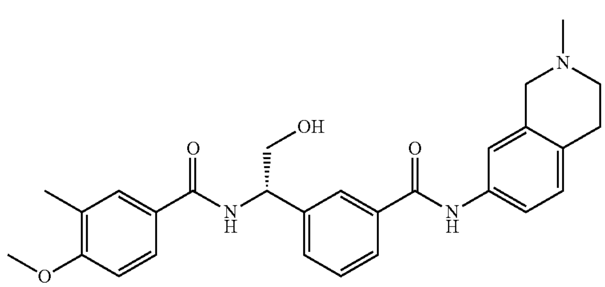 [SMILES: COc1ccc(C(=O)N[C@H](CO)c2cccc(C(=O)Nc3ccc4c(c3)CN(C)CC4)c2)cc1C] | 474 |

TABLE 1-continued
Non-limiting examples of kinase inhibitor compounds.
| ID | Structure | M + 1 |
|---|---|---|
| 20 | 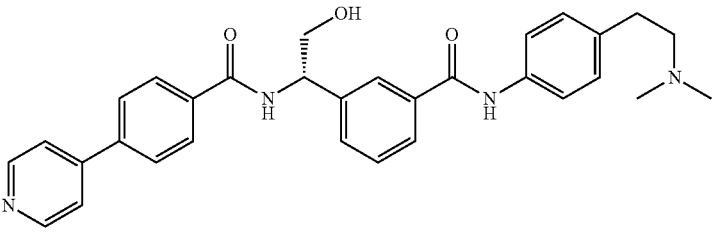 [SMILES: CN(C)CCc1ccc(NC(=O)c2cccc([C@@H](CO)NC(=O)c3ccc(-c4ccncc4)cc3)c2)cc1] | 509 |
| 21 | 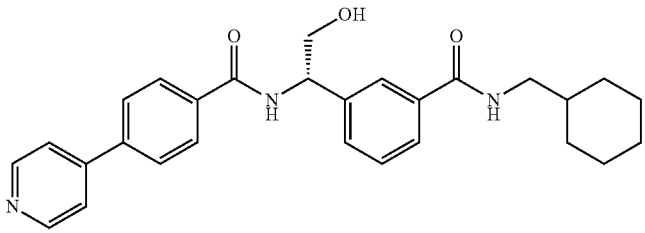 [SMILES: O=C(NCC1CCCCC1)c1cccc([C@@H](CO)NC(=O)c2ccc(-c3ccncc3)cc2)c1] | 458 |
| 22 | 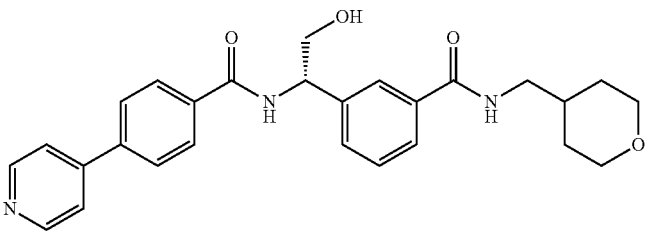 [SMILES: O=C(NCC1CCOCC1)c1cccc([C@@H](CO)NC(=O)c2ccc(-c3ccncc3)cc2)c1] | 460 |
| 23 | 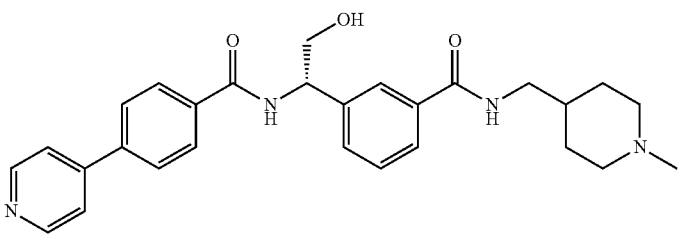 | 473 |
| 24 | 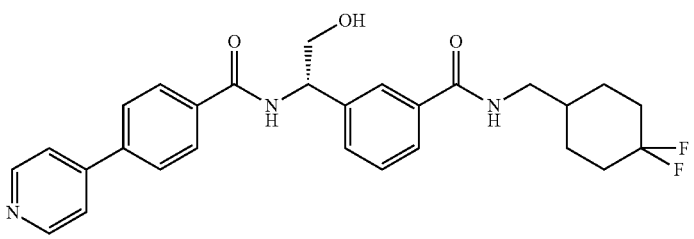 [SMILES: O=C(NCC1CCC(F)(F)CC1)c1cccc([C@@H](CO)NC(=O)c2ccc(-c3ccncc3)cc2)c1] | 494 |
| 25 | 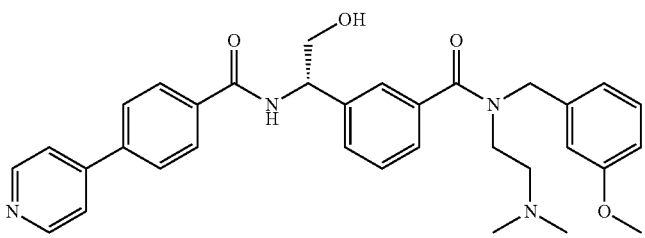 [SMILES: COc1cccc(CN(CCN(C)C)C(=O)c2cccc([C@@H](CO)NC(=O)c3ccc(-c4ccncc4)cc3)c2)c1] | 553 |

TABLE 1-continued

Non-limiting examples of kinase inhibitor compounds.

| ID | Structure | M + 1 |
|----|-----------|-------|
| 26 | 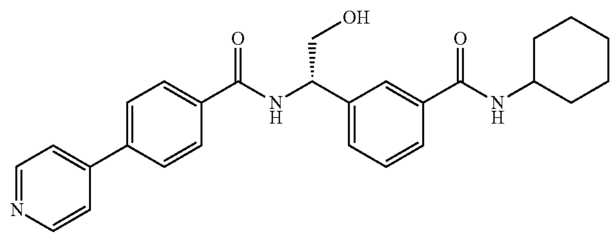 [SMILES: O=C(NC1CCCCC1)c1cccc([C@@H](CO)NC(=O)c2ccc(-c3ccncc3)cc2)c1] | 444 |
| 27 | 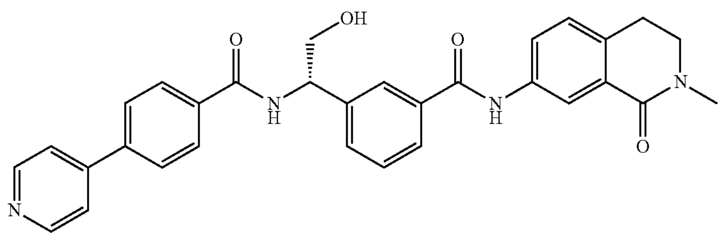 [SMILES: CN1CCc2ccc(NC(=O)c3cccc([C@@H](CO)NC(=O)c4ccc(-c5ccncc5)cc4)c3)cc2C1=O] | 521 |
| 28 | 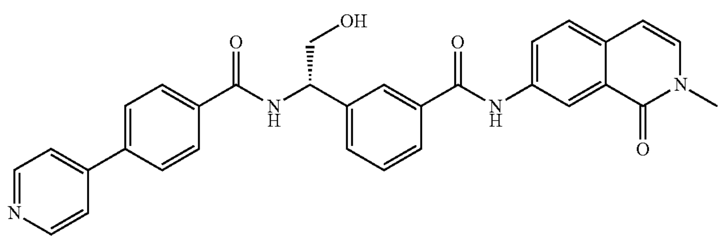 [SMILES: Cn1ccc2ccc(NC(=O)c3cccc([C@@H](CO)NC(=O)c4ccc(-c5ccncc5)cc4)c3)cc2c1=O] | 519 |
| 29 | 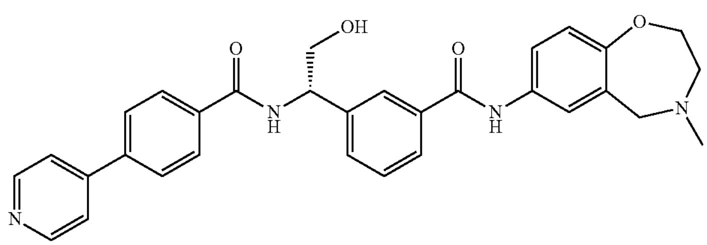 [SMILES: CN1CCOc2ccc(NC(=O)c3cccc([C@@H](CO)NC(=O)c4ccc(-c5ccncc5)cc4)c3)cc2C1] | 523 |
| 30 | 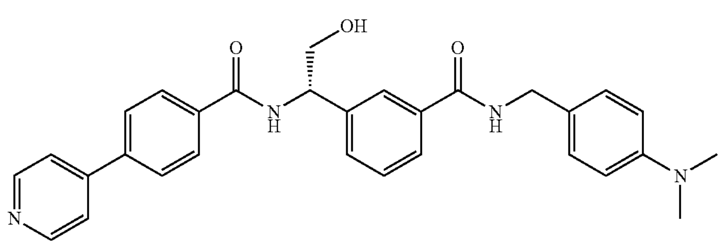 [SMILES: CN(C)c1ccc(CNC(=O)c2cccc([C@@H](CO)NC(=O)c3ccc(-c4ccncc4)cc3)c2)cc1] | 495 |
| 31 | 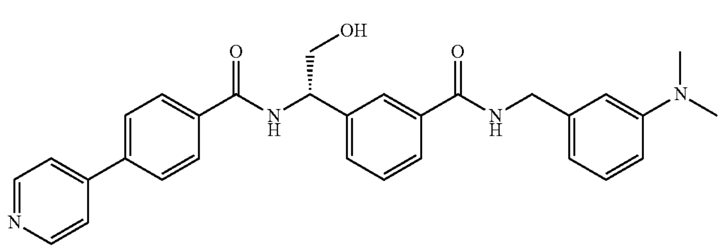 [SMILES: CN(C)c1cccc(CNC(=O)c2cccc([C@@H](CO)NC(=O)c3ccc(-c4ccncc4)cc3)c2)c1] | 495 |

TABLE 1-continued

Non-limiting examples of kinase inhibitor compounds.

| ID | Structure | M + 1 |
|---|---|---|
| 32 | 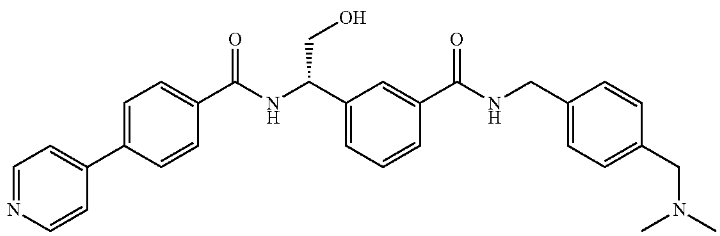 [SMILES: CN(C)Cc1ccc(CNC(=O)c2cccc([C@@H](CO)NC(=O)c3ccc(-c4ccncc4)cc3)c2)cc1] | 509 |
| 33 | 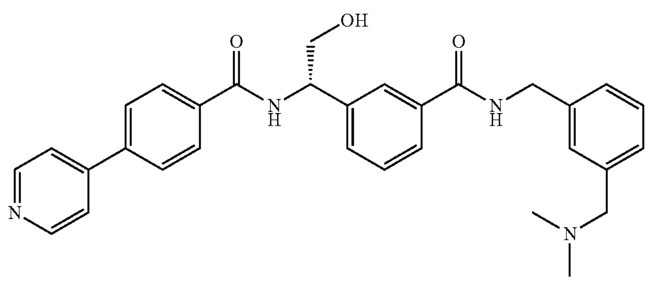 [SMILES: CN(C)Cc1cccc(CNC(=O)c2cccc([C@@H](CO)NC(=O)c3ccc(-c4ccncc4)cc3)c2)c1] | 509 |
| 34 | 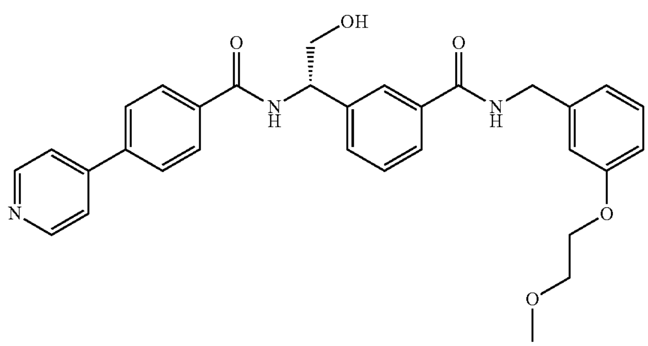 [SMILES: COCCOc1cccc(CNC(=O)c2cccc([C@@H](CO)NC(=O)c3ccc(-c4ccncc4)cc3)c2)c1] | 526 |
| 35 | 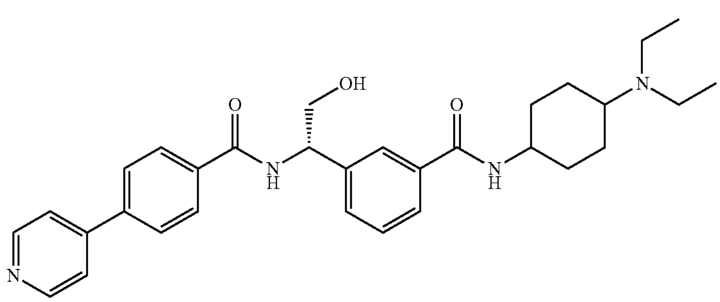 [SMILES: CCN(CC)C1CCC(NC(=O)c2cccc([C@@H](CO)NC(=O)c3ccc(-c4ccncc4)cc3)c2)CC1] | 515 |
| 36 | 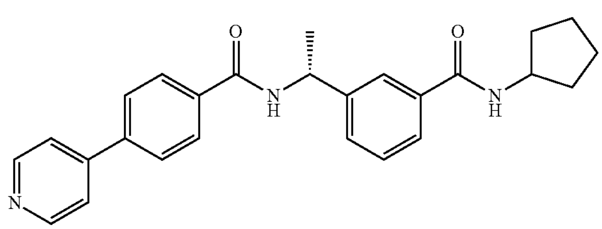 [SMILES: C[C@@H](NC(=O)c1ccc(-c2ccncc2)cc1)c1cccc(C(=O)NC2CCCC2)c1] | 413 |

TABLE 1-continued

Non-limiting examples of kinase inhibitor compounds.

| ID | Structure | M + 1 |
|---|---|---|
| 37 | 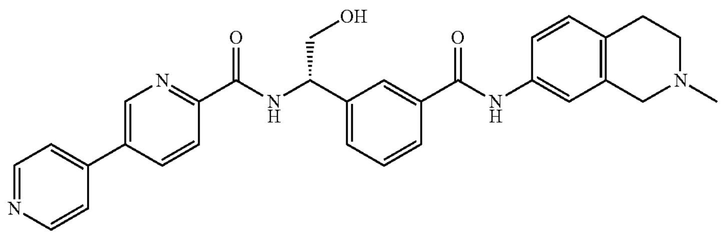 [SMILES: CN1CCc2ccc(NC(=O)c3cccc([C@@H](CO)NC(=O)c4ccc(-c5ccncc5)cn4)c3)cc2C1] | 508 |
| 38 | 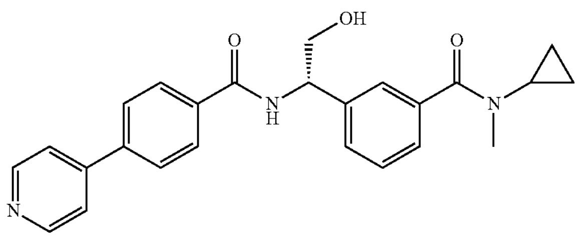 [SMILES: CN(C(=O)c1cccc([C@@H](CO)NC(=O)c2ccc(-c3ccncc3)cc2)c1)C1CC1] | 416 |
| 39 | 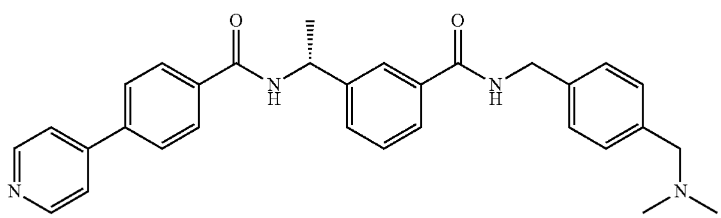 [SMILES: C[C@@H](NC(=O)c1ccc(-c2ccncc2)cc1)c1cccc(C(=O)NCc2ccc(CN(C)C)cc2)c1] | 493 |
| 40 | 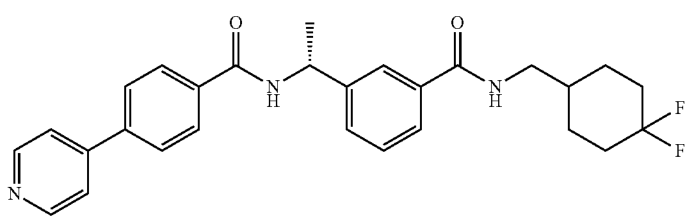 [SMILES: C[C@@H](NC(=O)c1ccc(-c2ccncc2)cc1)c1cccc(C(=O)NCC2CCC(F)(F)CC2)c1] | 478 |
| 41 | 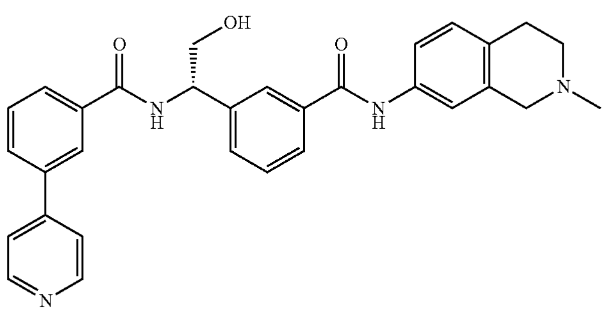 [SMILES: CN1CCc2ccc(NC(=O)c3cccc([C@@H](CO)NC(=O)c4cccc(-c5ccncc5)c4)c3)cc2C1] | 507 |
| 42 | 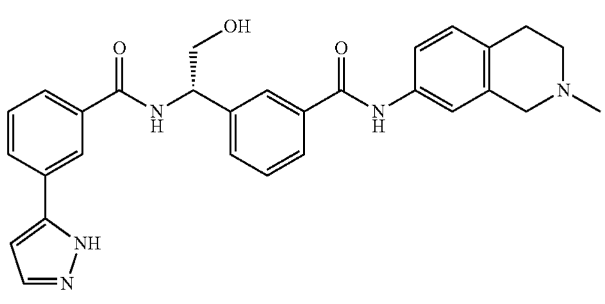 [SMILES: CN1CCc2ccc(NC(=O)c3cccc([C@@H](CO)NC(=O)c4cccc(-c5ccn[nH]5)c4)c3)cc2C1] | 496 |

TABLE 1-continued

Non-limiting examples of kinase inhibitor compounds.

| ID | Structure | M + 1 |
|----|-----------|-------|
| 43 | 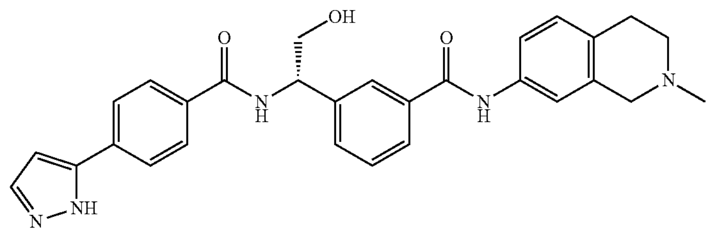 [SMILES: CN1CCc2ccc(NC(=O)c3cccc([C@@H](CO)NC(=O)c4ccc(-c5ccn[nH]5)cc4)c3)cc2C1] | 496 |
| 44 | 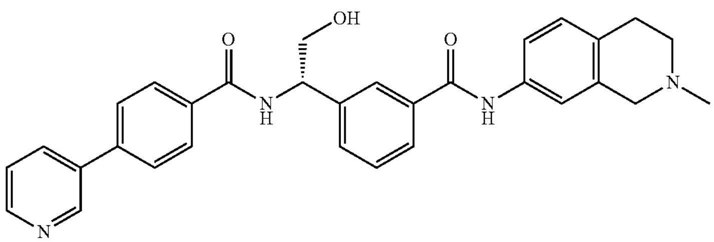 [SMILES: CN1CCc2ccc(NC(=O)c3cccc([C@@H](CO)NC(=O)c4ccc(-c5cccnc5)cc4)c3)cc2C1] | 507 |
| 45 | 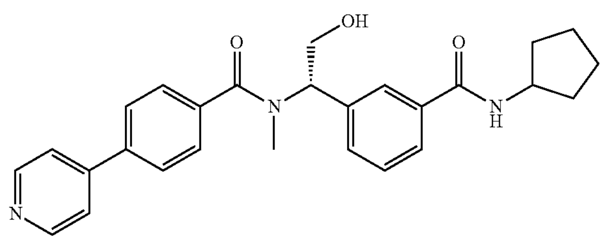 [SMILES: CN(C(=O)c1ccc(-c2ccncc2)cc1)[C@H](CO)c1cccc(C(=O)NC2CCCC2)c1] | 444 |
| 46 | 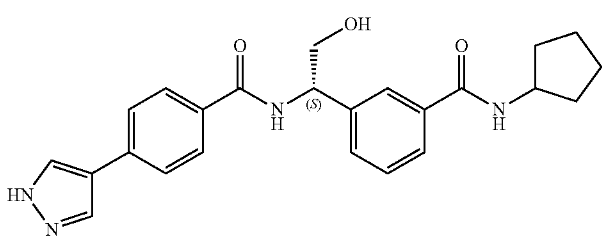 | 419 |
| 47 | 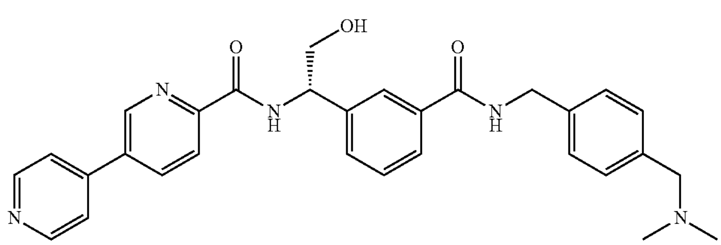 [SMILES: CN(C)Cc1ccc(CNC(=O)c2cccc([C@@H](CO)NC(=O)c3ccc(-c4ccncc4)cn3)c2)cc1] | 510 |
| 48 | 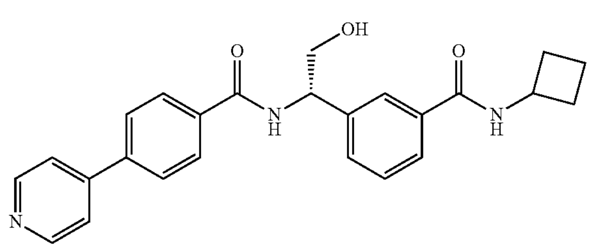 [SMILES: O=C(NC1CCC1)c1cccc([C@@H](CO)NC(=O)c2ccc(-c3ccncc3)cc2)c1] | 416 |

TABLE 1-continued

Non-limiting examples of kinase inhibitor compounds.

| ID | Structure | M + 1 |
|---|---|---|
| 49 | 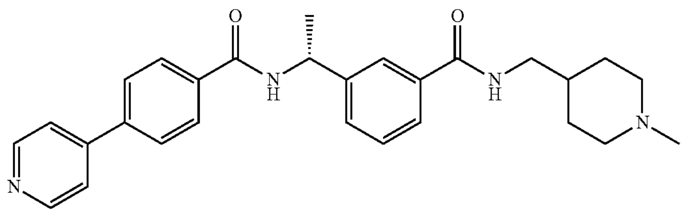 [SMILES: C[C@@H](NC(=O)c1ccc(-c2ccncc2)cc1)c1cccc(C(=O)NCC2CCN(C)CC2)c1] | 457 |
| 50 | 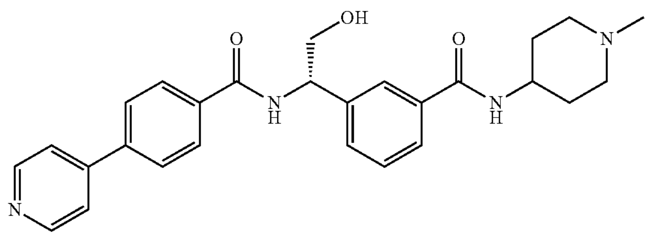 [SMILES: CN1CCC(NC(=O)c2cccc([C@@H](CO)NC(=O)c3ccc(-c4ccncc4)cc3)c2)CC1] | 459 |
| 51 | 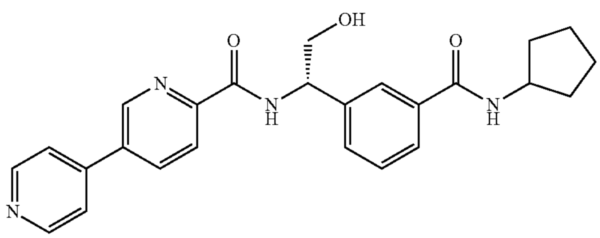 [SMILES: O=C(NC1CCCC1)c1cccc([C@@H](CO)NC(=O)c2ccc(-c3ccncc3)cn2)c1] | 431 |
| 52 | 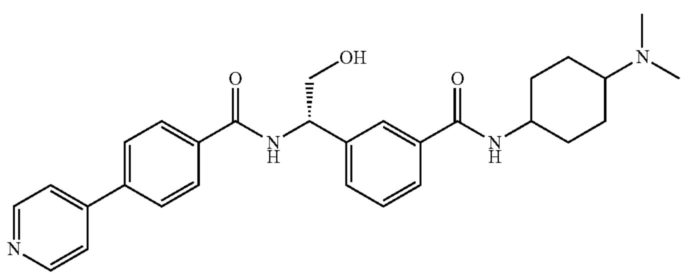 [SMILES: CN(C)C1CCC(NC(=O)c2cccc([C@@H](CO)NC(=O)c3ccc(-c4ccncc4)cc3)c2)CC1] | 487 |
| 53 | 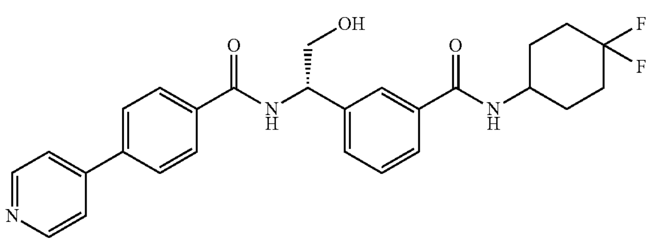 [SMILES: O=C(NC1CCC(F)(F)CC1)c1cccc([C@@H](CO)NC(=O)c2ccc(-c3ccncc3)cc2)c1] | 480 |
| 54 | 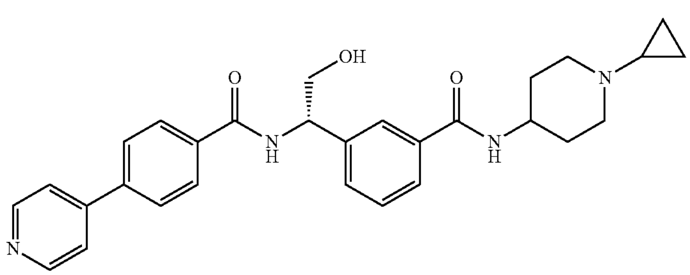 [SMILES: O=C(NC1CCN(C2CC2)CC1)c1cccc([C@@H](CO)NC(=O)c2ccc(-c3ccncc3)cc2)c1] | 485 |

TABLE 1-continued

Non-limiting examples of kinase inhibitor compounds.

| ID | Structure | M + 1 |
|---|---|---|
| 55 | 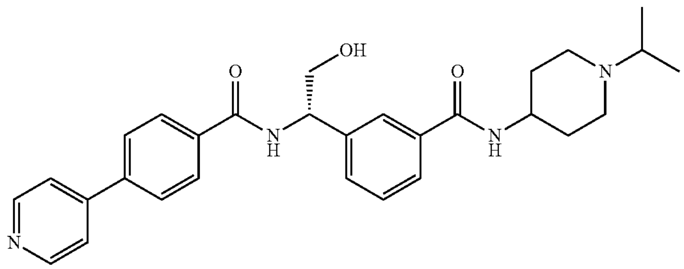 [SMILES: CC(C)N1CCC(NC(=O)c2cccc([C@@H](CO)NC(=O)c3ccc(-c4ccncc4)cc3)c2)CC1] | 487 |
| 56 | 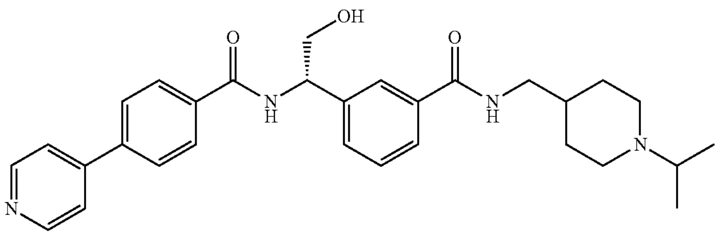 [SMILES: CC(C)N1CCC(CNC(=O)c2cccc([C@@H](CO)NC(=O)c3ccc(-c4ccncc4)cc3)c2)CC1] | 501 |
| 57 | 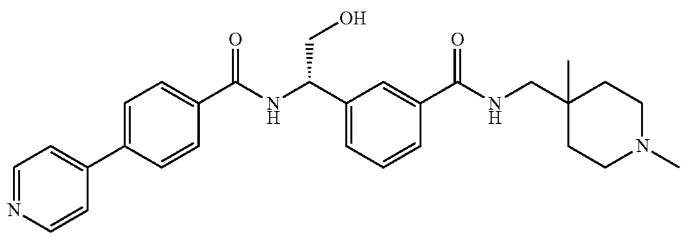 [SMILES: CN1CCC(C)(CNC(=O)c2cccc([C@@H](CO)NC(=O)c3ccc(-c4ccncc4)cc3)c2)CC1] | 487 |
| 58 | 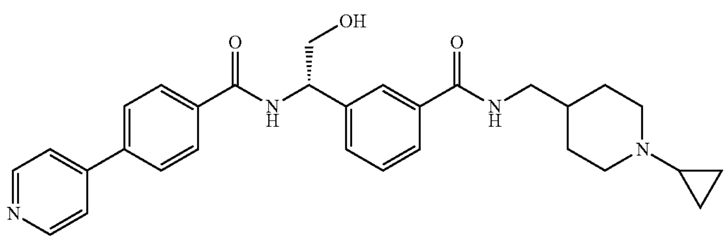 [SMILES: O=C(NCC1CCN(C2CC2)CC1)c1cccc([C@@H](CO)NC(=O)c2ccc(-c3ccncc3)cc2)c1] | 499 |
| 59 | 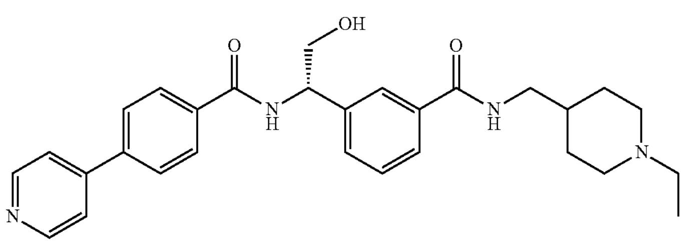 [SMILES: CCN1CCC(CNC(=O)c2cccc([C@@H](CO)NC(=O)c3ccc(-c4ccncc4)cc3)c2)CC1] | 487 |
| 60 | 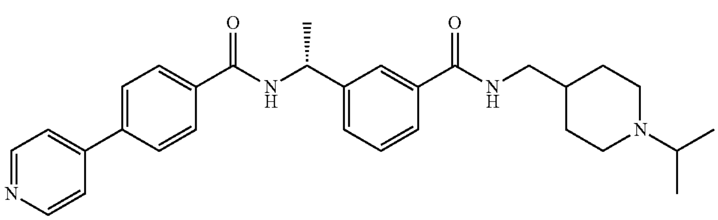 [SMILES: CC(C)N1CCC(CNC(=O)c2cccc([C@@H](C)NC(=O)c3ccc(-c4ccncc4)cc3)c2)CC1] | 485 |

TABLE 1-continued

Non-limiting examples of kinase inhibitor compounds.

| ID | Structure | M + 1 |
|---|---|---|
| 61 | 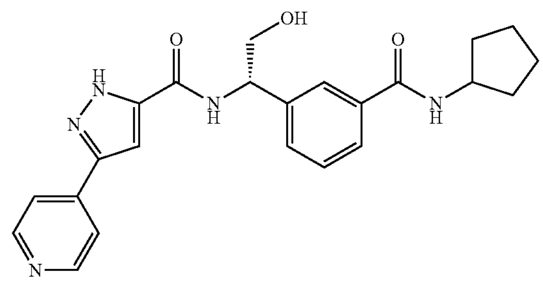 [SMILES: O=C(NC1CCCC1)c1cccc([C@@H](CO)NC(=O)c2cc(-c3ccncc3)n[nH]2)c1] | 420 |
| 62 | 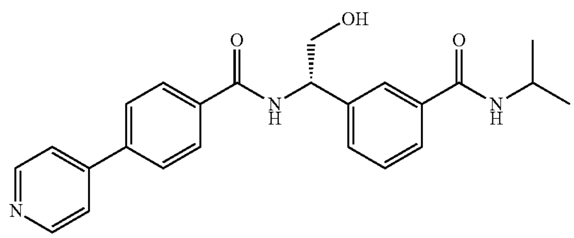 [SMILES: CC(C)NC(=O)c1cccc([C@@H](CO)NC(=O)c2ccc(-c3ccncc3)cc2)c1] | 404 |
| 63 | 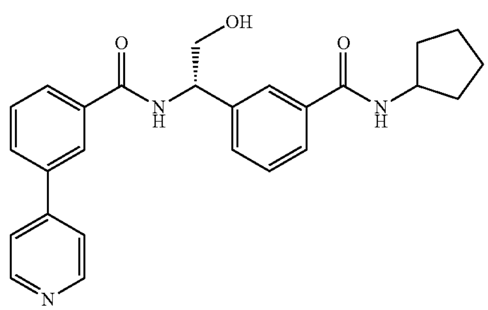 [SMILES: O=C(NC1CCCC1)c1cccc([C@@H](CO)NC(=O)c2cccc(-c3ccncc3)c2)c1] | 430 |
| 64 | 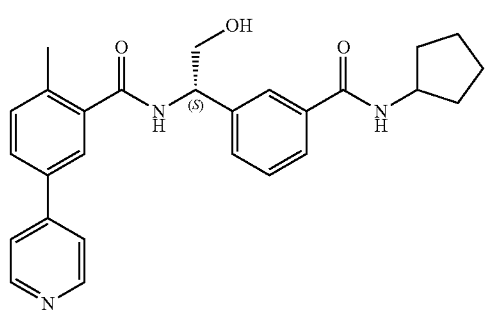 | 444 |
| 65 | 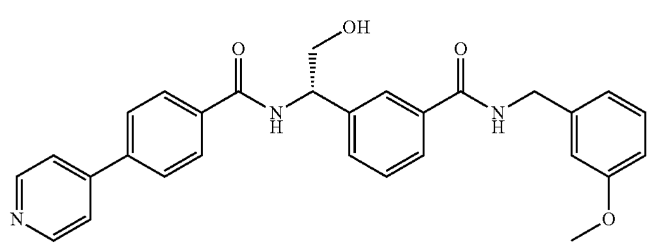 [SMILES: COc1cccc(CNC(=O)c2cccc([C@@H](CO)NC(=O)c3ccc(-c4ccncc4)cc3)c2)c1] | 482 |

TABLE 1-continued
Non-limiting examples of kinase inhibitor compounds.
| ID | Structure | M + 1 |
|---|---|---|
| 66 | 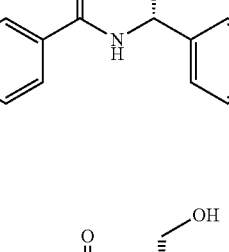 | 430 |
| 67 | 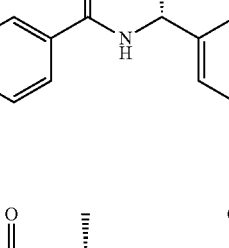 | 474 |
| 68 | 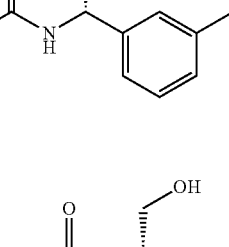 | 452 |
| 69 | 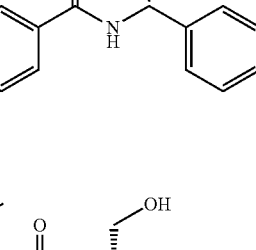 | 474 |
| 70 | 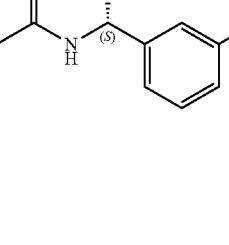 | 458 |
| 71 | 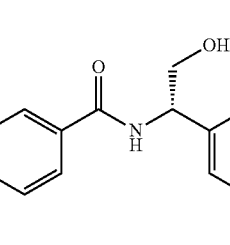 | 430 |

TABLE 1-continued

Non-limiting examples of kinase inhibitor compounds.

| ID | Structure | M + 1 |
|---|---|---|
| 72 | 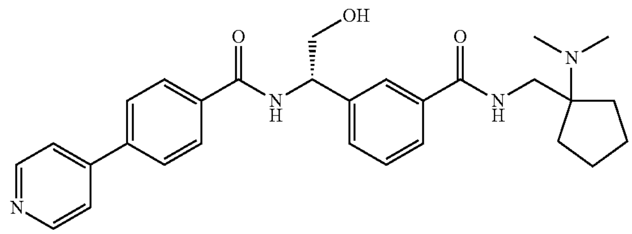 [SMILES: CN(C)C1(CNC(=O)c2cccc([C@@H](CO)NC(=O)c3ccc(-c4ccncc4)cc3)c2)CCCC1] | 487 |
| 73 | 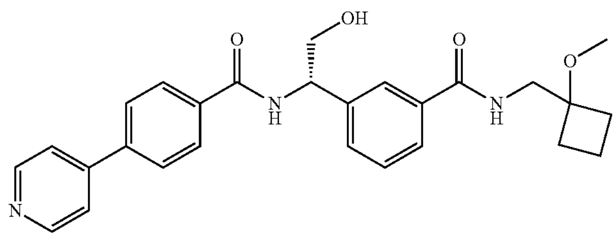 [SMILES: COC1(CNC(=O)c2cccc([C@@H](CO)NC(=O)c3ccc(-c4ccncc4)cc3)c2)CCC1] | 460 |
| 74 | 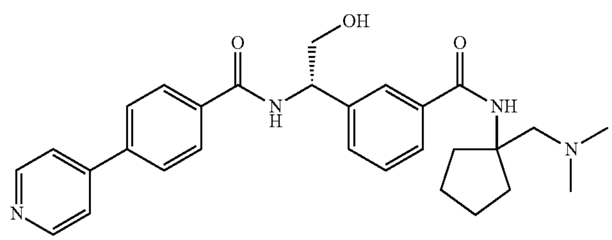 [SMILES: CN(C)CC1(NC(=O)c2cccc([C@@H](CO)NC(=O)c3ccc(-c4ccncc4)cc3)c2)CCCC1] | 487 |
| 75 | 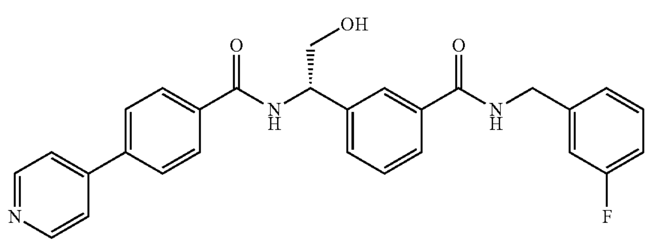 [SMILES: O=C(NCc1cccc(F)c1)c1cccc([C@@H](CO)NC(=O)c2ccc(-c3ccncc3)cc2)c1] | 470 |
| 76 | 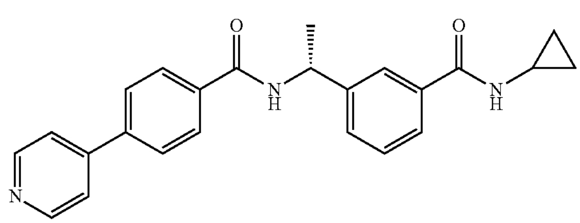 [SMILES: C[C@@H](NC(=O)c1ccc(-c2ccncc2)cc1)c1cccc(C(=O)NC2CC2)c1] | 386 |
| 77 | 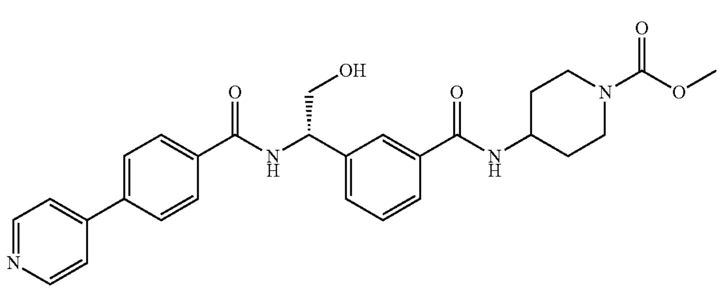 [SMILES: COC(=O)N1CCC(NC(=O)c2cccc([C@@H](CO)NC(=O)c3ccc(-c4ccncc4)cc3)c2)CC1] | 503 |

TABLE 1-continued

Non-limiting examples of kinase inhibitor compounds.

| ID | Structure | M + 1 |
|---|---|---|
| 78 | 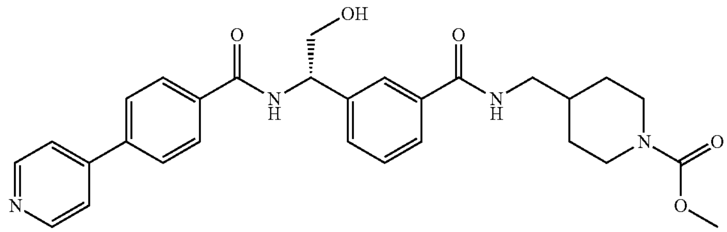 [SMILES: COC(=O)N1CCC(CNC(=O)c2cccc([C@@H](CO)NC(=O)c3ccc(-c4ccncc4)cc3)c2)CC1] | 517 |
| 79 | 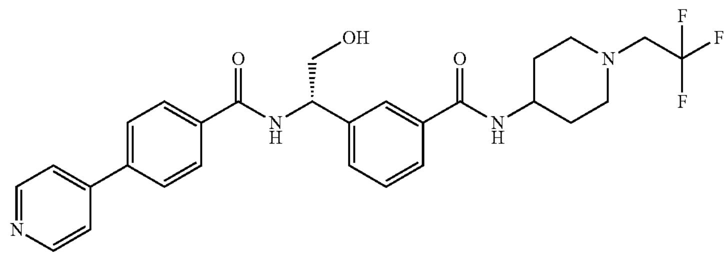 [SMILES: O=C(NC1CCN(CC(F)(F)F)CC1)c1cccc([C@@H](CO)NC(=O)c2ccc(-c3ccncc3)cc2)c1] | 527 |
| 80 | 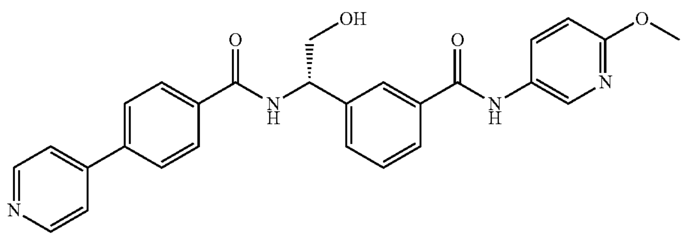 [SMILES: COc1ccc(NC(=O)c2cccc([C@@H](CO)NC(=O)c3ccc(-c4ccncc4)cc3)c2)cn1] | 469 |
| 81 | 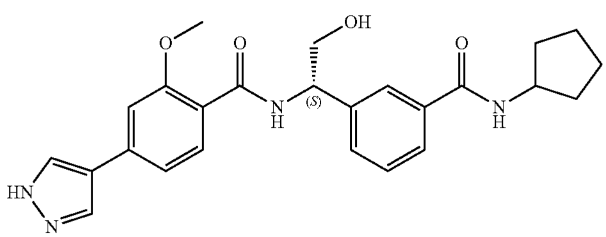 | 449 |
| 82 | 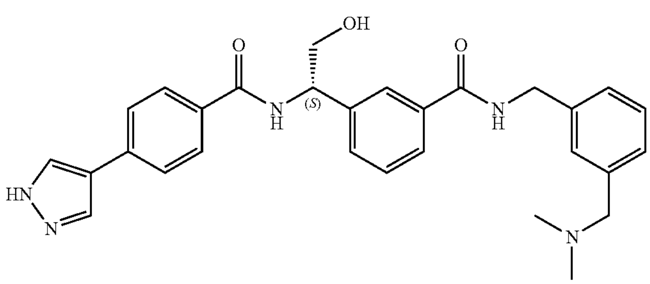 | 498 |
| 83 | 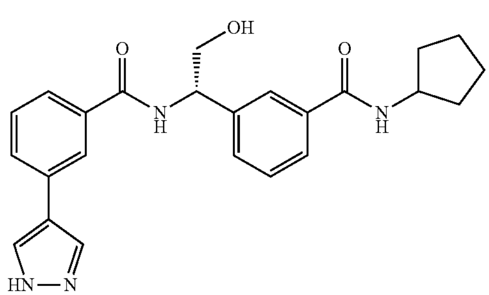 [SMILES: O=C(NC1CCCC1)c1cccc([C@@H](CO)NC(=O)c2cccc(-c3cn[nH]c3)c2)c1] | 419 |

TABLE 1-continued

Non-limiting examples of kinase inhibitor compounds.

| ID | Structure | M + 1 |
| --- | --- | --- |
| 84 | 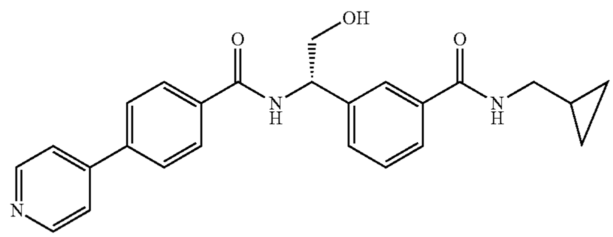 [SMILES: O=C(NCC1CC1)c1cccc([C@@H](CO)NC(=O)c2ccc(-c3ccncc3)cc2)c1] | 416 |
| 85 | 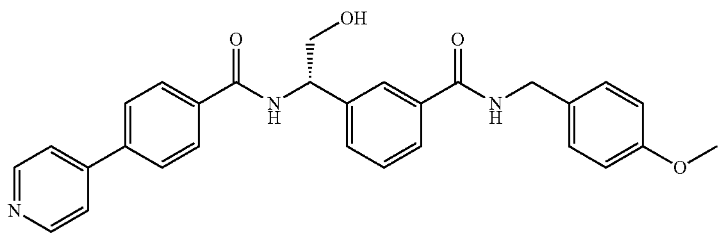 [SMILES: COc1ccc(CNC(=O)c2cccc([C@@H](CO)NC(=O)c3ccc(-c4ccncc4)cc3)c2)cc1] | 482 |
| 86 | 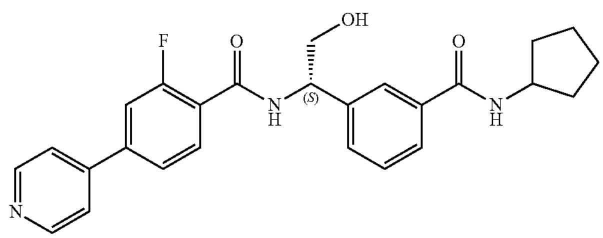 | 448 |
| 87 | 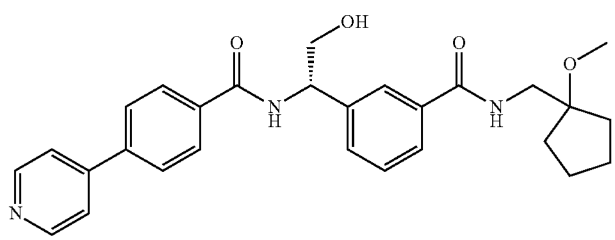 [SMILES: COC1(CNC(=O)c2cccc([C@@H](CO)NC(=O)c3ccc(-c4ccncc4)cc3)c2)CCCC1] | 474 |
| 88 | 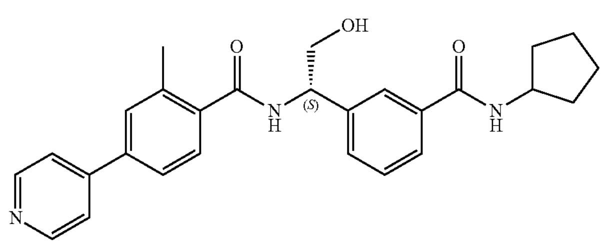 | 444 |
| 89 | 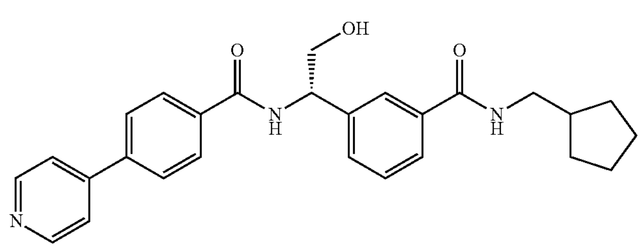 [SMILES: O=C(NCC1CCCC1)c1cccc([C@@H](CO)NC(=O)c2ccc(-c3ccncc3)cc2)c1] | 444 |

TABLE 1-continued

Non-limiting examples of kinase inhibitor compounds.

| ID | Structure | M + 1 |
| --- | --- | --- |
| 90 | 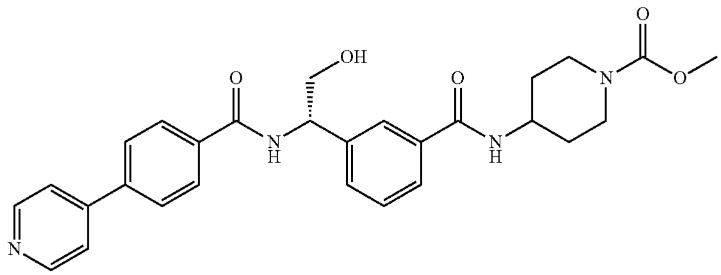 [SMILES: COC(=O)N1CCC(NC(=O)c2cccc([C@@H](CO)NC(=O)c3ccc(-c4ccncc4)cc3)c2)CC1] | 503 |
| 91 | 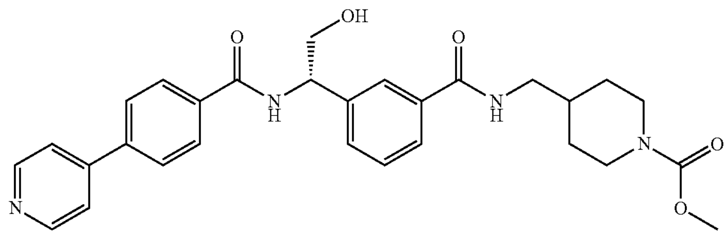 [SMILES: COC(=O)N1CCC(CNC(=O)c2cccc([C@@H](CO)NC(=O)c3ccc(-c4ccncc4)cc3)c2)CC1] | 517 |
| 92 | 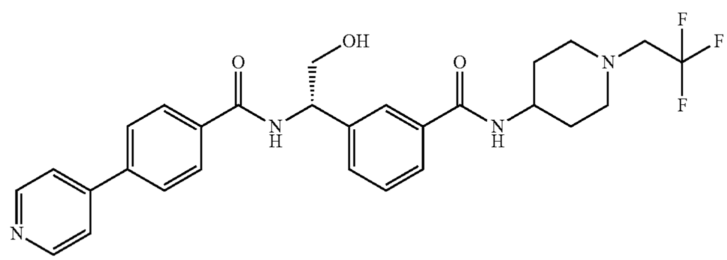 [SMILES: O=C(NC1CCN(CC(F)(F)F)CC1)c1cccc([C@@H](CO)NC(=O)c2ccc(-c3ccncc3)cc2)c1] | 527 |
| 93 | 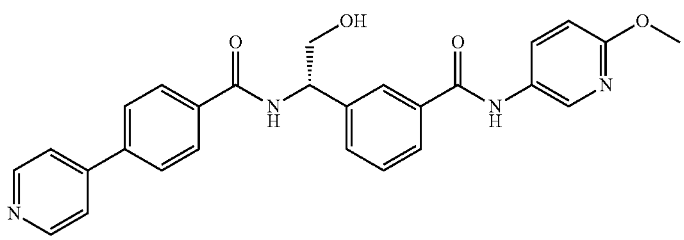 [SMILES: COc1ccc(NC(=O)c2cccc([C@@H](CO)NC(=O)c3ccc(-c4ccncc4)cc3)c2)cn1] | 469 |
| 95 | 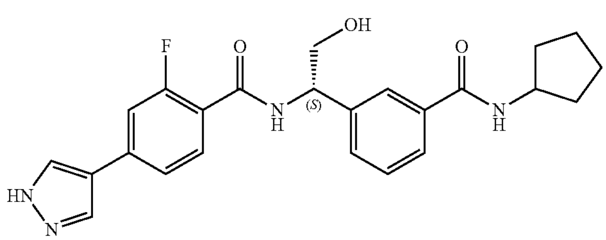 | 437 |
| 96 | 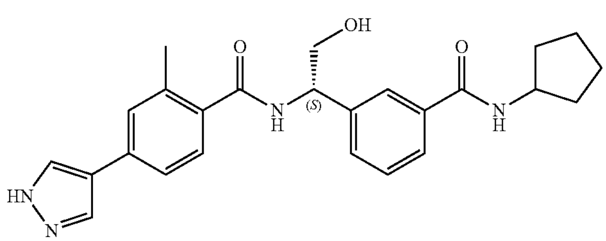 | 433 |

TABLE 1-continued

Non-limiting examples of kinase inhibitor compounds.

| ID | Structure | M + 1 |
|---|---|---|
| 97 | 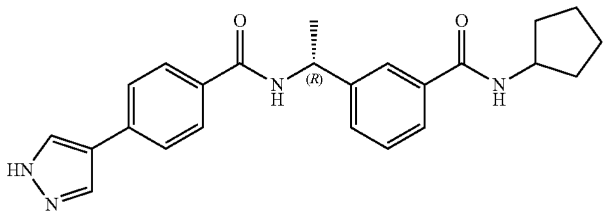 | 403 |
| 98 | 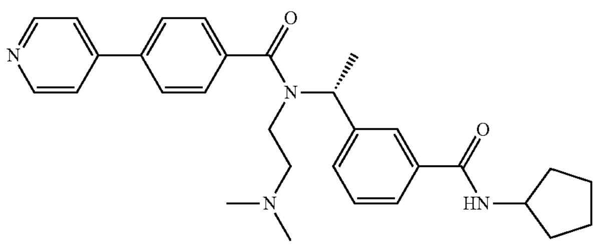 [SMILES: C[C@H](c1cccc(C(=O)NC2CCCC2)c1)N(CCN(C)C)C(=O)c1ccc(-c2ccncc2)cc1] | 485 |
| 100 | 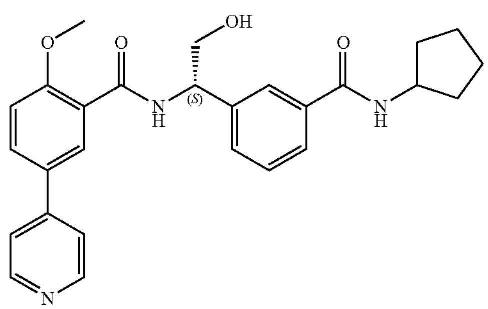 | 460 |
| 101 | 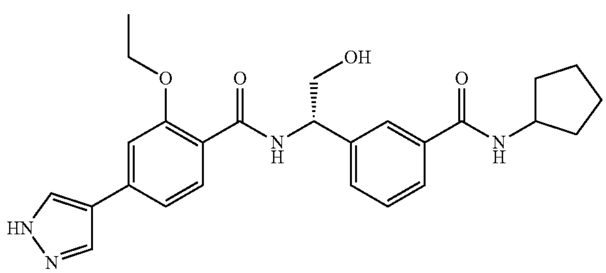 [SMILES: CCOc1cc(-c2cn[nH]c2)ccc1C(=O)N[C@H](CO)c1cccc(C(=O)NC2CCCC2)c1] | 463 |
| 102 | 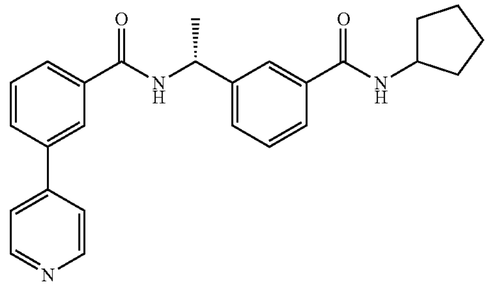 [SMILES: C[C@@H](NC(=O)c1cccc(-c2ccncc2)c1)c1cccc(C(=O)NC2CCCC2)c1] | 414 |

TABLE 1-continued

Non-limiting examples of kinase inhibitor compounds.

| ID | Structure | M + 1 |
|----|-----------|-------|
| 103 | 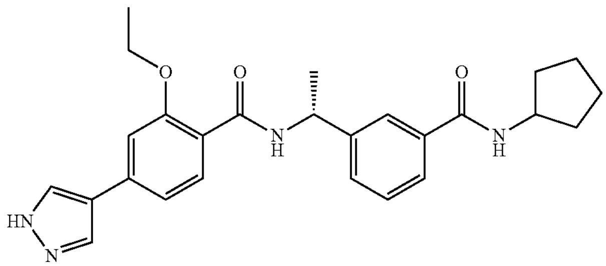 [SMILES: CCOc1cc(-c2cn[nH]c2)ccc1C(=O)N[C@H](C)c1cccc(C(=O)NC2CCCC2)c1] | 447 |
| 104 | 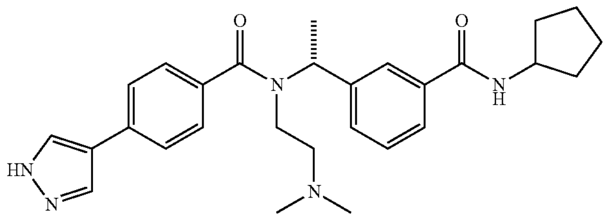 [SMILES: C[C@H](c1cccc(C(=O)NC2CCCC2)c1)N(CCN(C)C)C(=O)c1ccc(-c2cn[nH]c2)cc1] | 474 |
| 105 | 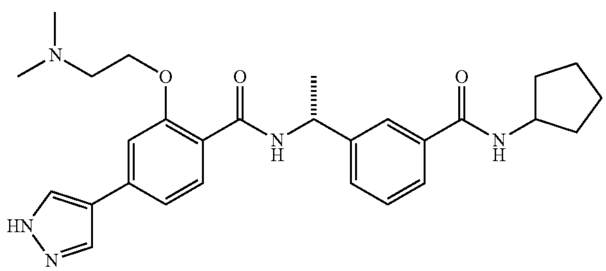 [SMILES: C[C@@H](NC(=O)c1ccc(-c2cn[nH]c2)cc1OCCN(C)C)c1cccc(C(=O)NC2CCCC2)c1] | 490 |
| 106 | 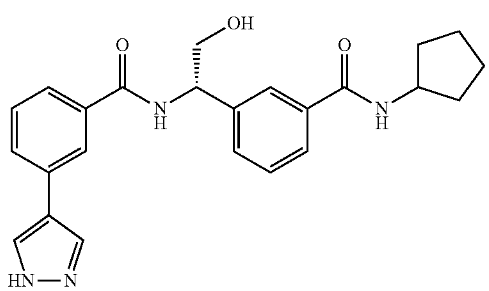 [SMILES: O=C(NC1CCCC1)c1cccc([C@@H](CO)NC(=O)c2cccc(-c3cn[nH]c3)c2)c1] | 419 |
| 110 | 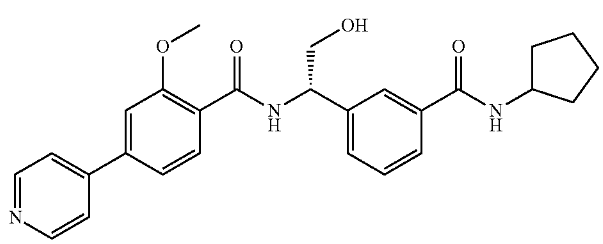 [SMILES: COc1cc(-c2ccncc2)ccc1C(=O)N[C@H](CO)c1cccc(C(=O)NC2CCCC2)c1] | 460 |
| 113 | 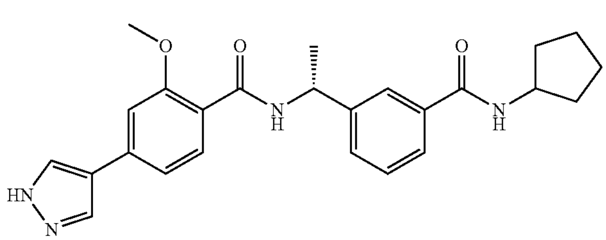 [SMILES: COc1cc(-c2cn[nH]c2)ccc1C(=O)N[C@H](C)c1cccc(C(=O)NC2CCCC2)c1] | 433 |

TABLE 1-continued
Non-limiting examples of kinase inhibitor compounds.
| ID | Structure | M + 1 |
|----|-----------|-------|
| 114 | 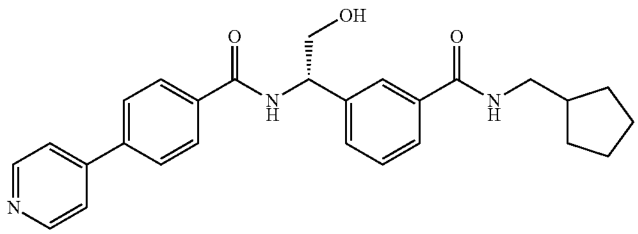 [SMILES: O=C(NCC1CCCC1)c1cccc([C@@H](CO)NC(=O)c2ccc(-c3ccncc3)cc2)c1] | 444 |
| 115 | 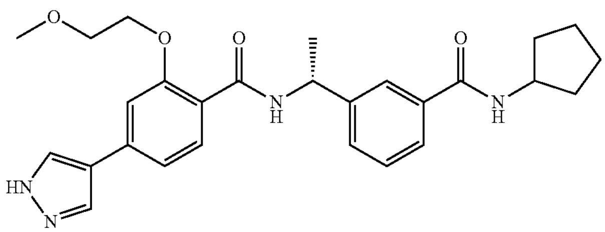 [SMILES: COCCOc1cc(-c2cn[nH]c2)ccc1C(=O)N[C@H](C)c1cccc(C(=O)NC2CCCC2)c1] | 477 |
Unless specified, example compounds with a chiral center represent a racemic mixture of the corresponding R and S enantiomers, and all racemates and isolated enantiomers are within the scope of the invention.
Additional non-limiting examples are:
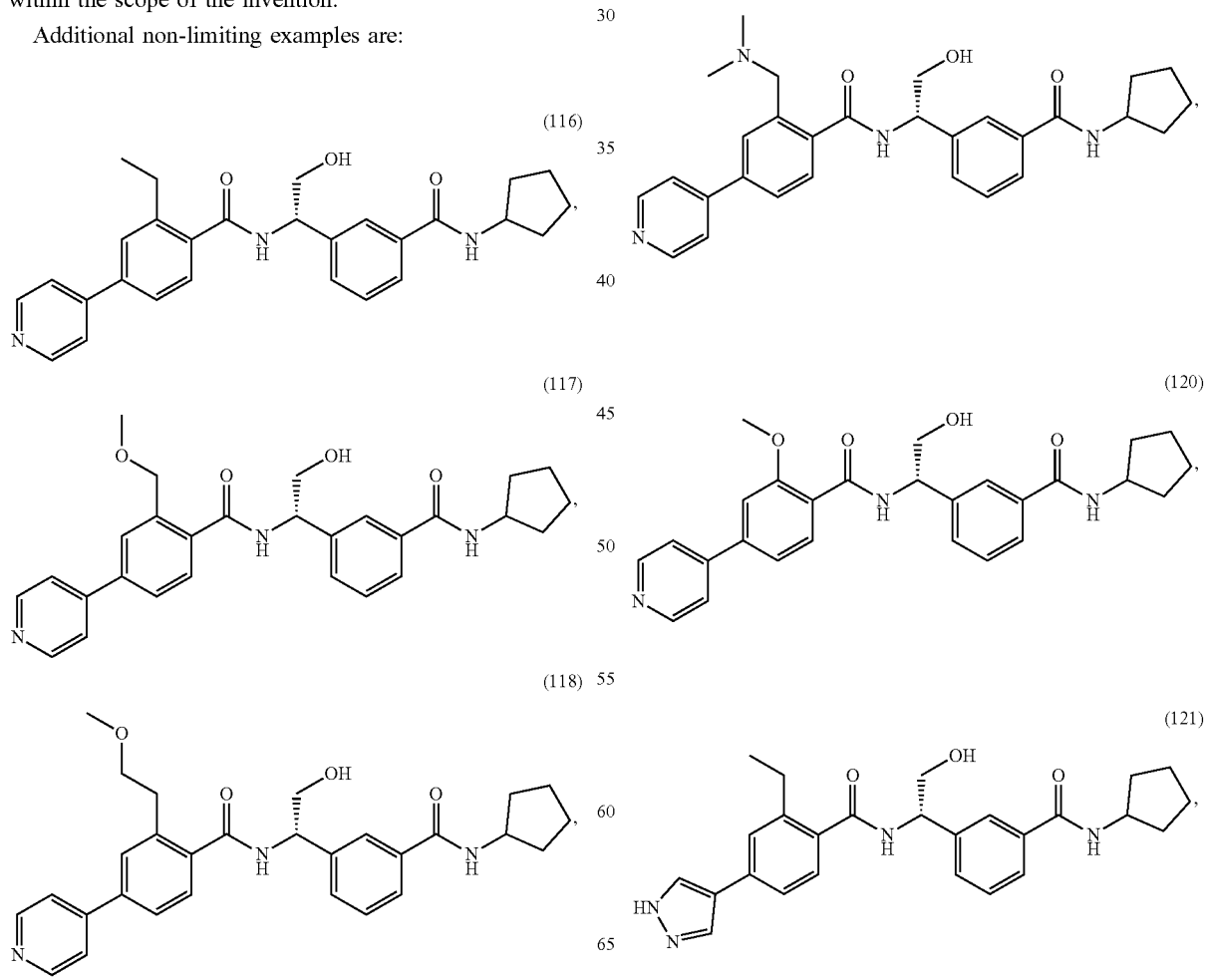

(122)
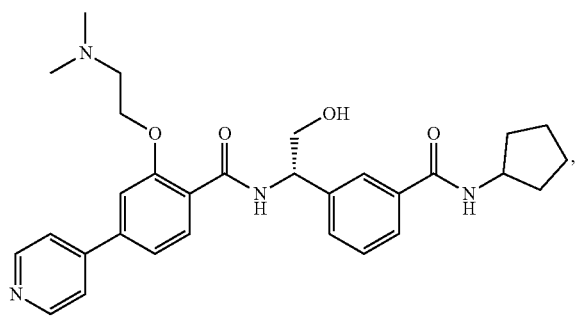

(123)
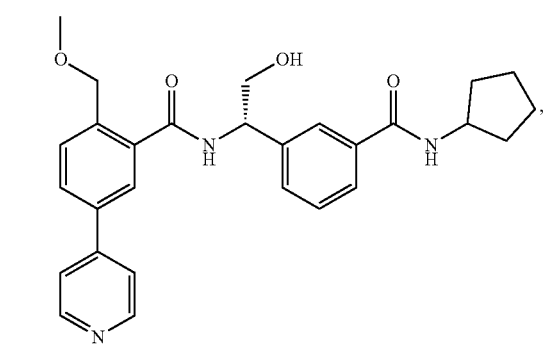

(124)
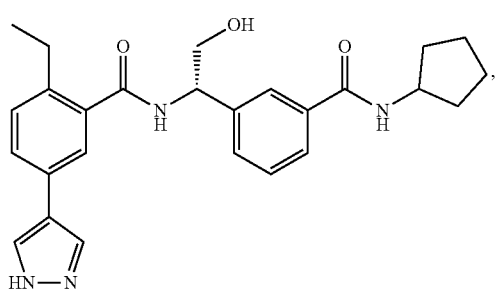

(125)
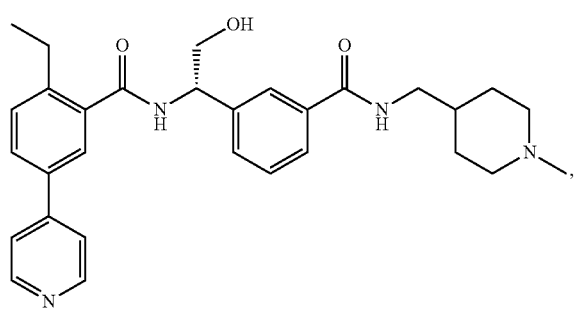

(126)
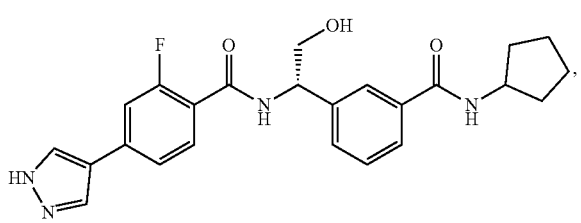

(127)
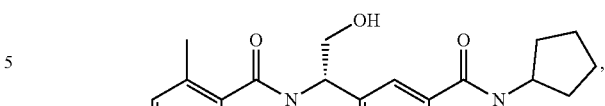

(128)

(129)
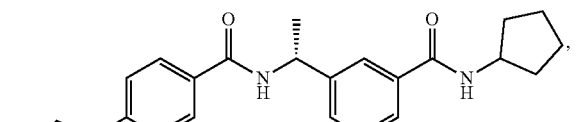

(130)

(131)
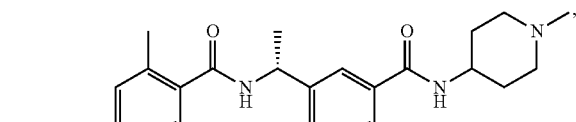

, and (132)

The compounds of the present invention demonstrate improved ROCK enzyme inhibiting activity, inhibition of cancer cell growth and viability, and FLT3-ITD mutant selectivity. In addition, the compounds demonstrate superior pharmacokinetic properties. As points of reference, two previously characterized compounds (i.e., Compounds A and B in Table 2) were analyzed. Additionally, the compounds disclosed herein generally demonstrate greater ROCK inhibition than Ripasudil, a clinical ROCK inhibitor, with relatively weak activity (ROCK1 $IC_{50}$=51 nM and ROCK2 $IC_{50}$=19 nM).

The compounds of the present disclosure may be made by a variety of methods, including standard chemistry. Suitable synthetic routes are depicted in the schemes given below.

The compounds may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I.

Those skilled in the art will recognize if a stereocenter exists in the compounds of Formula I. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

A second aspect of the present disclosure relates to compositions capable of modulating (e.g., inhibiting) the activity of Rho-associated protein kinases (e.g., ROCK-1, ROCK2, or both). The present disclosure also relates to the therapeutic use of such compositions.

A third aspect of the disclosure relates to a method of inhibiting Rho-associated protein kinases, comprising administering to a subject in need thereof an effective amount of the compound of Formula I. In some embodiments, the Rho-associated protein kinase comprises ROCK1.

A fourth aspect of the present disclosure relates to the compound of Formula I, and optionally a pharmaceutically acceptable salt, hydrate, solvate, prodrug, stereoisomer, or tautomer thereof, for use in inhibiting a Rho-associated protein kinase.

A fifth aspect of the present disclosure relates to the use of the compound of Formula I, and optionally a pharmaceutically acceptable salt, hydrate, solvate, prodrug, stereoisomer, or tautomer thereof, in the manufacture of a medicament for inhibiting a Rho-associated protein kinase.

In other embodiments, the Rho-associated protein kinase comprises ROCK2. In yet other embodiments, the Rho-associated protein kinase comprises ROCK1 and ROCK2.

A sixth aspect of the present disclosure relates to a method of treating a disease or improves a condition associated with modulation of Rho-associated protein kinases (e.g., ROCK-1, ROCK2, or both) in a subject in need thereof, comprising administering to the subject in need an effective amount of the compound of Formula I.

A seventh aspect of the present disclosure relates to the compound of Formula I, and optionally a pharmaceutically acceptable salt, hydrate, solvate, prodrug, stereoisomer, or tautomer thereof, for use in treating or preventing a disease associated with Rho-associated protein kinase modulation.

An eighth aspect of the present disclosure relates to the use of the compound of Formula I, and optionally a pharmaceutically acceptable salt, hydrate, solvate, prodrug, stereoisomer, or tautomer thereof, in the manufacture of a medicament for treating or preventing a disease associated with Rho-associated protein kinase modulation or inhibiting a Rho-associated protein kinase.

Non-limiting examples of the diseases associated with modulation of Rho-associated protein kinases include an arterial thrombotic disorder, a cardiovascular disease, a central nervous system disorder, glucose intolerance, a hematologic disease, a hematologic malignant neoplastic disorder, hyperinsulinemia, an infection, an inflammatory or autoimmune disease, insulin resistance, a metabolic syndrome, a neoplastic disease, a neurodegenerative disease, a neurodevelopmental disorder, an ocular disorder, osteoporosis, proliferative diseases or disorders such as cancer, pulmonary arterial hypertension (PAH), type 2 diabetes, a vascular smooth muscle dysfunction, etc.

Non-limiting examples of the conditions associated with modulation of Rho-associated protein kinases include promoting bone formation, and regulating intraocular pressure, etc.

As used herein, the term "cancer" refers to abnormal or unregulated cell growth within a subject. Non-limiting examples of cancer include amoeboid cancer cells, cancer characterized by amoeboid-like migration, breast cancer, diffuse large B-cell lymphoma, gastric cancer (including rhoA-mutated gastric cancers), hepatocellular cancer, leukemias, lung cancer, lymphoma, melanoma, multiple myeloma, ovarian cancer, pancreatic cancer, peripheral T-cell lymphoma (PTCL), prostate cancer, renal cancer, T-cell lymphoma, etc. Gastric cancer includes rhoA-mutated gastric cancers. Non-limiting examples of leukemias include acute myeloid leukemia and acute lymphoblastic leukemia, etc. Non-limiting examples of T-cell lymphoma include angioimmunoblastic, cutaneous T-cell lymphoma, and peripheral T-cell lymphoma, etc. In some embodiments, the disease associated with modulation of Rho-associated protein kinases is selected from the group consisting of: gastric cancer, pancreatic cancer, melanoma, amoeboid cancer cells (cancer characterized by amoeboid-like migration), and combinations thereof. In some implementations, the disease associated with modulation of Rho-associated protein kinases is rhoA-mutated gastric cancers.

Non-limiting examples of the neoplastic diseases include astrocytoma, adenocarcinoma of the kidney, adenocarcinoma of the lung, bladder cancer, blastoma, brain cancer, breast cancer, carcinoma, cancer of the peritoneum, cervical cancer, cholangiocarcinoma, colon cancer, colorectal cancer, endometrial cancer, endometrial carcinoma, esophageal cancer, gallbladder carcinoma, gastric cancer, gastrointestinal cancer, glioblastoma, head and neck cancer, hepatic carcinoma, hepatocellular cancer, hepatoma, kidney cancer, leukemia, liver cancer, lymphoma, melanoma, non-small cell lung cancer, ovarian cancer, pancreatic cancer, pituitary cancer, prostate cancer, salivary gland carcinoma, sarcoma, small-cell king cancer, soft tissue sarcoma, squamous carcinoma of the kidney, squamous carcinoma of the lung, squamous cell cancer, testis cancer, thyroid cancer, uterine carcinoma, and vulval cancer, etc.

Non-limiting examples of ocular disorders include age-related macular degeneration (AMD), choroidal neovascularization (CNV), diabetic macular edema (DME), glaucoma, iris neovascularization, ocular hypertension, retinitis of prematurity (ROP), and uveitis, etc. Non-limiting examples of glaucoma include acute angle-closure glaucoma, congenital glaucoma, neo vascular glaucoma, normal tension glaucoma, pigmentary glaucoma, primary open-angle glaucoma, and secondary glaucoma, etc. In some embodiments, the disease associated with modulation of Rho-associated protein kinases is glaucoma. In some embodiments, the treatment regulates intraocular pressure. In some embodiments, the ocular disorder has an angiogenic component, and the method further comprising administering to the subject an angiogenesis inhibitor. In certain implementations, the ocular disorder is selected from the group consisting of: age related macular degeneration (AMD), choroidal neovascularization (CNV), diabetic macular edema (DME), iris neovascularization, uveitis, neo vascular glaucoma, retinitis of prematurity (ROP), and combinations thereof.

As used herein, the term "neurological disorders" refers to disorders of the nervous system (e.g., the brain and the spinal cord). Non-limiting examples of neurological disorders or neurodegenerative diseases include Alzheimer's disease, amyotrophic lateral sclerosis, attention deficit disorder (ADD), epilepsy, essential tremor, Huntington's Disease, multiple sclerosis, Parkinson's Disease, spinal muscular atrophy, central nervous system trauma caused by tissue injury, and oxidative stress-induced neuronal or axonal degeneration, etc.

Non-limiting examples of neurodevelopmental disorders include Rett syndrome, and Niemann-Pick type C, etc.

In some embodiments, the central nervous system disorder comprises neuronal degeneration, spinal cord injury, or both. In another aspect, the central nervous system disorder is Huntington's disease, Parkinson's Disease, Alzheimer's, Amyotrophic lateral sclerosis (ALS), or multiple sclerosis.

As used herein, the term "inflammation" refers to a host's response to an initial injury or infection. Non-limiting examples of symptoms of inflammation include heat, loss of function, pain, redness, and swelling, etc. Non-limiting examples of causes of inflammation include an upregulation of pro-inflammatory cytokines such as IL-113, and increased expression of the FOXP3 transcription factor, etc.

As used herein, the term "autoimmune disorder" refers to a disorder wherein a host's own immune system responds to tissues and substances occurring naturally in the host's body.

Non-limiting examples of inflammatory or autoimmune diseases include arteriosclerosis, rheumatoid arthritis, spondylitis arthritis, psoriatic arthritis, asthma, atopic dermatitis, cardiovascular inflammation, Crohn's disease, eczema, fibrotic disorders, graft versus host disease (GVHD), inflammatory bowel diseases, multiple sclerosis, psoriasis, renal inflammation, systemic lupus erythematosus (SLE), type-1 diabetes, transplant rejection, etc. Non-limiting examples of fibrotic disorders include liver fibrosis, lung fibrosis, skin, cardiac, and kidney fibrosis, etc. Non-limiting examples of lung fibrosis include idiopathic pulmonary fibrosis. In some embodiments, the disease associated with modulation of Rho-associated protein kinases is selected from the group consisting of: GVHD, fibrotic disorders, and a combination thereof. In some implementations, the fibrotic disorder is liver fibrosis, lung fibrosis, kidney fibrosis, or combinations thereof. In some implementations, the lung fibrosis is idiopathic pulmonary fibrosis.

In some embodiments, the disease associated with modulation of Rho-associated protein kinases is an infection (e.g., infectious diseases or disorders) caused by the invasion of a foreign pathogen (e.g., a bacterium, a fungus, or virus, etc.). In some implementations, the bacterial infection is caused by an E. coli.

As used herein, the term "metabolic disorder" or "metabolic disease" refers to abnormalities in the way that a subject stores energy. Non-limiting examples of metabolic disorders include metabolic syndrome, diabetes, obesity, high blood pressure, and heart failure, etc.

Hematologic diseases primarily affect the blood, and non-limiting examples of hematologic disorders include anemia, lymphoma, and leukemia, etc.

Cardiovascular diseases, disorders, or conditions or vascular smooth muscle dysfunction affect the heart and blood vessels of the subject. Non-limiting examples include atherosclerosis, cardiac hypertrophy, cardiovascular stress, cerebral ischemia, cerebral vasospasm, chronic ischemia, erectile dysfunction, heart failure, hypertension, infarction-reperfusion injury, ocular hypertension, pressure overload, peripheral artery disease, and restenosis, etc.

In some implementations, the disease is selected from the group consisting of: ocular disorder, gastric cancer, pancreatic cancer, melanoma, graft versus host disease, liver fibrosis, myelofibrosis (MF), myelofibrosis with myeloid metaplasia (MMM), chronic idiopathic myelofibrosis (UIMF), a hematologic malignant neoplastic disorder is characterized by deregulated FLT3 receptor tyrosine kinase activity, and combinations thereof.

In certain implementations, the disease is associated with upregulation of Rho kinase-signaling pathways.

In one embodiment, the arterial thrombotic disorder is platelet aggregation, leukocyte aggregation, or both.

In some embodiments, the compound of Formula I is administered in an effective amount to treat the disease or disorder, prevent the disease or disorder, or prevent the development thereof in the subject.

Administration of the compound of Formula I can be accomplished via any mode of administration for therapeutic agents. Non-limiting examples of the modes include systemic administration or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, all using forms well known to those skilled in the pharmaceutical arts.

Illustrative pharmaceutical compositions are tablets and gelatin capsules comprising a Compound of the Disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles, and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include, but are not limited to polyvinylpyrrolidone, pyran copolymer, polyhydroxypropylmethacryl-amidephenol, polyhydroxyethyl-aspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates, and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections, and infusions. Injectables can be prepared in conventional forms, either as liquid solutions or suspensions or solid forms suitable for dissolving in liquid prior to injection.

Another aspect of the disclosure relates to a pharmaceutical composition comprising a disclosed compound and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

Without wishing to be bound by any particular theory, the compounds of the present disclosure can inhibit Rho-associated protein kinase such as ROCK-1 and ROCK-2.

EXAMPLES

The disclosure is further illustrated by the following examples and synthesis examples, that are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1. Synthesis of Compound ID #1

ID#1

Step 1.

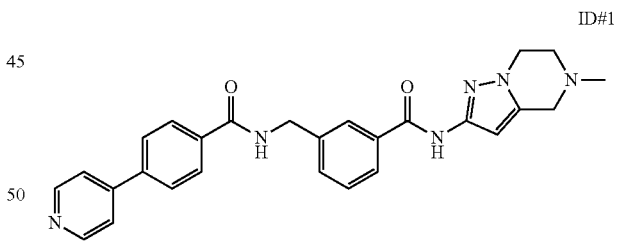

1A

To a solution of 4-(pyridin-4-yl)benzoic acid (100 mg, 0.50 mmol) and methyl 3-(aminomethyl)benzoate (99 mg, 0.6 mmol) in DMF were added diisopropylethylamine (DIEA, 0.26 mL, 1.5 mmol) and 1-[Bis(dimethylamino)methylene]-1H-1,2,3-triazolo[4,5-b]pyridinium 3-oxid hexafluorophosphate (HATU, 247 mg, 0.65 mmol). The reaction was stirred at room temperature for 2 hrs and diluted with water. The mixture was concentrated and purified by C-18 column chromatography to give 1A (141 mg).
Step 2.

To a solution of 4-(pyridin-4-yl)benzoic acid (50 mg, 0.25 mmol) and methyl 3-((1S)-1-amino-2-hydroxyethyl)benzoate HCl salt (75 mg, 0.3 mmol) in DMF were added diisopropylethylamine (DIEA, 0.13 mL, 0.75 mmol) and HATU (123 mg, 0.32 mmol). The reaction was stirred at room temperature for 2 hrs and diluted with water. The mixture was concentrated and purified by C-18 column chromatography to give 2A (68 mg).
Step 2.

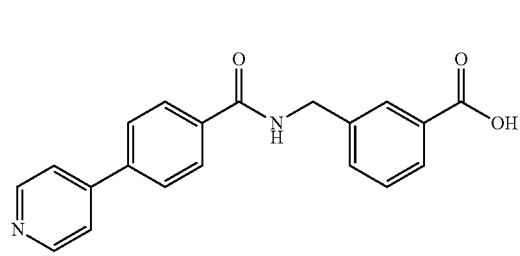

1

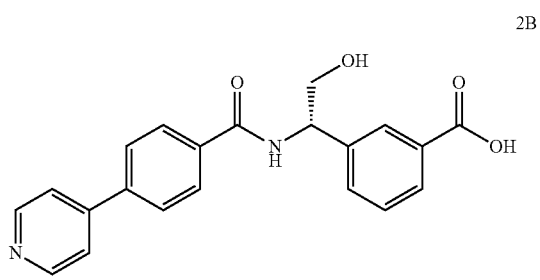

2B

To a solution of 1A (141 mg, 0.41 mmol) in THF was added LiOH solution (1 M, 2.0 mL). The reaction was stirred at room temperature overnight and neutralized with HCl solution. The mixture was concentrated and purified by C-18 column chromatography to give 1B (97 mg).
Step 3.

To a solution of 1B (7 mg, 0.02 mmol) and 5-methyl-4,5,6,7-tetrahydropyrazolo[1,5-a]pyrazin-2-amine (6 mg, 0.04 mmol) in DMF were added diisopropylethylamine (DIEA, 0.007 mL, 0.04 mmol) and HATU (15 mg, 0.04 mmol). The reaction was stirred at room temperature for 2 hrs and diluted with water. The mixture was concentrated and purified by C-18 column chromatography to give ID #1 (8 mg).

Example 2. Synthesis of Compound ID #10

To a solution of 1A (68 mg, 0.17 mmol) in THF was added LiOH solution (1 M, 0.85 mL). The reaction was stirred at room temperature overnight and neutralized with HCl solution. The mixture was concentrated and purified by C-18 column chromatography to give 2B (40 mg).
Step 3.

To a solution of 2B (5 mg, 0.014 mmol) and cyclopentylamine (3 mg, 0.035 mmol) in DMF were added diisopropylethylamine (DIEA, 5 microL, 0.028 mmol) and HATU (7 mg, 0.018 mmol). The reaction was stirred at room temperature for 2 hrs and diluted with water. The mixture was concentrated and purified by C-18 column chromatography to give ID #10 (5 mg).

Example 3. Synthesis of Compound ID #3

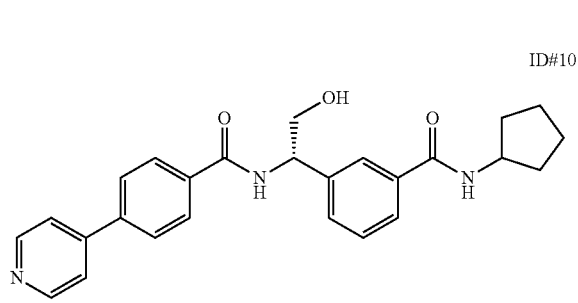 [SMILES: O=C(NC1CCCC1)c1cccc([C@@H](CO)NC(=O)c2ccc(-c3ccncc3)cc2)c1]

ID#10

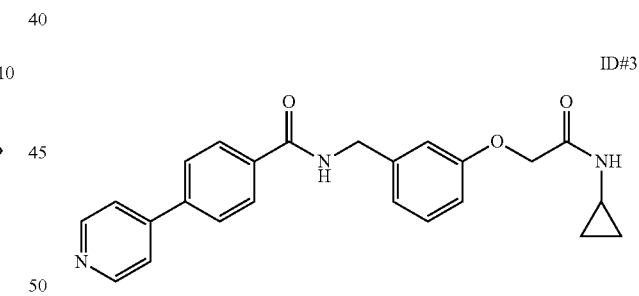

ID#3

Step 1.

Step 1.

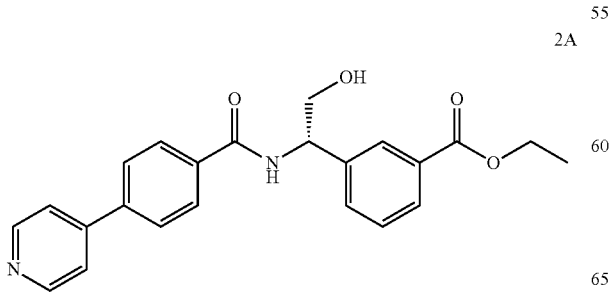

2A

3A

To a solution of 4-(pyridin-4-yl)benzoic acid (50 mg, 0.25 mmol) and 3-(aminomethyl)phenol (37 mg, 0.3 mmol) in DMF were added diisopropylethylamine (DIEA, 0.13 mL, 0.75 mmol) and HATU (123 mg, 0.32 mmol). The reaction was stirred at room temperature for 2 hrs and diluted with water. The mixture was concentrated and purified by C-18 column chromatography to give 3A (62 mg).

Step 2.

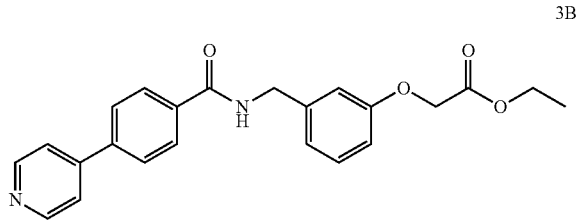 [SMILES: CCOC(=O)COc1cccc(CNC(=O)c2ccc(-c3ccncc3)cc2)c1]

3B

To a mixture of 3A (62 mg, 0.20 mmol) and ethyl chloroacetate (25 mg, 0.20 mmol) in acetonitrile was added potassium carbonate (33 mg, 0.24 mmol). The reaction was heated to 55 C, stirred overnight, filtered and concentrated. The residue was purified by C-18 column chromatography to give 3B (55 mg).

Step 3.

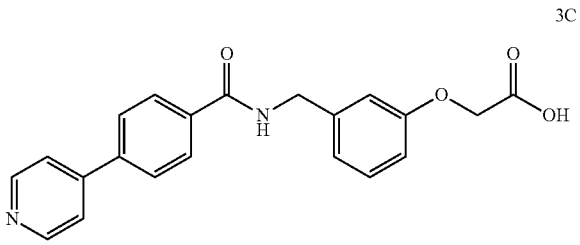 [SMILES: O=C(O)COc1cccc(CNC(=O)c2ccc(-c3ccncc3)cc2)c1]

3C

To a solution of 3B (55 mg, 0.14 mmol) in THF was added LiOH solution (1 M, 0.7 mL). The reaction was stirred at room temperature overnight and neutralized with HCl solution. The mixture was concentrated and purified by C-18 column chromatography to give 3C (50 mg).

Step 4.

To a solution of 3C (10 mg, 0.028 mmol) and cyclopropylamine (5 mg, 0.084 mmol) in DMF was added HATU (13 mg, 0.034 mmol). The reaction was stirred at room temperature for 2 hrs and diluted with water. The mixture was concentrated and purified by C-18 column chromatography to give ID #3 (10 mg).

Example 4—ROCK1 and ROCK2 Kinase Inhibition Assays

The following assay protocol is for measuring the phosphorylation of a peptide substrate (FAM-KKLRRTLSVA-OH wherein FAM is carboxyfluorescein). The peptide is >98% purity by Capillary Electrophoresis. The peptide is phosphorylated by the protein kinase ROCK1 or ROCK2. The ROCK1 or ROCK2 enzyme, substrate, and cofactors (ATP and $Mg^{2+}$) are combined in a well of a microtiter plate and incubated for 3 hours at 25° C. in the presence or absence of an inhibitor compound. At the end of the incubation, the reaction is quenched by the addition of an EDTA-containing buffer. The substrate and product are separated and quantified electrophoretically using the microfluidic-based LABCHIP® 3000 Drug Discovery System from Caliper Life Sciences (Hopkinton, Mass.).

The components of the assay mixture are:
100 mM HEPES, pH 7.5
0.1% BSA
0.01% Triton X-100
1 mM DTT
10 mM $MgCl_2$
10 μM Sodium Orthovanadate
10 LM Beta-Glycerophosphate
5 μM ATP (for ROCK1) or 7 μM ATP (for ROCK2)
1% DMSO (from compound)
1.25 μM FAM-KKLRRTLSVA-OH
3 nM ROCK1 or 2.5 nM ROCK2 enzyme Substrate and product peptides present in each sample are separated electrophoretically using the LABCHIP® 3000 capillary electrophoresis instrument. As substrate and product peptides are separated two peaks of fluorescence are observed. Change in the relative fluorescence intensity of the substrate and product peaks is the parameter measured reflecting enzyme activity. Capillary electrophoregramms (RDA acquisition files) are analyzed using HTS Well Analyzer software (Caliper Life Sciences, Hopkinton, Mass.). The kinase activity in each sample is determined as the product to sum ratio (PSR): P/(S+P), where P is the peak height of the product peptide and S is the peak height of the substrate peptide. For each compound, enzyme activity is measured at various concentrations (12 concentrations of compound spaced by 3× dilution intervals). Negative control samples (0%-inhibition in the absence of inhibitor) and positive control samples (100%-inhibition in the presence of 20 mM EDTA) are assembled in replicates of four and are used to calculate %-inhibition values for each compound at each concentration. Percent inhibition (Pinh) is determined using the following equation:

Pinh=(PSRO %–PSRinh)/(PSRO %–PSR100%)*100 where PSRinh is the product sum ratio in the presence of inhibitor, PSRO % is the average product sum ratio in the absence of inhibitor, and PSR100% is the average product sum ratio in 100%-inhibition control samples. The $IC_{50}$ values of inhibitors are determined by fitting the inhibition curves (Pinh versus inhibitor concentration) by the 4-parameter sigmoidal dose-response model using XLfit 4 software (IBDS).

This assay can be used to test the activity of each of the exemplary compounds identified in Table 2. It is expected that each of these compounds will demonstrate inhibition of the protein kinase ROCK1 and/or ROCK2.

Example 5. Cell Viability Assay

Cell viability in the presence of varying concentrations of the above listed compounds at different time points was used to assess cytotoxicity and the effect of the compounds on cell proliferation. $IC_{50}$ (or percent activity) data for the compounds of the present invention in K562 or MV411 cell lines are summarized in Table 2.

Cell Viability Assay—

Cell viability was measured by the CELLTITER-GlO® cell viability assay from Promega (Madison, Wis.). The CELLTITER-GlO Luminescent Cell Viability Assay is a homogeneous method to determine the number of viable cells in culture based on quantitation of the ATP present, which signals the presence of metabolically active cells. Following treatment, CELLTITER-GlO® is added to treatment wells and incubated at 37° C. Luminescence values were measured at using a Molecular Devices Spectramax microplate reader.

Experimental Design

Single Agent Studies—

Cells were grown to 70% confluency, trypsinized, counted, and seeded in 96 well flat-bottom plates at a final concentration of $2.5 \times 10^3$-$5 \times 10^3$ cells/well (Day 0). Cells were allowed to incubate in growth media for 24 hours. Treatment with the test agents or standard agents began on Day 1 and continued for 72 hours. At the 72-hour time point, treatment containing media was removed. Viable cell numbers were quantified by the CELLTITER-GLO® cell viability assay as described above. Results from these studies were used to calculate an $IC_{50}$ value (concentration of drug that inhibits cell growth by 50 percent of control) for each compound.

Data Collection—

For single agent and combination studies, data from each experiment was collected and expressed as % Cell Growth using the following calculation:

% Cell Growth=$(f_{test}/f_{vehicle}) \times 100$

Where $f_{test}$ is the luminescence of the tested sample, and $f_{vehicle}$ is the luminescence of the vehicle in which the drug is dissolved. Dose response graphs and $IC_{50}$ values were generated using Prism 6 software (GraphPad) using the following equation:

$Y=(Top-Bottom)/(1+10^{((logIC50-X)-HillSlope)})$

Where X is the logarithm of the concentration and Y is the response. Y starts at the Bottom and goes to the Top with a sigmoid shape.

Example 6. ROCK1 and ROCK2 Kinase Inhibition and Cell Viability Assay Results

In general, kinases regulate many important cellular activities including cell growth, signaling, metabolism, etc. Different kinases have distinct functions and pathways. Selective inhibition of ROCK1 and ROCK2 avoids off target activity that may cause undesired side effects such as toxicity.

The protocols outlined in Examples 5 and 6 were followed to test ROCK1 and ROCK2 kinase inhibition and cancer cell viability with compounds from Table 1. As shown in Table 2, the compounds demonstrated inhibition of the ROCK1 and ROCK2 kinases and growth of cancer cells.

The experiments also evaluated the selectivity of the compounds for inhibiting growth of cancer cells carrying a mutation in the Flt3 gene. The MV411 cell line expresses the mutant allele of Flt3 with internal tandem duplications (ITD) of the gene. See Quentmeier et al., "FLT3 Mutations in Acute Myeloid Leukemia Cell Lines," Leukemia 17(1), 2003, 120-124. K562 is a chronic myeloid leukemia cell line that does not express FLT3 protein. See Grafone et al., "Monitoring of FLT3 Phosphorylation Status and Its Response to Drugs By Flow Cytometry in AML Blast Cells," Hematol Oncol. 26(3), 2008, 159-166. Compounds demonstrating FLT3-ITD$^+$ selectivity are identified by a greater K562/MV411 ratio in Table 2.

FLT3/ITD gene mutations have been detected by polymerase chain reaction (PCR) in acute myeloid leukemia (AML), acute lymphocytic leukemia (ALL), chronic myelogenous leukemia (CML) in chronic phase (CML-CP), CML cases in blast crisis (CML-BC), chronic lymphatic leukemia (CLL), myelodysplastic syndrome (MDS), chronic myelomonocytic leukemia (CMML), multiple myeloma (MM) cases and non-Hodgkin's lymphoma (NHL) with marrow infiltration. Patients with ITD-FLT3$^+$ acute myeloid leukemia (AML) experience an extremely poor prognosis.

Surprisingly, many of the compounds demonstrated greater efficacy with the MV11 cells than with the K562 cells, suggesting that these compounds could be used to effectively treat FLT3-ITD$^+$ cancers including ITD-FLT3$^+$ AML.

TABLE 2

ROCK1 and ROCK2 kinase inhibition and cell viability

| Compound ID | ROCK1 $IC_{50}$ (nM) | ROCK2 $IC_{50}$ (nM) | K562* (μM) | MV411* (μM) | FLT3-ITD$^+$ Selectivity (K562/ MV411) |
|---|---|---|---|---|---|
| 1 | 11.6 | 6.0 | >100 | 8.9 | >11 |
| 2 | 2.8 | 2.8 | | | |
| 3 | 38.8 | 14.2 | >100 | 2.4 | >42 |
| 4 | 56.1 | 18.9 | | | |
| 5 | 21.7 | 6.7 | >100 | 1.5 | >68 |
| 6 | | 1.2 | 8.0 | 0.2 | 40 |
| 7 | | 1.5 | 20.4 | 0.06 | 333 |
| 8 | | 1.3 | | | |
| 9 | | 1.7 | 35 | 0.8 | 47 |
| 10 | 4.8 | 0.87 | 17 | 0.17 | 100 |
| 11 | | 2.7 | >100 | 12.3 | >8 |
| 12 | | 1.8 | >100 | 0.54 | >187 |
| 13 | | 1.7 | 27 | 3.0 | 9 |
| 14 | | 1.6 | 48 | 0.09 | 532 |
| 15 | | 9 | >100 | 4.0 | >25 |
| 16 | | 3.6 | 30 | 1.5 | 20 |
| 17 | | 22.5 | >100 | 13.5 | >7 |
| 18 | | 19.6 | >100 | 15.9 | >6 |
| 19 | | | 44 | 13.2 | 3 |
| 20 | | 1.2 | 16 | 0.01 | 1585 |
| 21 | 3.1 | 1.0 | 39 | 2.1 | 19 |
| 22 | | 0.57 | >100 | 3.8 | >27 |
| 23 | | 0.3 | 56 | 0.09 | 632 |
| 24 | 2.2 | 1.2 | 28 | 1.5 | 19 |
| 25 | | 18.9 | | | |
| 26 | 3.7 | 1.5 | 48 | 7.4 | 6 |
| 27 | | 0.39 | 25 | 4.4 | 6 |
| 28 | 1.6 | 1.1 | >100 | 2.4 | >42 |
| 29 | | | | 65.1 | |
| 30 | 2.9 | 1.5 | | | |
| 31 | 2.1 | 1.0 | | | |
| 32 | 1.4 | 0.9 | 37 | 0.06 | 619 |
| 33 | | 0.38 | | | |
| 34 | | 0.69 | | | |
| 35 | 1.6 | 1.2 | | | |
| 36 | | 1.2 | | | |
| 37 | | 3.0 | | 1.7 | |
| 38 | | 56 | | 20 | |
| 39 | | 0.3 | 9.4 | 0.01 | 940 |
| 40 | | 0.41 | | 3.4 | |
| 41 | | 6.53 | | | |
| 42 | | 72.6 | | | |
| 43 | | 9.3 | | | |
| 44 | | 240 | | | |
| 45 | | 257 | | | |
| 46 | | 1.88 | 11 | 0.09 | 122 |
| 47 | | 0.54 | 36 | 0.10 | 360 |
| 48 | | 1.01 | >100 | 0.44 | >230 |
| 49 | | 0.30 | >100 | 0.02 | >5050 |
| 50 | | 0.33 | >100 | 0.10 | >1010 |
| 51 | | 4.38 | >100 | 1.45 | >70 |
| 52 | | 0.61 | >100 | 0.12 | >842 |
| 53 | | 0.66 | >100 | 0.22 | >459 |
| 54 | | 0.54 | >100 | 0.07 | >1443 |
| 55 | | 0.47 | >100 | 0.12 | >842 |
| 56 | | 0.31 | >100 | 0.09 | >1122 |
| 57 | | 0.63 | >100 | 0.09 | >1122 |
| 58 | | 0.44 | >100 | 0.04 | >2525 |
| 59 | | 0.46 | >100 | 0.28 | >361 |
| 60 | | 0.53 | >100 | 0.04 | >2525 |
| 61 | | 2.12 | >100 | 2.5 | >40 |
| 62 | | 2.85 | 65 | 1.03 | 63 |
| 63 | 14 | 4.1 | >100 | 0.14 | >721 |

TABLE 2-continued

ROCK1 and ROCK2 kinase inhibition and cell viability

| Compound ID | ROCK1 IC$_{50}$ (nM) | ROCK2 IC$_{50}$ (nM) | K562* (µM) | MV411* (µM) | FLT3-ITD$^+$ Selectivity (K562/MV411) |
|---|---|---|---|---|---|
| 64 | 16.8 | 5.2 | >100 | 1.49 | >68 |
| 65 |  | 0.6 | 28 | 0.07 | 393 |
| 66 |  | 0.6 | 36 | 0.13 | 279 |
| 67 |  | 9.1 | 41 | 2.67 | 15 |
| 68 |  | 104 |  |  |  |
| 69 |  | 0.7 | 52 | 0.15 | 350 |
| 70 | 3.84 | 0.9 | 85 | 0.31 | 275 |
| 71 |  | 9.0 | 34 | 0.91 | 37 |
| 72 |  | 0.5 | 89 | 0.10 | 891 |
| 73 |  | 0.6 | 27 | 0.08 | 337 |
| 74 |  | 27.1 | 74 | 9.12 | 8 |
| 75 |  | 0.5 | 33 | 0.16 | 207 |
| 76 | 2.4 | 1.2 | 58 | 0.48 | 120 |
| 77 | 2.1 | 0.94 | >100 | 0.02 | >5000 |
| 78 | 1.7 | 0.57 | >100 | 0.03 | >3333 |
| 79 | 1.9 | 0.68 | >100 | 0.03 | >3333 |
| 80 | 1.7 | 0.51 | 85 | 0.09 | 935 |
| 81 | 3.2 | 0.88 | >100 | 0.12 | 833 |
| 82 | 2.0 | 0.65 | >100 | 0.61 | 166 |
| 83 |  | 20 | >100 | 3.6 | >28 |
| 84 |  | 1.2 | 33 | 0.27 | 123 |
| 85 |  | 0.6 | 33 | 0.09 | 368 |
| 86 |  | 2.7 | >100 | 1.7 | >58 |
| 87 |  | 0.8 | 23 | 0.27 | 85 |
| 88 |  | 7.5 | >100 | 8.5 | >12 |
| 89 |  | 0.72 | 66 | 0.28 | 236 |
| 90 |  | 0.64 | >100 | 0.02 | >5050 |
| 91 |  | 0.57 | >100 | 0.03 | >4040 |
| 92 |  | 0.68 | >100 | 0.03 | >3061 |
| 93 |  | 0.51 | 85 | 0.09 | 935 |
| 94 |  | 0.65 | >100 | 0.61 | 166 |
| 95 |  | 2.34 | 76 | 0.89 | 86 |
| 96 |  | 53.1 | 101 | 0.71 | 142 |
| 97 |  | 0.74 | 17 | 0.11 | 154 |
| 98 |  | 0.23 |  |  |  |
| 101 |  | 0.25 | 15 | 0.08 | 194 |
| 103 | 1.51 | 0.52 | 8 | 0.14 | 59 |
| 106 |  | 20 |  |  |  |
| 110 |  | 2.5 | >100 | 0.41 | 246 |
| 115 | 3.91 | 1.02 | 45 | 0.24 | 188 |
| Compound A** | 3.3 | 2.8 | 0.8 | 0.7 | 1 |
| Compound B*** | 9.9 | 8.7 | 20 | 1.3 | 15 |

*MV411 is ITD-FLT3$^+$, and K562 does not express ITD-FLT3. Rho-associated kinase may be manipulated for the treatment of ITD-FLT3$^+$ AML as reported in Onish et at., "Internal Tandem Duplication Mutations in FLT3 Gene Augment Chemotaxis to Cxcl12 Protein by Blocking the Down-regulation of the Rho-associated Kinase via the Cxcl12/Cxcr4 Signaling Axis," J. Biol. Chem. 289 (45), 2014, 31053-31065.
**Compound A was a positive control (shown below and is described by Schirok et al., "Design and Synthesis of Potent and Selective Azaindole-Based Rho Kinase (ROCK) Inhibitors," ChemMedChem 3, 2008, 1893-1904).

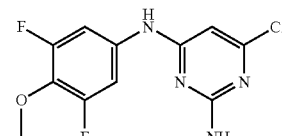

Compound A

*** Compound B was another positive control (shown below and is described by Cook et al., "RHO KINASE INHIBITORS" U.S. Pat. No. 8,697,911).

Compound B

Example 7. Pharmacokinetic Activity

Compounds were individually and accurately weighed out to produce a stock solution in Dimethyl-sulfoxide (DMSO) at a concentration of 2 mg/mL and stored at −20° C. From the stock solution, a working stock was prepared by diluting it in Methanol-Water 50:50 (v/v) at 20 µg/mL for calibration curve preparation and stored at 4° C. Standards used for quantitation and quality control samples (QCs) were prepared on the same day of sample processing using blank plasma obtained from non-treated mice. For each analyte, standards were prepared through serial dilutions of the working stock at concentrations of 0.1, 0.5, 1.0, 10, 50, 100, 500, and 1000 ng/mL; QCs were prepared at intermediate concentrations of 0.75, 7.5, 75, and 750 ng/mL. Plasma samples were stored at −80° C. until ready for analysis and then placed on ice for thawing. An aliquot of 20 L samples, standards, or QCs, were transferred into a 96-well extraction plate according to a pre-defined layout. An appropriate volume of Methanol-Formic Acid 99.9-0.1 containing internal standard (Verapamil at 25 ng/mL) was added to each well and the samples were extracted under vacuum. Eluent was then transferred into a LCMS plate for analysis using a suitable column for separation and MRM detection. Concentration of analytes was calculated based on the calibration curve and analyzed for pharmacokinetic parameters by using Non-compartmental analysis (NCA). Parameters such as Cmax, Tmax, half-life, AUC(0-last), AUC(0-∞), volume of distribution (Vss), and clearance (Cl/F) were reported.

TABLE 3

Pharmacokinetic activity of 7, 10 and 36 in mice

| PK parameters | 7 | | 10 | | 36 | |
|---|---|---|---|---|---|---|
|  | IV - 1 mg/kg | PO - 5 mg/kg | IV - 1 mg/kg | PO - 5 mg/kg | IV - 1 mg/kg | PO - 5 mg/kg |
| R-sq | 0.88 | 0.47 | 0.90 | 0.93 | 0.72 | 1.00 |
| Half-life (hr) | 6.43 | N/A | 3.86 | 2.32 | 2.59 | 2.96 |
| Tmax (hr) | 0.25 | 1.00 | 0.25 | 1.00 | 0.25 | 1.00 |
| Cmax (ng/mL) | 190.02 | 5.30 | 4179.80 | 13132.60 | 4344.78 | 2501.58 |

TABLE 3-continued

Pharmacokinetic activity of 7, 10 and 36 in mice

| | 7 | | 10 | | 36 | |
|---|---|---|---|---|---|---|
| PK parameters | IV - 1 mg/kg | PO - 5 mg/kg | IV - 1 mg/kg | PO - 5 mg/kg | IV - 1 mg/kg | PO - 5 mg/kg |
| C0 (ng/mL) | 411.06 | | 7001.17 | | 5905.04 | |
| $AUC_{0-8}$ (hr*ng/mL) | 234.71 | 81.60 | 5346.72 | 51413.43 | 5854.70 | 8887.72 |
| $AUC_{0\text{-}inf}$ (hr*ng/mL) | 242.69 | N/A | 5367.78 | 51459.94 | 6067.28 | 10491.23 |
| AUC % Extrap | 3.29 | N/A | 0.39 | 0.09 | 0.35 | 0.33 |
| Vss (L/kg) | 16.31 | | 0.32 | | 0.27 | |
| Vz/F obs (L/kg) | | N/A | | 0.30 | | 2.04 |
| Cl/F obs (L/hr/kg) | 4.12 | N/A | 0.17 | 0.09 | 0.16 | 0.48 |
| % $F^a$ | | N/A | | >100 | | 34.58 |

Unless defined otherwise, all technical and scientific terms herein have the same meaning as commonly understood by one of ordinary skill in the art to which this invention belongs. All publications, patents, and patent publications cited are incorporated by reference herein in their entirety for all purposes.

It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

What is claimed is:

1. A compound of Formula (I):

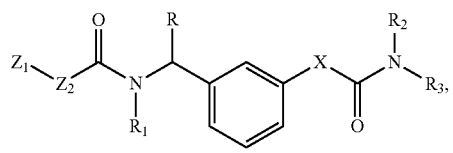

I wherein:
$Z_1$ is pyridine or pyrazole, wherein the pyridine or pyrazole is optionally substituted with H, halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, -C3-C7 cycloalkyl, or a 3- to 10-membered heterocycle, and wherein
  the —C1-C6 alkyl, aryl, -C3-C7 cycloalkyl, or 3- to 10-membered heterocycle is optionally substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, or —C3-C7 cycloalkyl;
$Z_2$ is phenyl, naphthyl, or C5-C10 membered heterocycle, wherein the phenyl, naphthyl, or C5-C10 membered heterocycle is optionally substituted with H, halo, —OH, —CN, —COOR', —OR', —OR'OR", —O(CH$_2$)$_2$NR'R", —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, -C3-C7 cycloalkyl, or a 3- to 10-membered heterocycle, and wherein
  the —C1-C6 alkyl, aryl, -C3-C7 cycloalkyl, or 3- to 10-membered heterocycle is optionally substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", —S(O)$_2$R', guanidino, nitro, nitroso, —C1-C6 alkyl, aryl, or —C3-C7cycloalkyl;
$R_1$ is H, -C1-C6 alkyl or -C3-C7 cycloalkyl, wherein the -C1-C6 alkyl or -C3-C7 cycloalkyl is optionally substituted with one or more of the following: halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", or —S(O)$_2$R';
R is -C1-C6 alkyl, wherein the -C1-C6 alkyl is optionally substituted with one or more of the following: H, halo, —OH, —CN, —COOR', —OR', —SR', —OC(O)R', —NHR', —NR'R", —NHC(O)R', —NHC(O)NR'R", —C(O)NR'R", —NS(O)$_2$R', —S(O)$_2$NR'R", or —S(O)$_2$ R';
X is a bond;
$R_2$ and $R_3$ are independently H, -C1-C6 alkyl, -C3-C7 cycloalkyl, aryl, C5-C10 membered heterocycle,

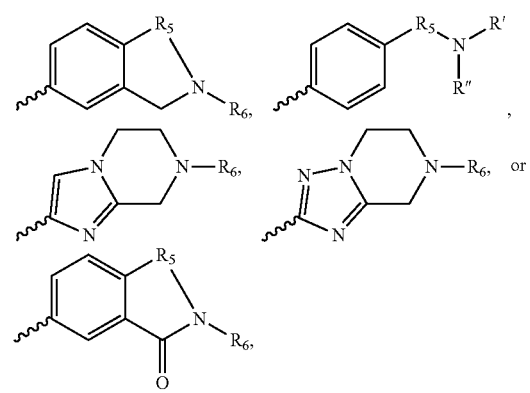

wherein
  the -C1-C6 alkyl, -C3-C7 cycloalkyl, aryl, C5-C10 membered heterocycle is optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)₂R', —S(O)₂NR'R", —S(O)₂R', guanidino, nitro, nitroso, —Cl-C6alkyl, aryl, -C3-C7 cycloalkyl, or 3- to 11-membered heterocycle, wherein the —Cl-C6 alkyl, aryl, -C3-C7 cycloalkyl, or 3- to 11-membered heterocycle is optionally substituted with one or more of the following: halo, —OH, —CN, —COOR', —CH₂NR'R", —OR', —OR'R", —SR', —OC(O)R', —NHR', —NR'R", —NHC(O)R', —NHC(O)NR'R", —C(O)NR'R", —NS(O)₂R', —S(O)₂NR'R", —S(O)₂R', guanidino, nitro, nitroso, —Cl-C6 alkyl, aryl, -C3-C7 cycloalkyl, and wherein R₅ is —Cl-C6 alkyl, —OCH₂CH₂—, —NR₆CH₂CH₂—, —NC(O)CH₂CH₂—; R₆ is H, —C1-C6 alkyl or -C3-C7 cycloalkyl; and R' or R" is independently —H or —Cl-C6 alkyl, or R' and R" together, optionally attaching to N or O atom, form a 4- to 8-membered cyclic structure.

2. The compound of claim 1, wherein Z₁ is

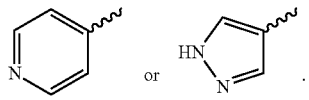

3. The compound of claim 1, wherein Z₂ is phenyl, pyridine, or pyrazole, optionally substituted with halo, —OR', —Cl-C6 alkyl, —OR'OR", —O(CH₂)₂NR'R", wherein the —Cl-C6 alkyl is optionally substituted with one or more of —OR' or NR'R", and wherein the R' or R" are independently —H, methyl or ethyl.

4. The compound of claim 3, wherein Z₂ is selected from the group consisting of:

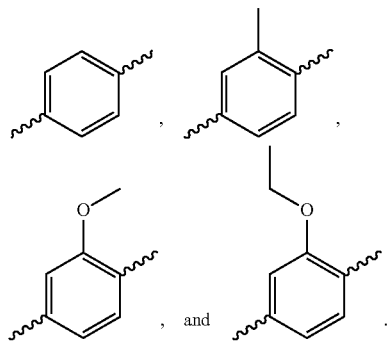

5. The compound of claim 1, wherein R₁ is H, unsubstituted methyl, methoxyethyl or dimethylaminoethyl.

6. The compound of claim 5, wherein R₁ is H.

7. The compound of claim 1, wherein R is methyl or hydroxymethyl.

8. The compound of claim 7, wherein R is hydroxymethyl with S configuration or methyl with R configuration.

9. The compound of claim 1, wherein X is a bond.

10. The compound of claim 1, wherein R₂ is H.

11. The compound of claim 10, wherein R₃ is -C3-C7 cycloalkyl or -C3-C7 cycloalkyl methyl, and wherein the -C3-C7 cycloalkyl or -C3-C7 cycloalkyl methyl is optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)₂R', —S(O)₂NR'R", —S(O)₂R', guanidino, nitro, nitroso, —Cl-C6 alkyl, aryl, -C3-C7 cycloalkyl, or 3- to 11-membered heterocycle.

12. The compound of claim 10, wherein R₃ is H, cyclohexyl, cyclopentyl, cyclobutyl, cyclopropyl, cyclohexyl methyl, cyclopentyl methyl, cyclobutyl methyl, cyclopropyl methyl, phenyl, benzyl, pyrrolidine-3-yl, piperidine-4-yl, (pyrrolidine-3-yl)methyl, (piperidine-4-yl)methyl,

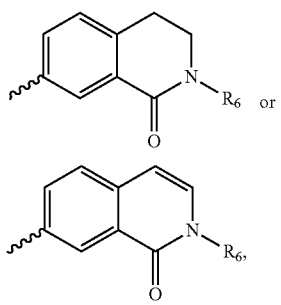

and wherein the cyclohexyl, cyclopentyl, cyclobutyl, cyclopropyl, cyclohexyl methyl, cyclopentyl methyl, cyclobutyl methyl, cyclopropyl methyl phenyl, benzyl, pyrrolidine-3-yl, piperidine-4-yl, (pyrrolidine-3-yl)methyl or (piperidine-4-yl)methyl is optionally substituted with H, halo, —OH, —CN, —COOR', —OR', —SR', —OC(O)R', —NHR', —NR'R", —CNR'R", —NHC(O)R', —NHC(O)NR'R", —C(O)NR'R", —NS(O)₂R', —S(O)₂NR'R", —S(O)₂R', guanidino, nitro, nitroso, —Cl-C6 alkyl, aryl, -C3-C7 cycloalkyl, or 3- to 11-membered heterocycle.

13. The compound of claim 10, wherein R₃ is cyclopentyl or cyclohexyl.

14. The compound of claim 1, wherein Z₂ is unsubstituted phenyl, pyridine or pyrazole, or phenyl substituted with halo, —OR', —Cl-C6 alkyl, —OR'OR", —O(CH₂)₂NR'R", wherein the —Cl-C6 alkyl is optionally substituted with one or more of —OR' or NR'R"; R₁ is H, unsubstituted methyl or dimethylamine; X is a bond; R₂ is H; and R' or R" is independently —H, methyl or ethyl.

15. The compound of claim 1, selected from the group consisting of:

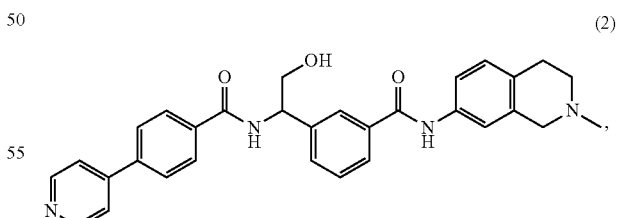

(2)

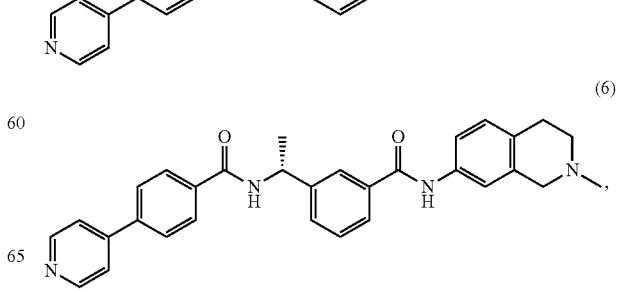

(6)

(7)
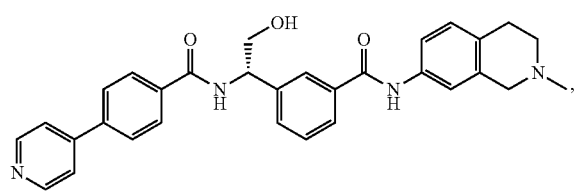
(8)
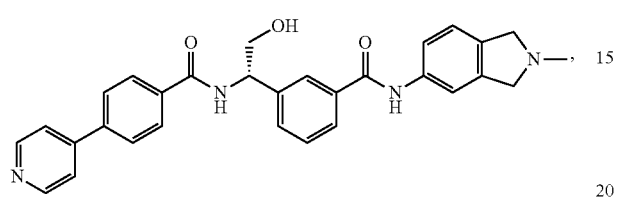
(9)
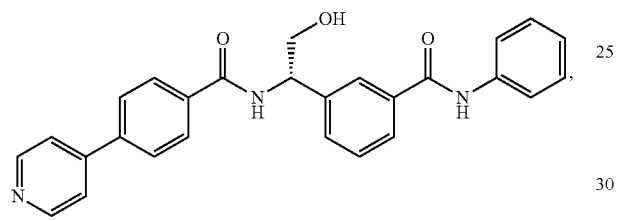
(10)
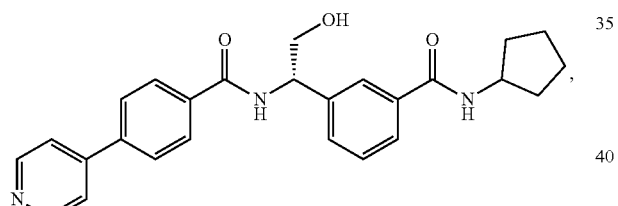
(11)
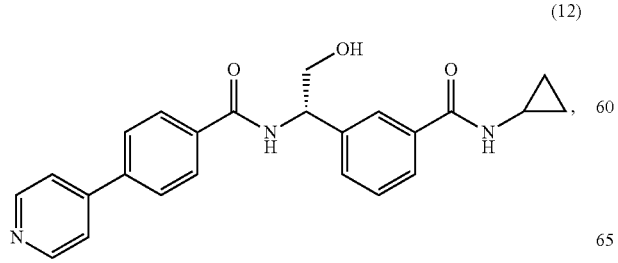
(12)
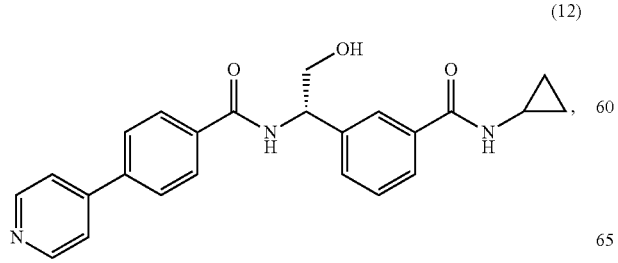
(13)
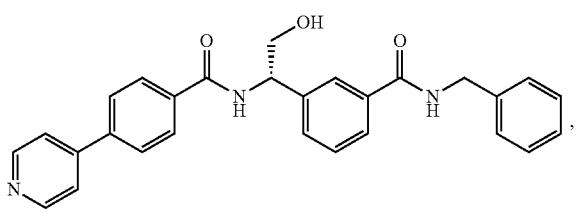
(14)
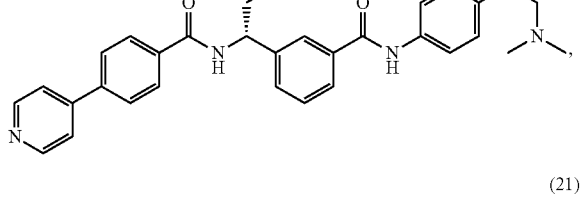
(20)
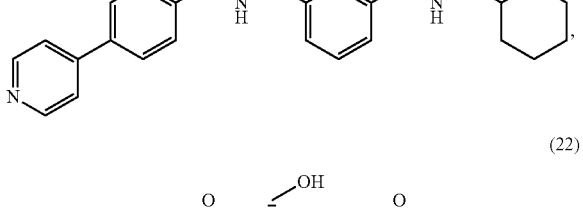
(21)
(22)
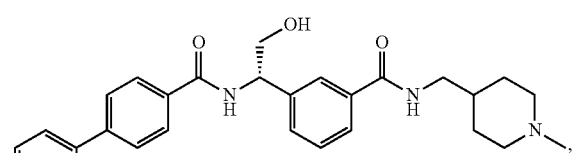
(23)
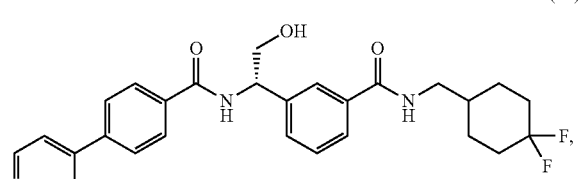
(24)
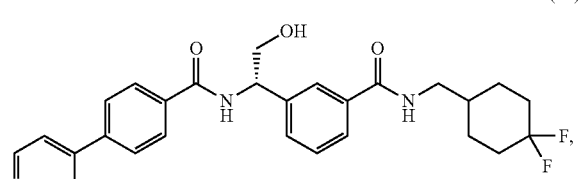

(25)
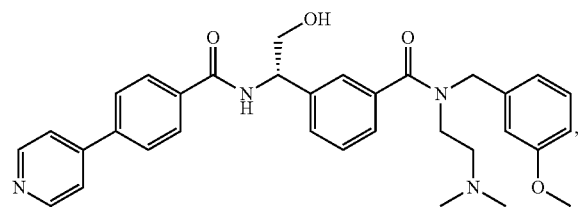
(26)
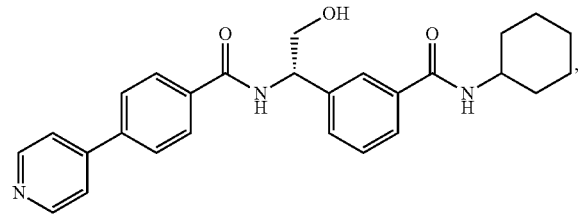
(27)
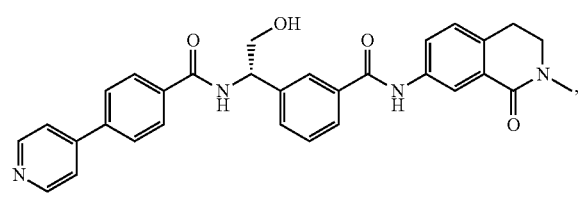
(28)
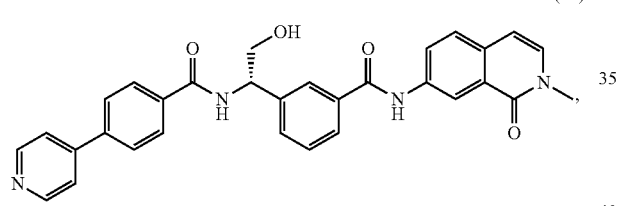
(29)
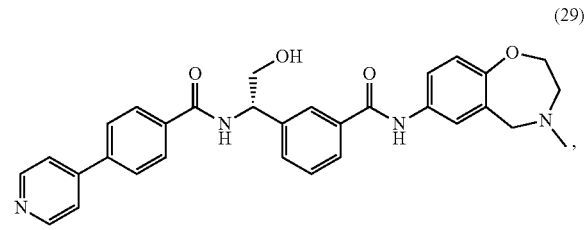
(30)
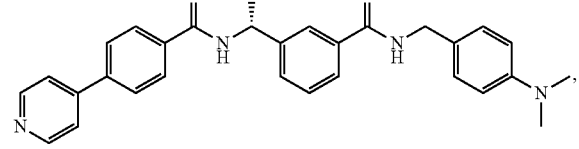
(31)
(32)
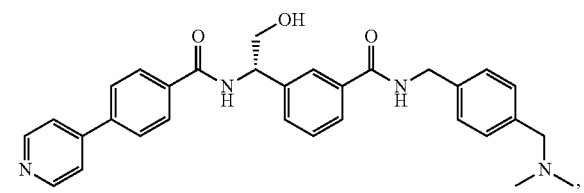
(33)
(34)
(35)
(36)
(37)
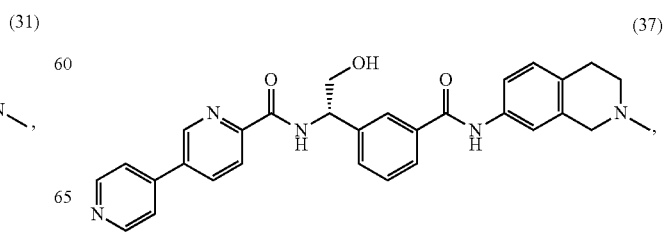

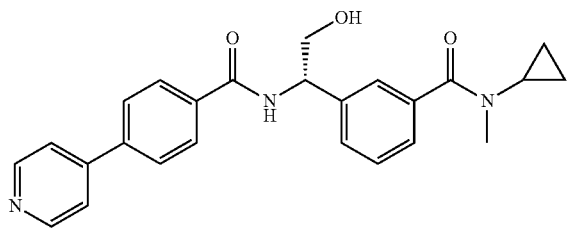
(38)
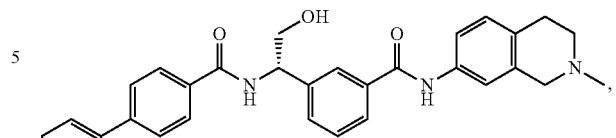
(44)
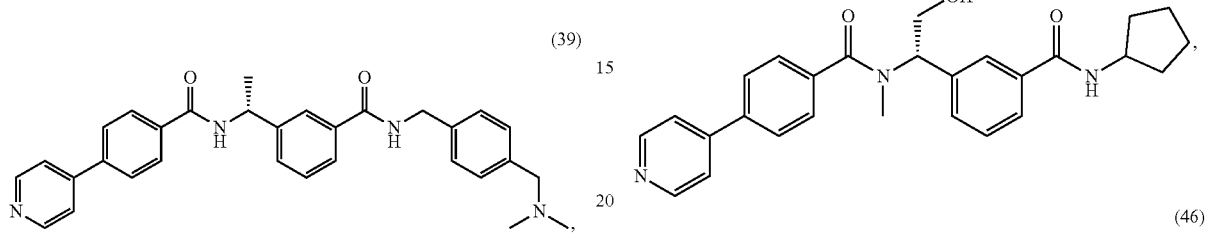
(39), (45)
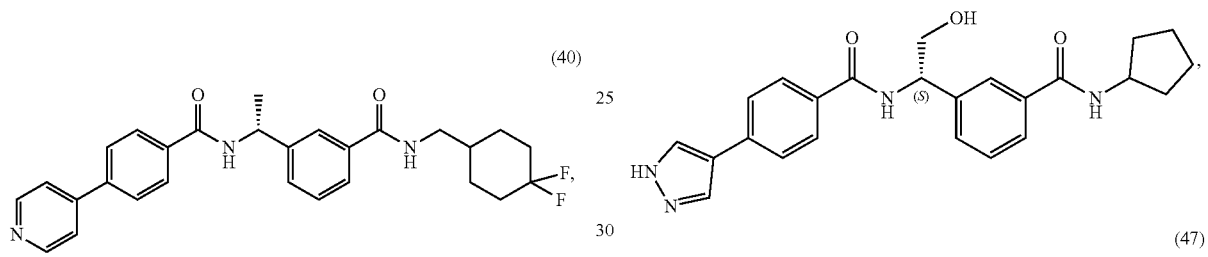
(40), (46)
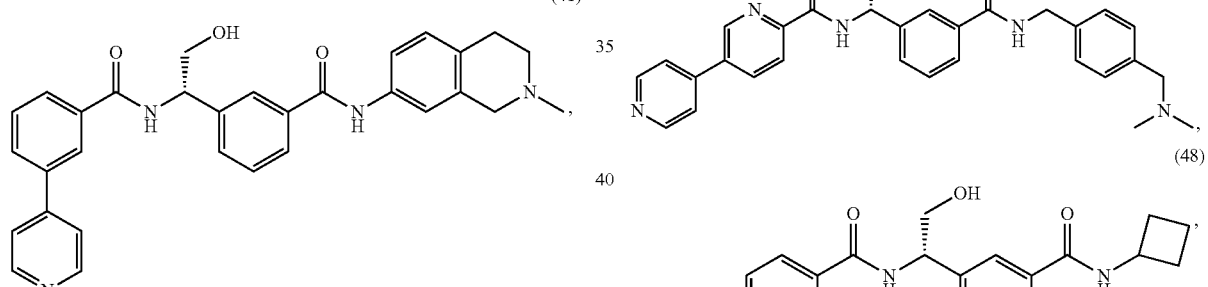
(41), (47), (48)
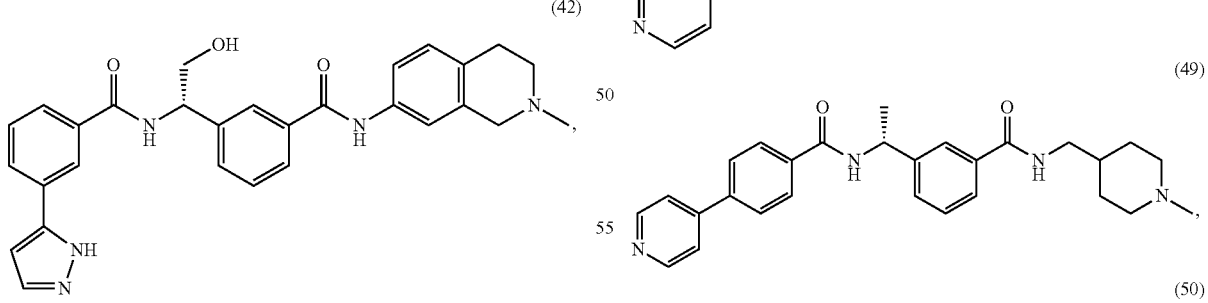
(42), (49)
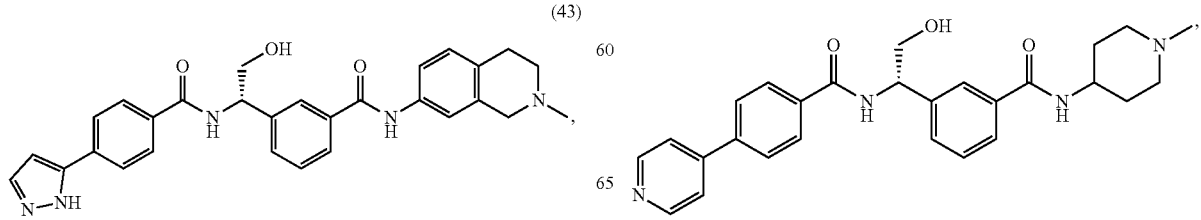
(43), (50)

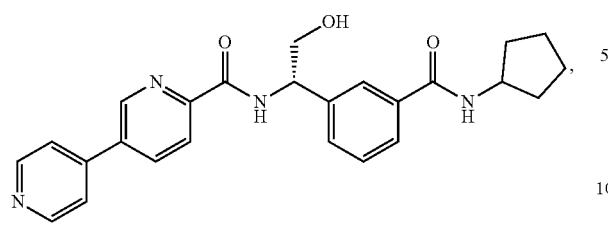
(51)
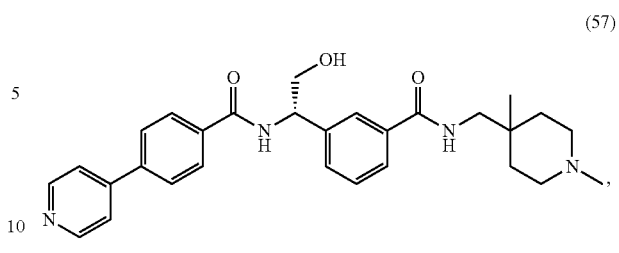
(57)
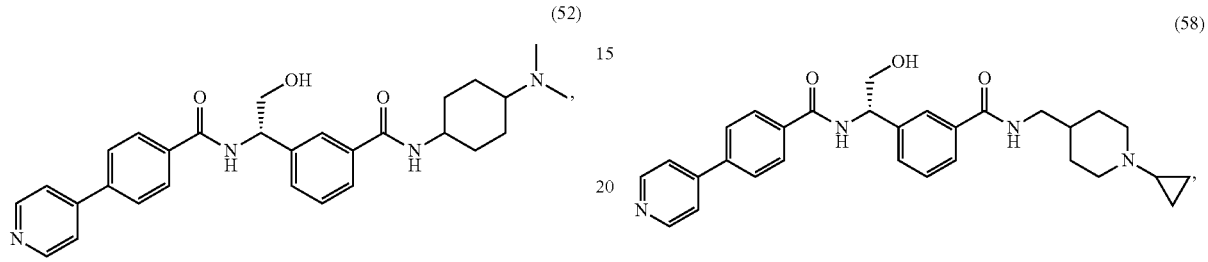
(52) (58)
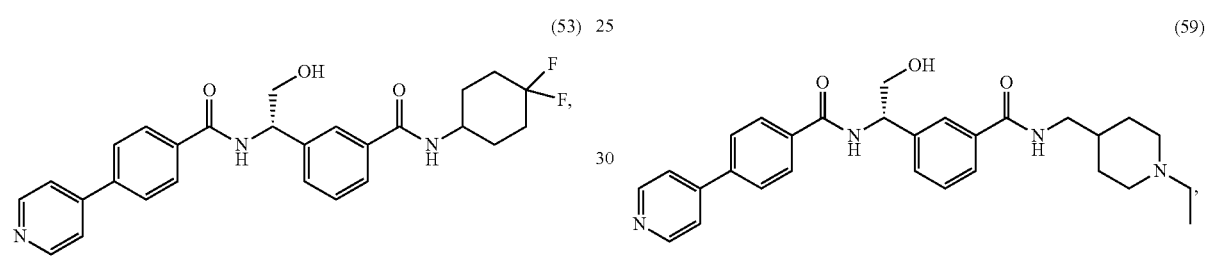
(53) (59)
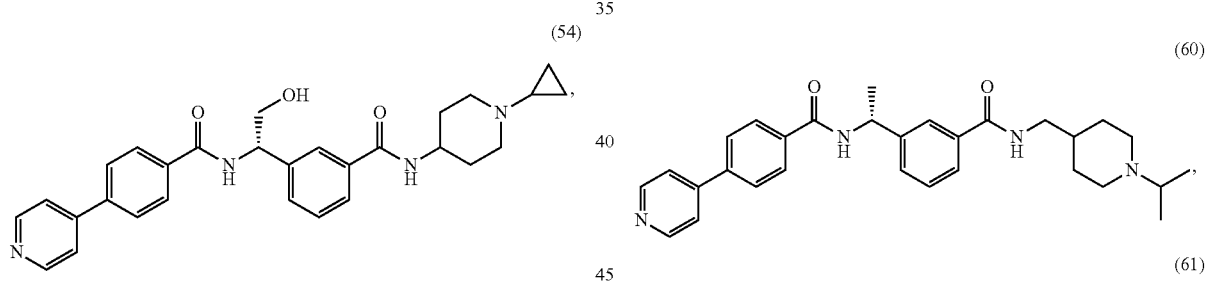
(54) (60)
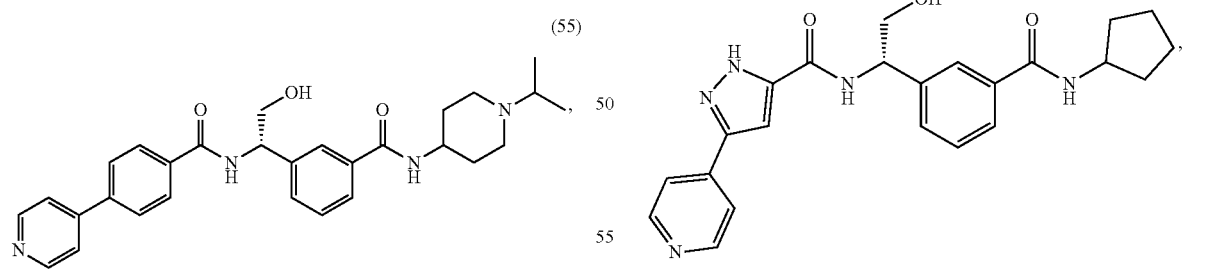
(55) (61)
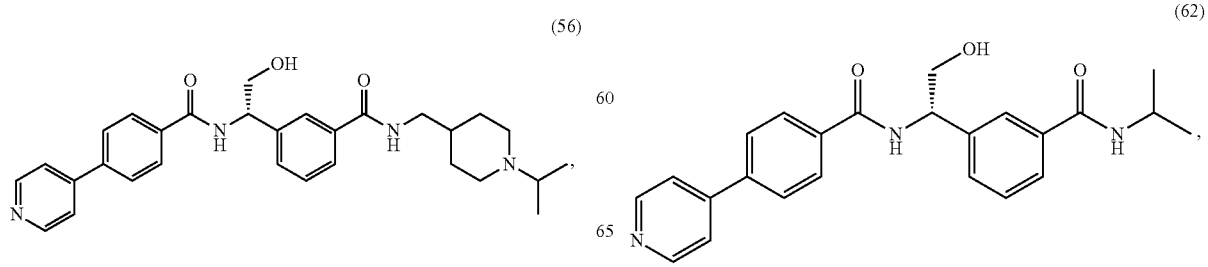
(56) (62)

(63)
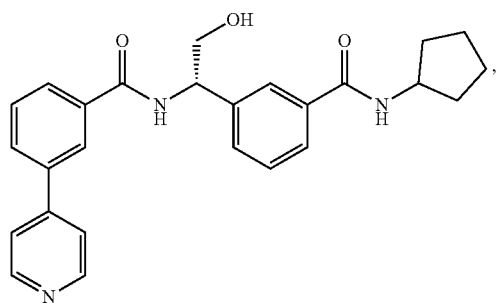
(64)
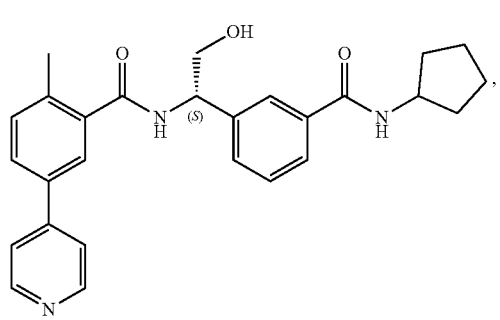
(65)
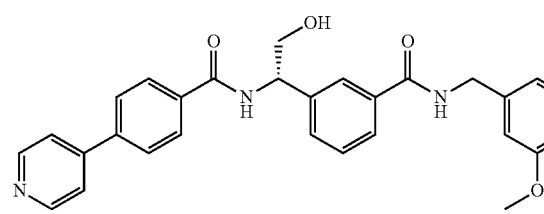
(66)
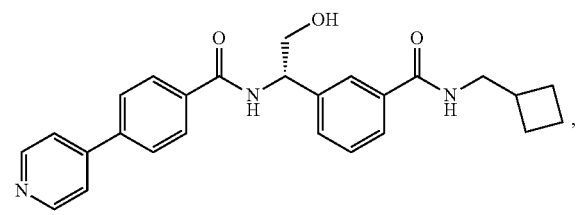
(67)
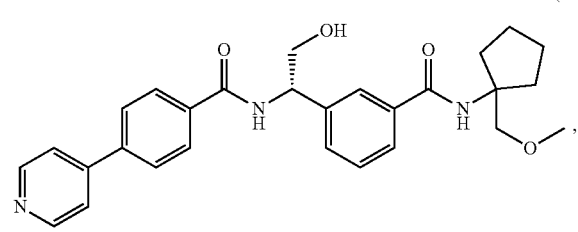
(69)
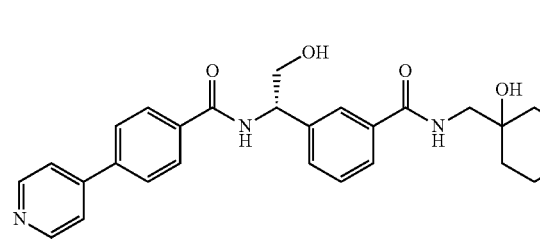
(70)
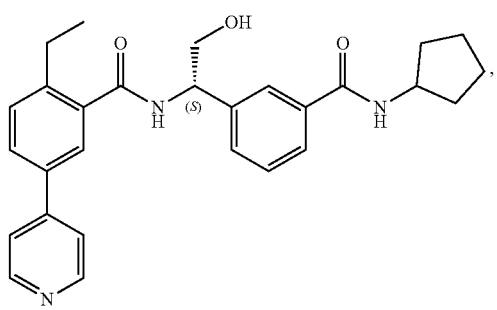
(71)
(72)
(73)
(74)
(75)
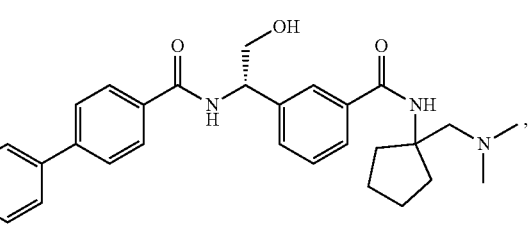
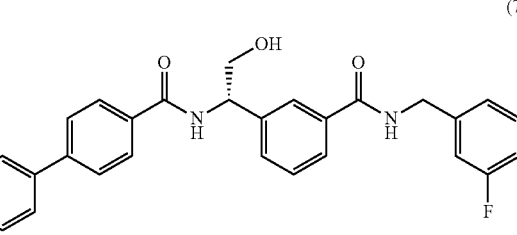

(76) 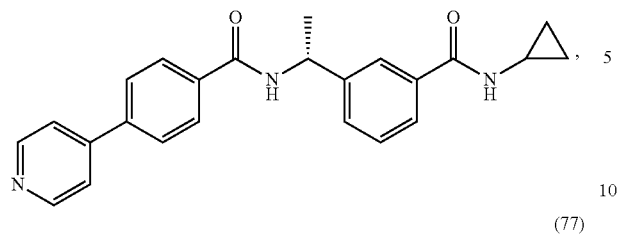
(77) 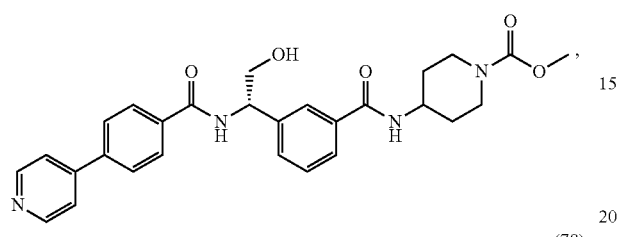
(78) 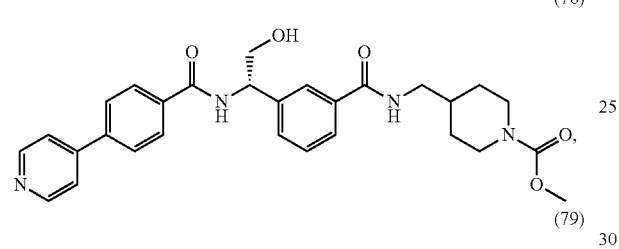
(79) 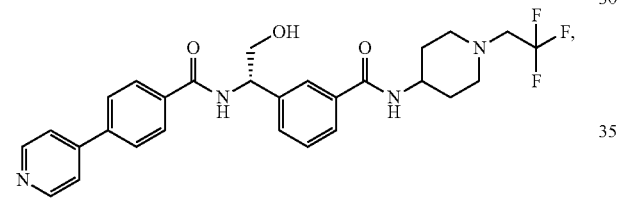
(80) 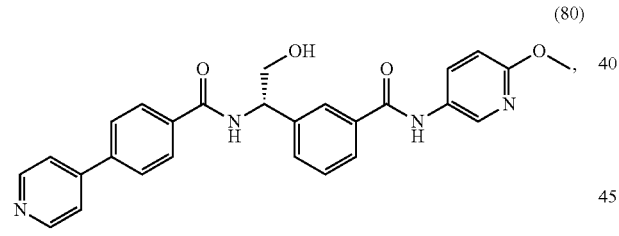
(81) 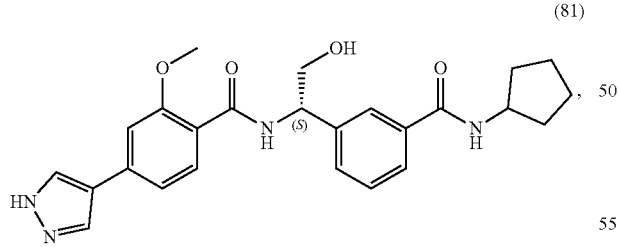
(82) 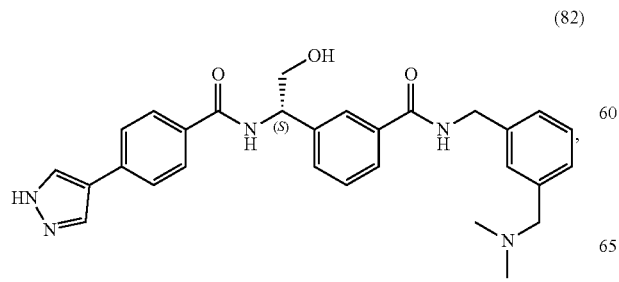
(83) 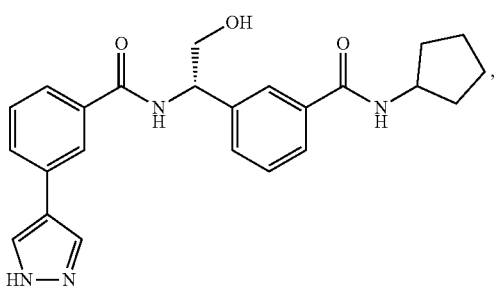
(84) 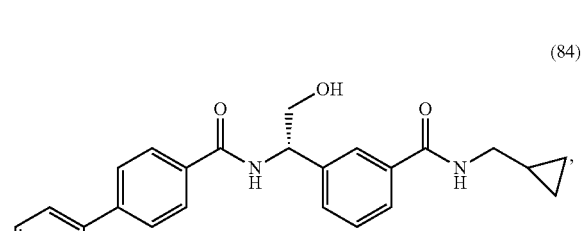
(85) 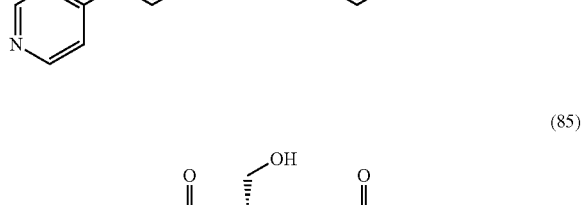
(86) 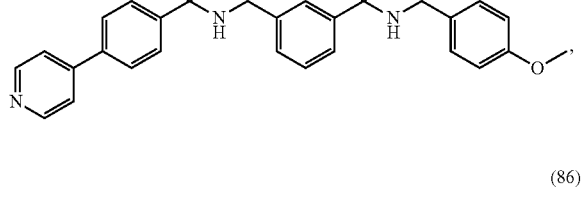
(87) 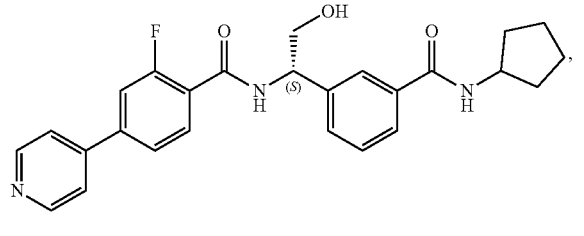
(88) 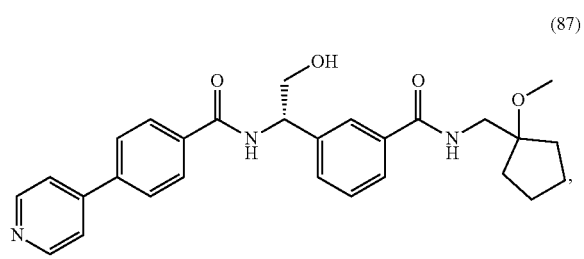

(89) 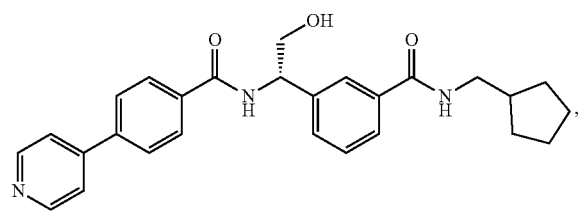
(90) 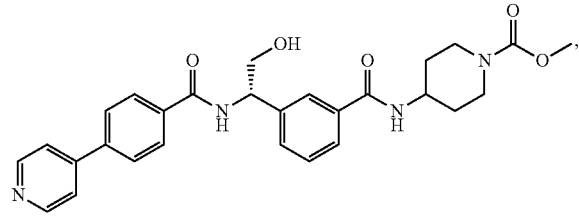
(91) 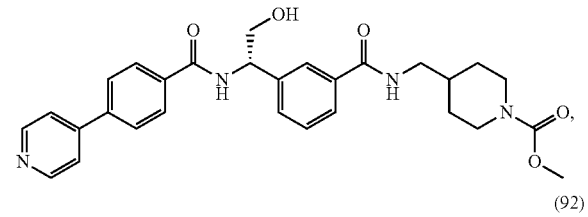
(92) 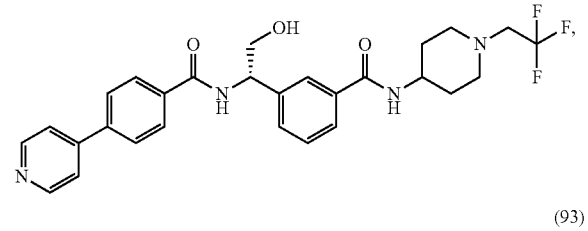
(93) 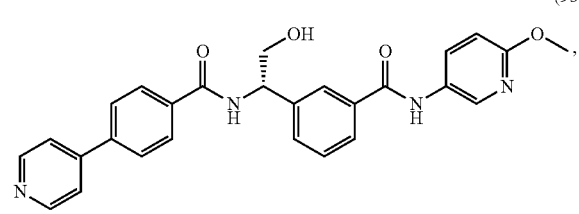
(95) 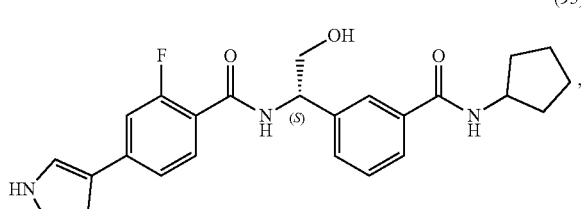
(96) 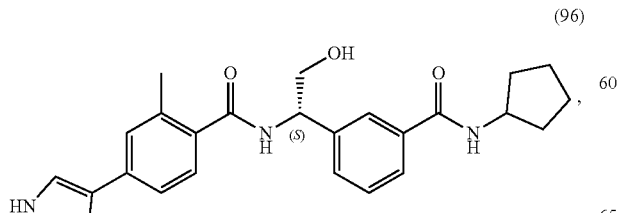
(97) 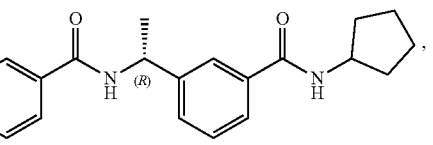
(98) 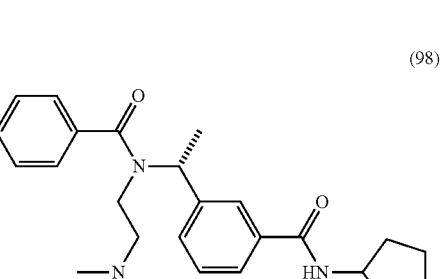
(100) 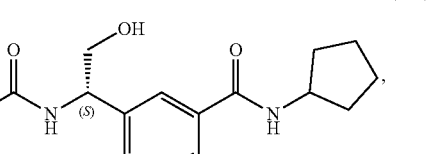
(101) 
(102) 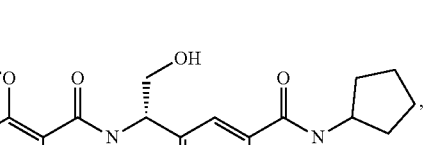
(103) 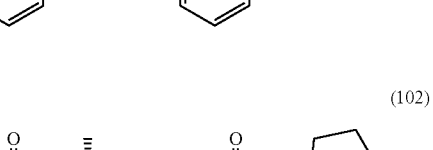

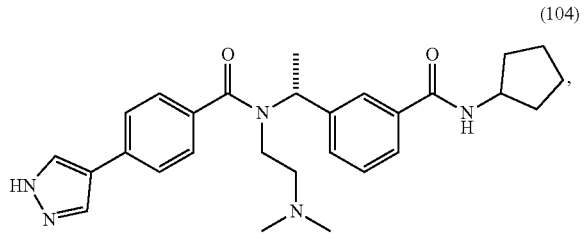
(104)
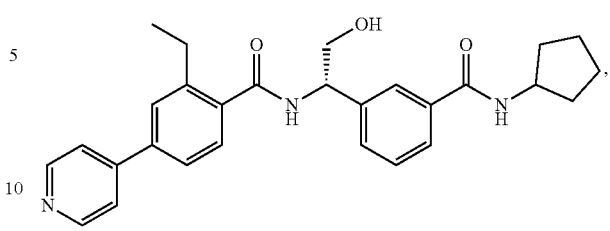
(116)
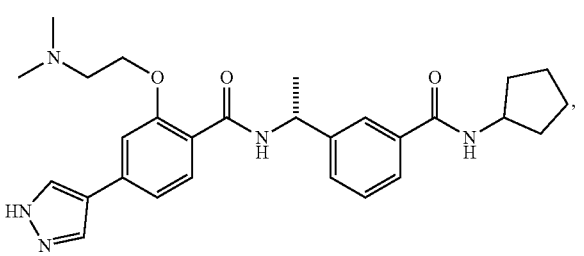
(105)
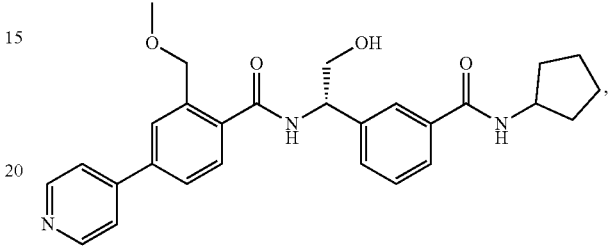
(117)
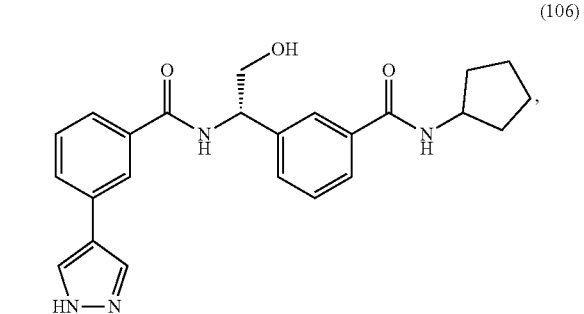
(106)
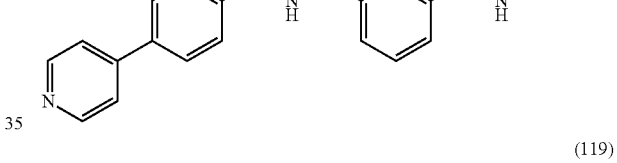
(118)
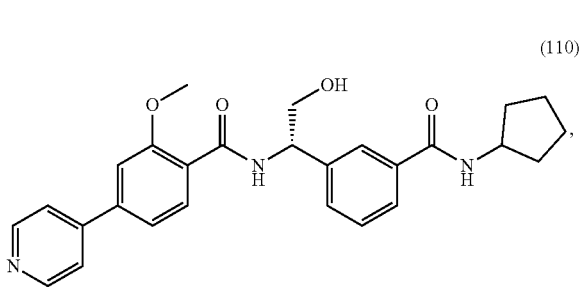 [SMILES: O=C(NC1CCCC1)c1cccc([C@@H](CO)NC(=O)c2ccc(-c3ccncc3)cc2)c1]
(110)
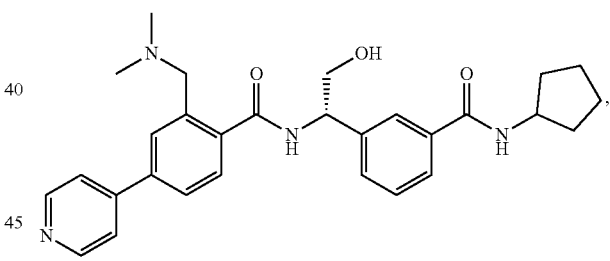
(119)
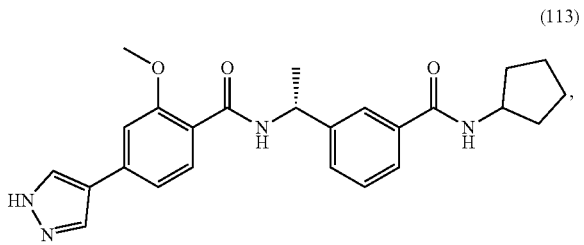
(113)
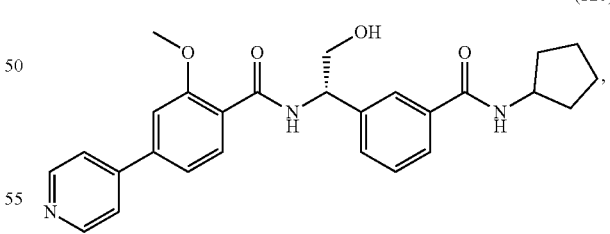
(120)
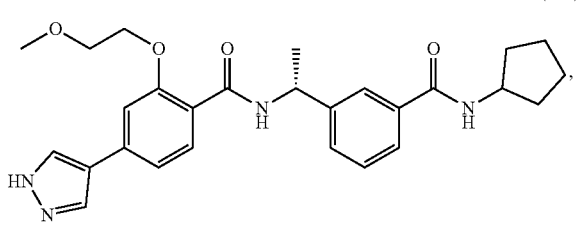
(115)
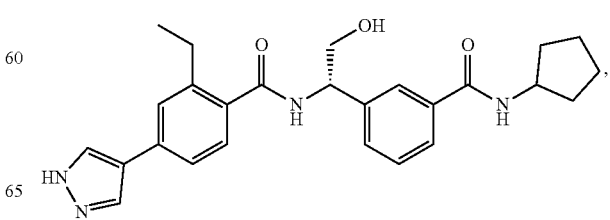
(121)

(122)
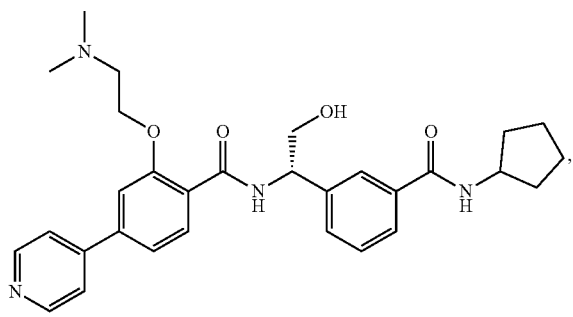
(123)
(127)
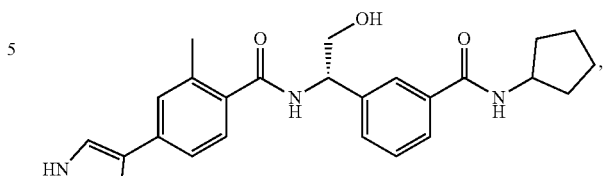
(128)
(129)
(124)
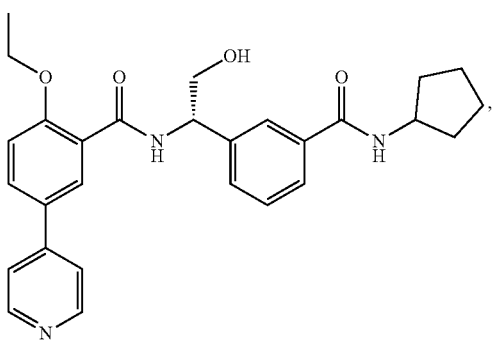
(130)
(125)
(131)
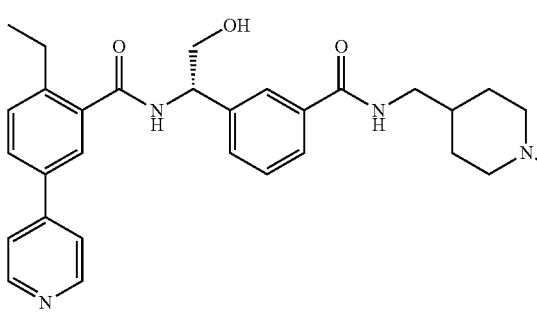
, and
(126)
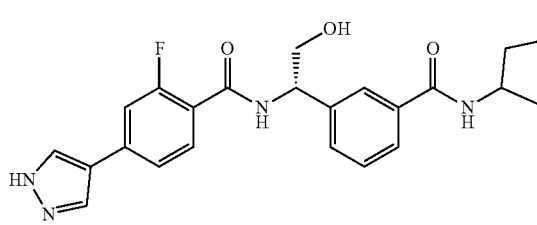
(132)
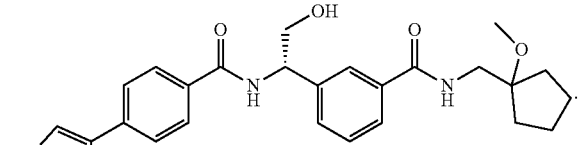
16. The compound of claim 15, selected from the group consisting of:

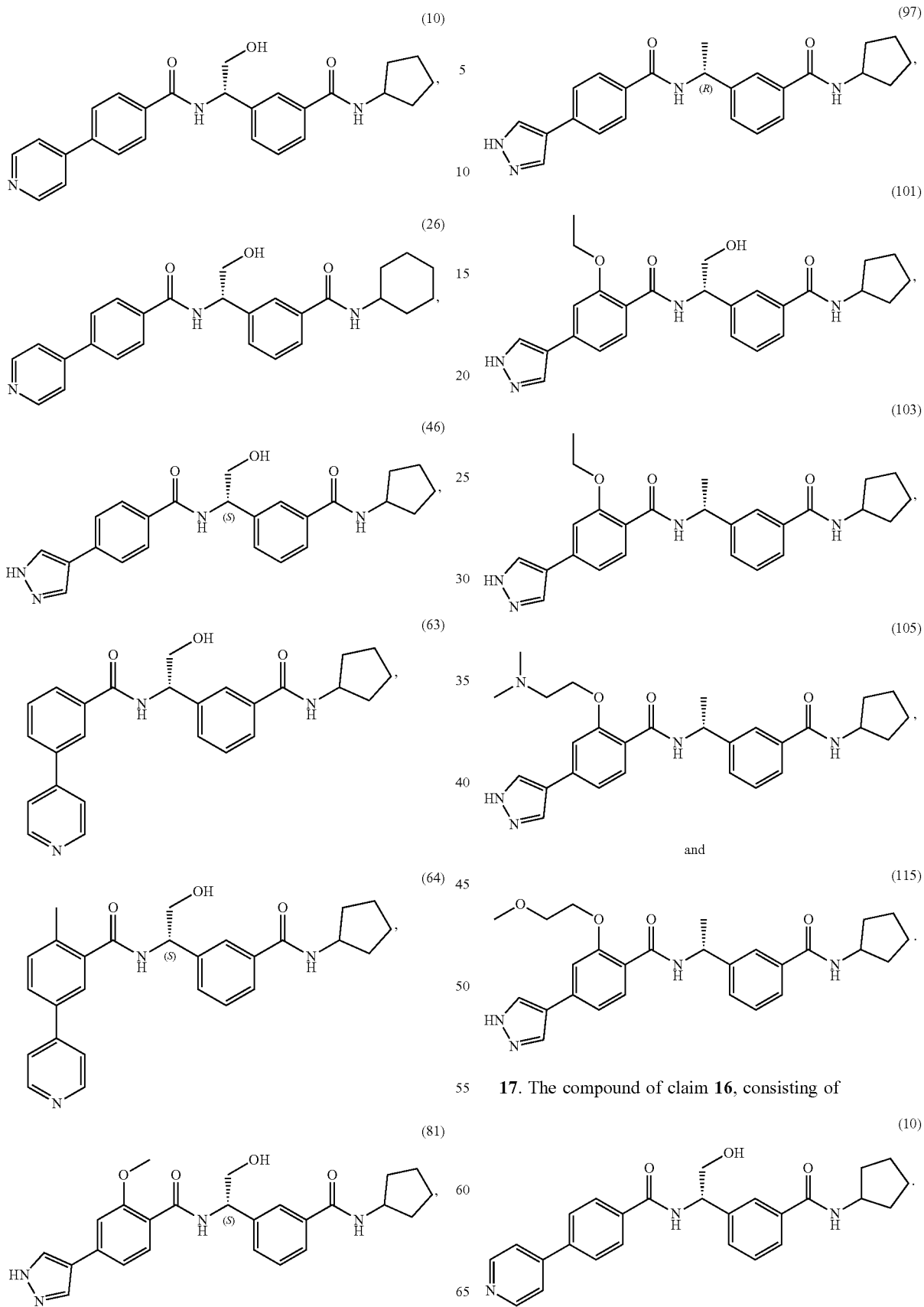
17. The compound of claim 16, consisting of

18. The compound of claim 16, consisting of
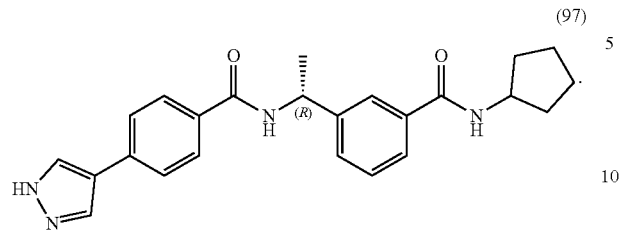
(97)
19. A pharmaceutical composition comprising the compound of claim 1 and a pharmaceutically acceptable carrier.
* * * * *